US012600944B2

(12) United States Patent
Basar et al.

(10) Patent No.: US 12,600,944 B2
(45) Date of Patent: Apr. 14, 2026

(54) MULTIPLEX GENOME EDITING OF IMMUNE CELLS TO ENHANCE FUNCTIONALITY AND RESISTANCE TO SUPPRESSIVE ENVIRONMENT

(71) Applicant: Board of Regents, The University of Texas System, Austin, TX (US)

(72) Inventors: Rafet Basar, Houston, TX (US); Elizabeth Shpall, Houston, TX (US); Katy Rezvani, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 980 days.

(21) Appl. No.: 17/309,408

(22) PCT Filed: Nov. 27, 2019

(86) PCT No.: PCT/US2019/063641
§ 371 (c)(1),
(2) Date: May 25, 2021

(87) PCT Pub. No.: WO2020/113029
PCT Pub. Date: Jun. 4, 2020

(65) Prior Publication Data
US 2022/0031749 A1 Feb. 3, 2022

Related U.S. Application Data

(60) Provisional application No. 62/772,406, filed on Nov. 28, 2018.

(51) Int. Cl.
| | |
|---|---|
| *C12N 5/0783* | (2010.01) |
| *A61K 40/15* | (2025.01) |
| *A61K 40/31* | (2025.01) |
| *A61K 40/42* | (2025.01) |
| *C07K 14/725* | (2006.01) |
| *C12N 9/22* | (2006.01) |
| *C12N 15/113* | (2010.01) |
| *C12N 15/85* | (2006.01) |

(52) U.S. Cl.
CPC ........... *C12N 5/0636* (2013.01); *A61K 40/15* (2025.01); *A61K 40/31* (2025.01); *A61K 40/42* (2025.01); *C07K 14/7051* (2013.01); *C12N 5/0646* (2013.01); *C12N 9/22* (2013.01); *C12N 15/113* (2013.01); *C12N 15/85* (2013.01); *C12N 2310/20* (2017.05)

(58) Field of Classification Search
CPC ............... A61K 35/17; A61K 39/4613; A61K 39/4631; C07K 14/7051; C12N 5/0636; C12N 9/22; C12N 15/113; C12N 2310/20; C12N 5/0646; C12N 2510/00
See application file for complete search history.

(56) References Cited

U.S. PATENT DOCUMENTS

| | | | |
|---|---|---|---|
| 2014/0120622 A1 | 5/2014 | Gregory et al. | |
| 2017/0067021 A1* | 3/2017 | Moriarity | A61K 39/4632 |
| 2018/0273903 A1 | 9/2018 | Zhang et al. | |

FOREIGN PATENT DOCUMENTS

| | | | |
|---|---|---|---|
| JP | 2015-531242 A | 11/2015 | |
| WO | WO 2014/059173 | 4/2014 | |
| WO | 2014/184744 A1 | 11/2014 | |
| WO | WO 2017/001572 | 1/2017 | |
| WO | 2017/023801 A1 | 2/2017 | |
| WO | WO 2017/017184 | 2/2017 | |
| WO | WO 2017/100861 | 6/2017 | |
| WO | WO 2018/068135 | 4/2018 | |
| WO | 2018/115189 A1 | 6/2018 | |
| WO | WO 2018/195339 | 10/2018 | |
| WO | WO-2019106163 A1 * | 6/2019 | ........ A61F 13/51104 |

OTHER PUBLICATIONS

Mandal A, Viswanathan C. Natural killer cells: In health and disease. Hematol Oncol Stem Cell Ther. Jun. 2015;8(2):47-55. doi: 10.1016/j.hemonc.2014.11.006. Epub Dec. 27, 2014. PMID: 25571788 (Year: 2015).*

Delconte et al., "CIS is a potent checkpoint in NK cell-mediated tumor immunity," Nature Immunology, 17(7):816-24, 2016.

English translation of Office Communication issued in Chinese Patent Application No. 201980088334.X, dated Aug. 26, 2023.

Kim et al., "Association of CD47 with natural killer cell-mediated cytotoxicity of head-and-neck squamous cell carcinoma lines," Tumor Biology, 29(1):28-34, 2008. (Abstract).

Shook et al., "Natural killer cell engineering for cellular therapy of cancer," Tissue Antigens, 78(6):09-415, 2011.

Young et al., "A2AR Adenosine Signaling Suppresses Natural Kill Cell Maturation in the Tumor Microenvironment," Caner Res., 78(4):1003-1016, 2008.

Blake et al., "Suppression of Metastases Using a New Lymphocyte Checkpoint Target for Cancer Immunotherapy," Cancer Discov., 6(4):446-459, 2016.

English translation of Office Communication issued in Chinese Patent Application No. 201980088334.X, dated Jun. 29, 2024.

Zhang et al., "Blockade of the checkpoint receptor TIGIT prevents NK cell exhaustion and elicits potent anti-tumor immunity," Nat. Immunl., 19:723-732, 2018.

English translation of Office Communication issued in Japanese Patent Application No. 2021-530101, dated Sep. 28, 2023.

Hermann Prof. Dr. Einsele: "Immunotherapy and cellular therapy", Apr. 22, 2017 (Apr. 22, 2017), pp. 1-61, XP055564330, Retrieved from the Internet: URL:http://cme-utilities.com/mailshotcme/COMY/presentations/0512092954116h00-16h25-HERMANN-EINSELE.pdf [retrieved on Mar. 4, 2019] p. 51.

(Continued)

*Primary Examiner* — Teresa E Knight
*Assistant Examiner* — Michael Angelo Riga

(57) ABSTRACT

Provided herein are methods for producing immune cells with disruption of multiple genes. Further provided are methods for inserting a chimeric antigen receptor at a gene locus of an immune cell.

14 Claims, 38 Drawing Sheets

Specification includes a Sequence Listing.

(56)     References Cited

OTHER PUBLICATIONS

Jiangtao Ren et al: "A versatile system for rapid multiplex genome-edited CAR T cell generation", ONCOTARGET, vol. 8, No. 10, Feb. 9, 2017 (Feb. 9, 2017), pp. 17002-17011.

Sun et al., "High NKG2A expression contributes to NK cell exhaustion and predicts a poor prognosis of patients with liver cancer," OncoImmunology, 6(1):e1264562, 12 pages, 2016.

Third Party Observations submitted in European Patent Application No. 19827952.3, filed Oct. 17, 2025.

Office Communication issued in Australian Patent Application No. 2019386140, dated Sep. 25, 2025.

Kaulfuss et al., "The NK cell checkpoint NKG2A maintains expansion capacity of human NK cells," Scientific Reports, 13(1):10555, 12 pages, 2023.

Office Communication issued in European Patent Application No. 19827952.3, dated Jan. 21, 2026.

Sparano et al., "Autocrine TGF-β1 drive tissue-specific differentiation and function of resident NK cells," The Journal of Experimental Medicine, 222(3):e20240930, 24 pages, 2025 (with Supplemental Material).

* cited by examiner

Murine CD19 CAR-NK
+
Raji

CD5 CAR NK
+
CCRF-CEM

SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
aggccacata gtgctgcaca                                                    20

```
<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
tgtacagcag tggctggtgg                                              20

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
aacaactatc gttaccacag                                              20

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
ctcctcggtg tacatcacgg                                              20

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
agtagttggt gacgttctgc                                              20

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
accctgatgg gacgtacact                                              20

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 7
aggcacagta gaagccgtat                                                    20

<210> SEQ ID NO 8
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
agacgggcac gaggttccct                                                    20

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
tcacgcacaa gaaacgtcca                                                    20

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
ccccttcggt caccacgagc                                                    20

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
atttactgtc acggttccca                                                    20

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
ccccatagat gattatgcat                                                    20

<210> SEQ ID NO 13
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
gacggctgag gagcggaaga                                                    20

<210> SEQ ID NO 14
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
tgtggaggtg agcaatcccc                                                    20

<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
gtcaccctgg ttcttgcgac                                                    20
```

MULTIPLEX GENOME EDITING OF IMMUNE CELLS TO ENHANCE FUNCTIONALITY AND RESISTANCE TO SUPPRESSIVE ENVIRONMENT

This application is a national phase application under 35 U.S.C. § 371 that claims priority to International Application No. PCT/US2019/063641 filed Nov. 27, 2019, which claims priority to U.S. Provisional Patent Application Ser. No. 62/772,406, filed Nov. 28, 2018, both of which applications are incorporated by reference herein in their entirety.

INCORPORATION OF SEQUENCE LISTING

The instant application contains a Sequence Listing which has been submitted electronically in ASCII format and is hereby incorporated by reference in its entirety. Said ASCII copy, created on May 25, 2021, is named SL_MDAC_P1184US.txt and is 4,266 bytes in size.

BACKGROUND

1. Technical Field

The present invention relates generally to the fields of immunology, cell biology, molecular biology, and medicine. More particularly, it concerns multiplex editing of immune cells and methods of use thereof.

2. Description of Related Art

Cellular immunotherapy holds much promise for the treatment of cancer. However, most immunotherapeutic approaches when applied alone are of limited value against the majority of malignancies, especially solid tumors. Reasons for this limited success include reduced expression of tumor antigens on the surface of tumor cells, which reduces their detection by the immune system, the expression of ligands for inhibitory receptors such as PD1, NKG2A, TIGIT or CISH that induce immune cell inactivation; and the induction of cells (e.g., regulatory T cells or myeloid-derived suppressor cells) in the microenvironment that release substances such as transforming growth factor-β (TGFβ) and adenosine that suppress the immune response and promote tumor cell proliferation and survival. Thus, there is an unmet need for improved methods of cellular immunotherapy.

SUMMARY

The disclosure provides compositions and methods related to cancer immunotherapy particularly including engineered immune cells. Specific embodiments concern certain immune cells that have been modified by the hand of man to lack expression of or have reduced expression of one, two, or more genes, and in specific cases the cells with such modification(s) also express one or more heterologous proteins, including non-natural proteins such antigen receptors. Also included are methods of producing the non-natural immune cells. In certain cases, the introduction of the heterologous antigen receptor is at the genomic locus of a gene being reduced or eliminated in expression.

In one embodiment, the present disclosure provides an in vitro method for the disruption of at least two genes in an immune cell, wherein the at least two genes are selected from the group consisting of NKG2A, SIGLEC-7, LAG3, TIM3, CISH, FOXO1, TGFBR2, TIGIT, CD96, ADORA2, NR3C1, PD1, PDL-1, PDL-2, CD47, SIRPA, SHIP1, ADAM17, RPS6, 4EBP1, CD25, CD40, IL21R, ICAM1, CD95, CD80, CD86, IL10R, CD5, CD7, and a combination thereof. In particular aspects, three, four, five, or six or more genes are disrupted. In specific aspects, the disruption of two or more genes is simultaneous, such as in the same method step. The method may comprise introducing a guide RNA (gRNA) for each gene to the immune cell.

The method can comprise the knockdown of particular combinations of genes, such as the following, for example: (a) NKG2A and CISH, (b) NKG2A and TGFBRII, (c) CISH and TGFBRII, (d) TIGIT and FOXO1, (e) TIGIT and TGFBRII, (f) CD96 and FOXO1, (g) CD96 and TGFBRII, (h) FOXO1 and TGFBRII, (i) CD96 and TIGIT, (j) CISH and TIGIT, (k) TIM3 and CISH, (l) TIM3 and TGFBRII, (m) FOXO1 and TGFBRII, (n) TIM3 and TIGIT, (o) SIGLEC7 and CISH, (p) SIGLEC7 and TGFBRII, (q) CD47 and CISH, (r) CD47 and TGFBRII, (s) SIRPA and CISH, (t) SIRPA and TGFBRII, (u) CD47 and TIGIT, (v) CD47 and SIRPA, (w) A2AR and CISH, (x) A2AR and TGFBRII, (y) ADAM17 and CISH, (z) TGFBRII and ADAM17, (a) A2AR and TIGIT, (b) SHP1 and CISH, (c) CISH and TGFBRII, (d) SHP1 and TGFBRII, (e) SHP1 and TIGIT, or (f) SHP1 and TIM3. The method can comprise the knockdown of (1) NKG2A, CISH, and TGFBRII, (2) TIGIT, FOXO1, and TGFBRII, (3) TGFBRII, CD96, and TIGIT, (4) TGFBR2, CISH, and TIGIT, (5) TIM3, CISH, and TGFBRII, (6) CD96, FOXO1, and TGFBRII, (7) TGFBRII, TIM3, and TIGIT, (8) SIGLEC7, CISH, and TGFBRII, (9) CD47, CISH, and TGFBRII, (10) SIRPA, CISH, and TGFBRII, (11) TGFBRII, CD47, and TIGIT, (12) TGFBRII, CD47, and SIRPA, (13) A2AR, CISH, and TGFBRII, (14) TGFBRII, CISH, and ADAM17, (15) TGFBRII, TIM3, and TIGIT, (16) TGFBRII, A2AR, and TIGIT, (17) SHP1, CISH, and TGFBRII, (18) TGFBRII, CISH, and SHP1, (19) TGFBRII, SHP1, and TIGIT, or (20) TGFBRII, SHP1, and TIM3. Any of the above subgroups may be combined with a second subgroup as disclosed above. For example, any one of subgroups a-j1 may be combined with any one or more of the other subgroups a-j1, any one or more of subgroups a-j1 may be combined with any one or more of the other subgroups 1-23, or any one or more of subgroups 1-23 may be combined with any one or more of the other subgroups 1-23.

In some aspects, the method further comprises introducing to the cell an RNA-guide endonuclease, such as Cas9. Introducing the RNA-guided endonuclease may comprise introducing a nucleic acid, such as mRNA, encoding the RNA-guided endonuclease into the immune cell.

In certain aspects, the immune cell is a T cell, NK cell, B cell, macrophage, NK T cell, or stem cell. In alternative cases, the immune cell is not a T cell, including not a CAR T cell. In some aspects, the immune cell is engineered to express one or more chimeric antigen receptors (CAR) and/or one or more T cell receptors (TCR). The immune cell may be virus-specific, such as a virus-specific T cell. The T cell may be a regulatory T cell. The B cell may be a regulatory B cell. In some aspects, the stem cell is a mesenchymal stem cell (MSC) or an induced pluripotent stem (iPS) cell. In particular aspects, the T cell is a $CD8^+$ T cell, $CD4^+$ T cell, or gamma-delta T cell. The immune cell may be isolated from peripheral blood, cord blood, bone marrow, or a mixture thereof. In some aspects, the cord blood is pooled from 2 or more individual cord blood units.

In some aspects, an introducing step comprises transfecting or transducing. For example, introducing comprises electroporation that may performed more than once, such as two or three rounds of electroporation. In some aspects, a first group of CRISPR gRNAs are introduced in a first electroporation and a second group of CRISPR gRNAs are introduced in a second round of electroporation. In specific cases, the first group of CRISPR gRNAs are different than the second group of CRISPR gRNAs. In particular aspects, the first group and/or second group of CRISPR gRNAs comprise 1, 2, 3, or 4 or more CRISPR gRNAs. In some aspects, two CRISPR gRNAs are introduced in a first electroporation and two different CRISPR gRNAs are introduced in a second round of electroporation. In specific embodiments, a group of CRISPR gRNAs comprises a group of gRNAs at least two of which target different genes; in particular embodiments, the group of gRNAs each target different genes.

In particular aspects, the method comprises disrupting NKG2A, CD47, TGFβR2, and CISH; NKG2A, CISH, TGFβR2 and ADORA2; NKG2A, TGFβR2 and CISH; TIGIT, CD96, CISH, and ADORA2; or ADAM17, TGFβR2, NKG2A, and SHP1.

In some aspects, the disruption results in enhanced anti-tumor cytotoxicity, in vivo proliferation, in vivo persistence, and/or improved function of the immune cell. In particular aspects, the immune cell has increased secretion of IFN-γ, CD107, and/or TNFα, compared to in the absence of the modification(s). In some aspects, the immune cell has increased production of perforin and/or granzyme B, compared to in the absence of the modification(s).

In additional aspects, the method further comprises introducing a CAR and/or TCR to an immune cell, such as introducing a nucleic acid encoding the CAR and/or TCR into the immune cell. In some aspects, the nucleic acid is in an expression vector, such as a retroviral vector. In certain aspects, the vector is an adenovirus-associated vector, such as AAV6. In some aspects, the vector further comprises an inhibitory gene sequence, such as an inhibitory gene sequence selected from the group consisting of NKG2A, SIGLEC-7, LAG3, TIM3, CISH, FOXO1, TGFBR2, TIGIT, CD96, ADORA2, NR3C1, PD1, PDL-1, PDL-2, CD47, SIRPA, SHIP1, ADAM17, RPS6, 4EBP1, CD25, CD40, IL21R, ICAM1, CD95, CD80, CD86, IL10R, CD5, CD7, and a combination thereof. In particular aspects, the vector further comprises a guide RNA for the inhibitory gene. The CAR may be flanked by homology arms for the inhibitory gene. In some aspects, introducing the vector comprising the CAR sequence results in insertion of the CAR at an inhibitory gene locus, such as an exon of an inhibitory gene, in the immune cell, such that the CAR is under the control of the endogenous promoter of the inhibitory gene. In particular aspects, introducing the vector further disrupts expression of the inhibitory gene.

In another embodiment, there is provided an immune cell, such as an immune cell of the disclosed embodiments, with disrupted expression of at least two genes in the immune cell, produced at least by the step comprising introducing a CRISPR guide RNA (gRNA) for each gene to said immune cell, wherein at least two genes are selected from the group consisting of NKG2A, SIGLEC-7, LAG3, TIM3, CISH, FOXO1, TGFBR2, TIGIT, CD96, ADORA2, NR3C1, PD1, PDL-1, PDL-2, CD47, SIRPA, SHIP1, ADAM17, RPS6, 4EBP1, CD25, CD40, IL21R, ICAM1, CD95, CD80, CD86, IL10R, CD5, CD7, and a combination thereof. In some aspects, three, four, five, or six or more genes are disrupted.

In certain aspects, the immune cell is a T cell, NK cell, B cell, or stem cell. In some aspects, the immune cell is engineered to express a chimeric antigen receptor (CAR) and/or T cell receptor (TCR). The immune cell may be virus-specific, such as a virus-specific T cell. The T cell may be a regulatory T cell. The B cell may be a regulatory B cell. In some aspects, the stem cell is a mesenchymal stem cell (MSC) or an induced pluripotent stem (iPS) cell. In particular aspects, the T cell is a CD8+ T cell. CD4+ T cell, or gamma-delta T cell. The immune cell may be isolated from peripheral blood, cord blood, or bone marrow. In some aspects, the cord blood is pooled from 2 or more individual cord blood units.

In particular aspects, the method comprises disrupting particular groups of genes, such as NKG2A, CD47, TGFβR2, and CISH; NKG2A, CISH, TGFβR2 and ADORA2; NKG2A, TGFβR2 and CISH; TIGIT, CD96, CISH, and ADORA2; or ADAM17, TGFβR2 NKG2A and SHP1.

In some aspects, the disruption results in enhanced anti-tumor cytotoxicity, in vivo proliferation, in vivo persistence, and/or improved function of the immune cell. In particular aspects, the immune cell has increased secretion of IFN-γ, CD107, and/or TNFα. In some aspects, the immune cell has increased production of perforin and/or granzyme B.

In some aspects, the cell is engineered to express a CAR and/or TCR. The CAR may be inserted at an endogenous inhibitory gene locus of the cell, such as and inhibitory gene locus is selected from the group consisting of NKG2A, SIGLEC-7, LAG3, TIM3, CISH, FOXO1, TGFBR2, TIGIT, CD96, ADORA2, NR3C1, PD1, PDL-1, PDL-2, CD47, SIRPA, SHIP1, ADAM17, RPS6, 4EBP1, CD25, CD40, IL21R, ICAM1, CD95, CD80, CD86, IL10R, CD5, CD7, and a combination thereof. In some aspects, the CAR is under the control of the endogenous promoter of the inhibitory gene. In certain aspects, the CAR is inserted at the inhibitory gene locus by CRISPR-mediated gene editing.

In some aspects, the CAR comprises an antigen-binding domain selected from the group consisting of F(ab')2, Fab', Fab, Fv, and scFv. In certain aspects, the CAR targets one or more tumor associated antigens selected from the group consisting of CD19, CD319 (CS1), ROR1, CD20, carci-noembryonic antigen, alphafetoprotein, CA-125, MUC-1, epithelial tumor antigen, melanoma-associated antigen, mutated p53, mutated ras, HER2/Neu, ERBB2, folate bind-ing protein, HIV-1 envelope glycoprotein gp120, HIV-1 envelope glycoprotein gp41, GD2, CD5, CD123, CD23, CD30, CD56, c-Met, mesothelin, GD3, HERV-K, IL-11Ral-pha, kappa chain, lambda chain, CSPG4, ERBB2, WT-1, TRAIL/DR4, VEGFR2, CD33, CD47, CLL-1, U5snRNP200, CD200, BAFF-R, BCMA, CD99, and a combination thereof. In particular aspects, the CAR com-prises at least one signaling domain selected from the group consisting of CD3ξ, CD28, OX40/CD134, 4-1BB/CD137, FcεRIγ, ICOS/CD278, ILRB/CD122, IL-2RG/CD132, DAP12, CD70, CD40 and a combination thereof. In some aspects, the immune cell comprises one or more heterolo-gous cytokines, such as one or more of IL-7, IL-2, IL-15, IL-12, IL-18, and IL-21. In certain aspects, the CAR further comprises a suicide gene, such as a membrane bound nonsecretable TNF-alpha mutant or inducible caspase 9.

Further provided herein is an expression vector encoding at least one CAR and/or TCR, at least one inhibitory gene sequence, and at least one gRNA. In some aspects, the inhibitory gene sequence is from an inhibitory gene selected from the group consisting of NKG2A, SIGLEC-7, LAG3, TIM3, CISH, FOXO1, TGFBR2, TIGIT, CD96, ADORA2, NR3C1, PD1, PDL-1, PDL-2, CD47, SIRPA, SHIP1, ADAM17, RPS6, 4EBP1, CD25, CD40, IL21R, ICAM1, CD95, CD80, CD86, IL10R, CD5, and CD7. In particular aspects, the gRNA is specific to the inhibitory gene. In some aspects, the vector is a viral vector, such as an AAV vector. The CAR may be flanked by homology arms for the inhibitory gene. Also provided herein is a host cell, such as a cell of the embodiments, engineered to express the vector of the embodiments. In aspects, the cell is a T cell, NK cell, B cell, or stem cell.

Also provided herein is a pharmaceutical composition comprising a population of immune cells of the disclosed embodiments. Another embodiment provides a composition comprising a population of cells of the disclosed embodiments for the treatment of an immune-related disorder, infectious disease, and/or cancer.

In a further embodiment, there is provided a method of treating a disease or disorder in a subject comprising administering an effective amount of immune cells of the disclosed embodiments to the subject. In some aspects, the disease or disorder is an infectious disease, cancer, such as a solid cancer or a hematologic malignancy, or an immune-related disorder. The immune-related disorder may be an autoimmune disorder, graft versus host disease, allograft rejection, or inflammatory condition, for example. In some aspects, the immune-related disorder is an inflammatory condition and the immune cells have essentially no expression of glucocorticoid receptor. In certain aspects, the immune cells are autologous or allogeneic with respect to a recipient individual.

In additional aspects, the method further comprises administering at least a second therapeutic agent to the individual receiving the immune cells. In some aspects, the at least a second therapeutic agent comprises chemotherapy, immunotherapy, surgery, radiotherapy, hormone therapy, or biotherapy. In certain aspects, the immune cells and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion.

Another embodiment provides a method for engineering an immune cell to express a CAR comprising using a CRISPR gRNA to insert the CAR at an inhibitory gene locus of the immune cell. In some aspects, the CAR is encoded by an expression vector, such as a retroviral vector, plasmid, lentiviral vector, adenoviral vector, adenovirus-associated viral vector, and so forth. In certain aspects, the viral vector is an adenovirus-associated vector, such as AAV6.

In some aspects, the vector further comprises an inhibitory gene sequence, such as an inhibitory gene sequence is selected from the group consisting of NKG2A, SIGLEC-7, LAG3, TIM3, CISH, FOXO1, TGFBR2, TIGIT, CD96, ADORA2, NR3C1, PD1, PDL-1, PDL-2, CD47, SIRPA, SHIP1, ADAM17, RPS6, 4EBP1, CD25, CD40, IL21R, ICAM1, CD95, CD80, CD86, IL10R, CD5, CD7 and a combination thereof. In some aspects, the CRISPR gRNA is to the inhibitory gene. In certain aspects, the CAR is flanked by homology arms for the inhibitory gene. In particular aspects, the CAR is inserted at an inhibitory gene locus at any part of the gene, such as an exon of the inhibitory gene. The CAR may be under the control of the endogenous promoter of the inhibitory gene. In specific aspects, the CAR disrupts the expression of the inhibitory gene.

In some aspects, the CAR targets one or more tumor associated antigens selected from the group consisting of CD19, CD319 (CS1), ROR1, CD20, carcinoembryonic antigen, alphafetoprotein, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD5, CD123, CD23, CD30, CD56, c-Met, mesothelin, GD3, HERV-K, IL-11Ralpha, kappa chain, lambda chain, CSPG4, ERBB2, WT-1, TRAIL/DR4, VEGFR2, CD33, CD47, CLL-1, U5snRNP200, CD200, BAFF-R, BCMA, CD99, and a combination thereof. In particular aspects, the CAR comprises at least one signaling domain selected from the group consisting of CD3ξ, CD28, OX40/CD134, 4-1BB/CD137, FcεRIγ, ICOS/CD278, ILRB/CD122, IL-2RG/CD132, DAP12, CD70, and CD40. In some aspects, a vector that encodes the CAR also encodes a cytokine, such as IL-7, IL-2, IL-15, IL-12, IL-18, IL-21, or a combination thereof. In alternative cases, the cytokine is on a vector separate from the vector that encodes the CAR. In certain aspects, an expression construct that encodes the CAR further comprises a suicide gene, such as inducible caspase 9 or a membrane bound, nonsecretable TNF-alpha mutant.

Further provided herein is an immune cell with at least one CAR inserted at an inhibitory gene of the immune cell, such as an immune cell produced by the present methods. Also provided herein is a composition comprising a population of immune cells of embodiments of the disclosure, such as a population of T cells, B cells, NK cells, NK T cells, macrophages, stem cells, mixture thereof, and so forth.

Another embodiment provides a composition comprising a population of cells of the embodiments, and in certain embodiments the population is utilized for treatment of a medical condition of any kind, including at least for the treatment of an immune-related disorder, infectious disease, and/or cancer.

A further embodiment provides a method of treating a disease or disorder in a subject comprising administering an effective amount of immune cells of the embodiments to the subject. In some aspects, the disease or disorder is an infectious disease; cancer, such as a solid cancer or a hematologic malignancy; and/or an immune-related disorder. The immune-related disorder may be an autoimmune disorder, graft versus host disease, allograft rejection, and/or inflammatory condition, in some cases. In some aspects, the immune-related disorder is an inflammatory condition and the immune cells have essentially no expression of glucocorticoid receptor. In certain aspects, the immune cells are autologous or allogeneic with respect to a recipient individual.

In additional aspects, the method further comprises administering at least a second therapeutic agent to an individual. In some aspects, the at least a second therapeutic agent comprises chemotherapy, immunotherapy, surgery, radiotherapy, hormone therapy, or biotherapy. In certain aspects, the immune cells and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion. The immune cells and the at least a second therapeutic agent may be administered at the same time or at different times, and when they are administered at different times or at the same time but not in the same formulation, they may or may not be administered by the same route.

Other objects, features and advantages of the present disclosure will become apparent from the following detailed description. It should be understood, however, that the detailed description and the specific examples, while indicating particular embodiments of the disclosure, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 4A) The cytotoxic activity of gene edited NK cells vs Cas9 only NK cells was measured by $^{51}$Cr-release assay, against K562 (FIG. 4B) Following 30 minutes of recombinant TGF-B treatment (50 ng/ml) pSMAD activity was measured by flow cytometry. The addition of exogenous TGF-β failed to induce activation of pSMAD in the KO CAR-NK cells.

(FIG. 12A) Day 7 FACS-based NKG2A knockout efficiency. (FIG. 12B) Disruption of NKG2A in expanded NK cells leads to enhance antitumor efficacy. (FIG. 12C) Disruption of NKG2A in NK-CAR cells leads to enhanced antitumor efficacy against Raji targets.

DESCRIPTION OF ILLUSTRATIVE EMBODIMENTS

Figure 1:
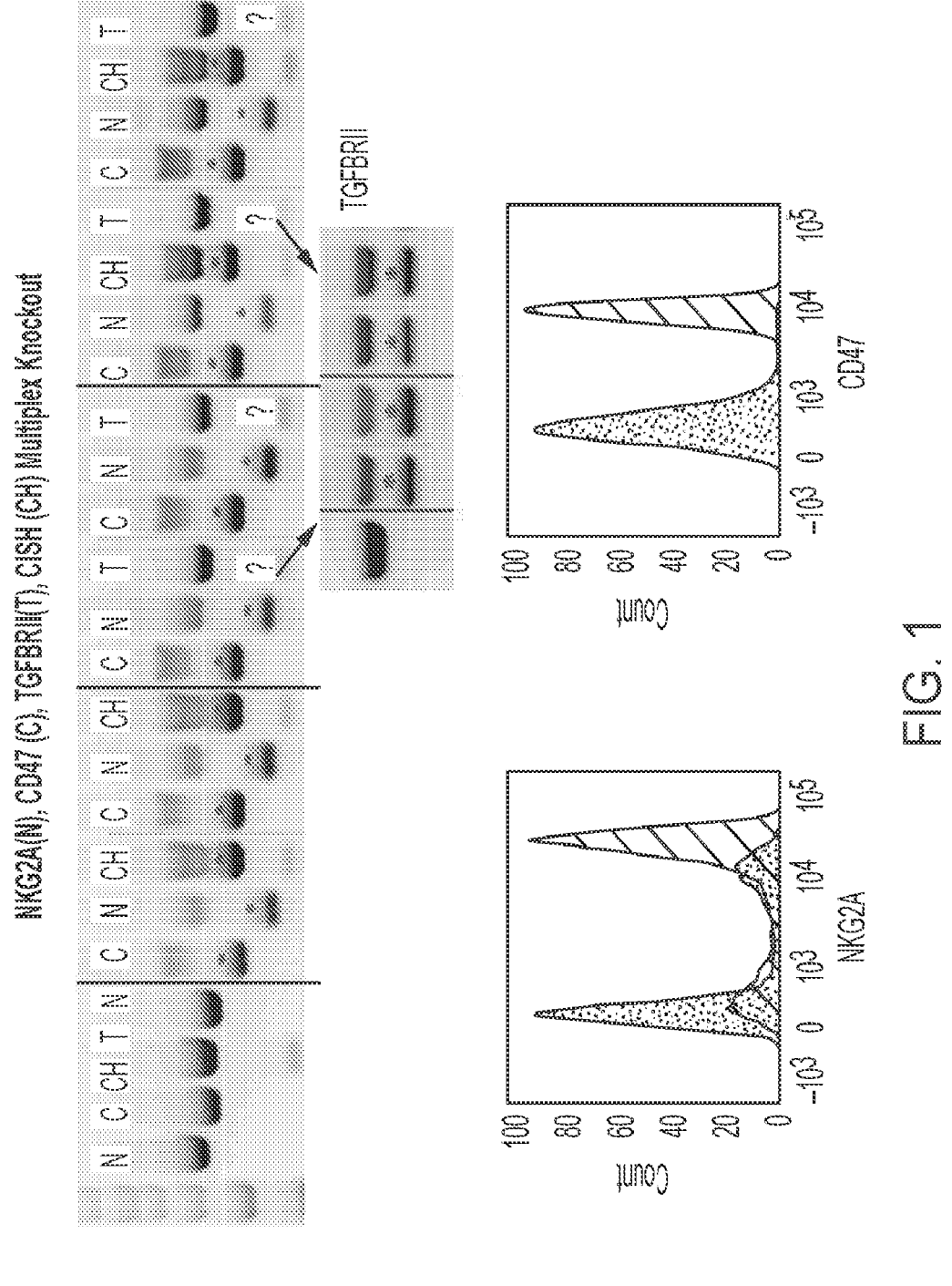
FIG. 1: CRISPR/Cas9 mediates efficient multiple genes (NKG2A, CD47, TGFBR2, and CISH) disruption in NK cells. In this set of genes, NKG2A and CD47 were knocked out in the first round of electroporation and in the second round of electroporation CISH and TGFBR2 were targeted. Knockout efficiency was successfully validated using PCR and flow-cytometry for both rounds of electroporation. The red (peaks on the right) and blue (peaks on the left) histograms in the flow panels represent expression of the protein before and after CRISPR KO, respectively.

In certain embodiments, the present disclosure provides a novel approach using CRISPR-Cas9 technology to simultaneously knockdown (or knockout) two or more genes (e.g., genes (such as those listed in Table 1, including adenosine 2a receptor, TGFβR2, NKG2A, TIGIT and/or CISH) in human immune cells (e.g., T cells, NK cells, CAR-transduced T cells, or CAR-transduced NK cells). The immune cells may be derived from peripheral blood or cord blood or a combination thereof.

The present studies demonstrated that decreased expression of these proteins correlates with improved function, in vivo proliferation and persistence, and cytotoxicity of T cells and NK cells. This strategy also protects T cells, NK cells, NK T cells, and iNKT cells from the immunosuppressive tumor microenvironment, which is mostly driven by TGFβ and adenosine. Thus, the present methods can be used to improve the efficacy of various adoptive cellular therapy products (e.g., NK cells, T cells, such as virus specific T cells and regulatory T cells, B cells, such as regulatory B cells, CAR-transduced NK cells, CAR-T cells and TCR engineered T and NK cells, iNKT cells, NKT cells). The adoptive cellular therapy products may be used to treat various diseases spanning from cancer (e.g., hematologic or solid malignancies), to infectious diseases and immune disorders, for example.

In particular embodiments, the immune cells express at least one CAR, and CAR engineering has seen multiple advances in the past few years. In fact, CAR-CD19 has shown impressive clinical results in patients with B cell leukemia and lymphoma, leading to the FDA approval in two CAR T products in the last year. While CAR-transduced T cells have been leading the way in the past few years, a panoply of pre-clinical studies as well as Phase I/II CAR NK trial led by the Applicants have also shown effectiveness of CAR-NK cells against cancer. Despite the advances in CAR engineering, CARs are still mostly transduced into T cells or NK cells using viral vectors, which randomly integrate in the cell's DNA and may result in clonal expansion, oncogenic transformation, altered transgene expression, or transcriptional silencing. Thus, finding a way to target the insertion of the CAR into a specific DNA locus would be valuable.

Accordingly, in one embodiment, the present disclosure provides methods for the insertion of a CAR at a specific gene locus, such as at the locus of an inhibitory gene or checkpoint protein, using CRISPR/Cas9. The insertion of the CAR at the gene locus can also be used to simultaneously disrupt expression of the gene, while optionally also bringing it under the control of the promoter of that gene, when desired. Specifically, the present methods may direct insertion of a CAR at the locus of an inhibitory gene, such as those listed in Table 1, including but not limited to NKG2A, CISH, PD-1, TIGIT, TIM3, SHP1, or TGFβR2, for example using an AAV6 vector and CRISPR/Cas9 technology. The insertion of the CAR at the inhibitory gene locus can disrupt the inhibitory effect of a checkpoint molecule (for example), while also allowing CAR expression to become under the regulation of the checkpoint promoter and upregulated in the tumor microenvironment. This is useful for the applications of CAR therapy in solid tumors, where upregulation of checkpoint molecules can negatively impact the success of CAR therapy. Thus, further methods are provided for producing adoptive cellular therapies, such as T cells, B cells, NK, NKT or iNKT cells, using the CAR insertion method that can have an increased safety profile.

I. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising", the words "a" or "an" may mean one or more than one. As used herein "another" may mean at least a second or more. Still further, the terms "having", "including", "containing" and "comprising" are interchangeable and one of skill in the art is cognizant that these terms are open ended terms. In specific embodiments, aspects of the disclosure may "consist essentially of" or "consist of" one or more sequences of the disclosure, for example. Some embodiments of the invention may consist of or consist essentially of one or more elements, method steps, and/or methods of the disclosure. It is contemplated that any method or composition described herein can be implemented with respect to any other method or composition described herein. The scope of the present application is not intended to be limited to the particular embodiments of the process, machine, manufacture, composition of matter, means, methods and steps described in the specification. As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

An "immune disorder," "immune-related disorder," or "immune-mediated disorder" refers to a disorder in which the immune response plays a key role in the development or progression of the disease. Immune-mediated disorders include autoimmune disorders, allograft rejection, graft versus host disease and inflammatory and allergic conditions.

An "immune response" is a response of a cell of the immune system, such as a B cell, or a T cell, or innate immune cell to a stimulus. In one embodiment, the response is specific for a particular antigen (an "antigen-specific response").

The term "inhibitory gene" as used herein refers to a gene whose gene product is directly or indirectly deleterious to the activity, proliferation, and/or persistence of one or more types of immune cells.

An "autoimmune disease" refers to a disease in which the immune system produces an immune response (for example, a B cell or a T cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces.

The term "engineered" as used herein refers to an entity that is generated by the hand of man, including a cell, nucleic acid, polypeptide, vector, and so forth. In at least some cases, an engineered entity is synthetic and comprises elements that are not naturally present or configured in the manner in which it is utilized in the disclosure.

"Treating" or treatment of a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

"Subject" and "patient" refer to either a human or non-human, such as primates, mammals, and vertebrates. In particular embodiments, the subject is a human.

As used herein, a "mammal" is an appropriate subject for the method of the present invention. A mammal may be any member of the higher vertebrate class Mammalia, including humans; characterized by live birth, body hair, and mammary glands in the female that secrete milk for feeding the young. Additionally, mammals are characterized by their ability to maintain a constant body temperature despite changing climatic conditions. Examples of mammals are humans, cats, dogs, cows, mice, rats, horses, goats, sheep, and chimpanzees. Mammals may be referred to as "patients" or "subjects" or "individuals".

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

As used herein, a "disruption" of a gene refers to the elimination or reduction of expression of one or more gene products encoded by the subject gene in a cell, compared to the level of expression of the gene product in the absence of the disruption. Exemplary gene products include mRNA and protein products encoded by the gene. Disruption in some cases is transient or reversible and in other cases is permanent. Disruption in some cases is of a functional or full length protein or mRNA, despite the fact that a truncated or non-functional product may be produced. In some embodiments herein, gene activity or function, as opposed to expression, is disrupted. Gene disruption is generally induced by artificial methods, i.e., by addition or introduction of a compound, molecule, complex, or composition, and/or by disruption of nucleic acid of or associated with the gene, such as at the DNA level. Exemplary methods for gene disruption include gene silencing, knockdown, knockout, and/or gene disruption techniques, such as gene editing. Examples include antisense technology, such as RNAi, siRNA, shRNA, and/or ribozymes, which generally result in transient reduction of expression, as well as gene editing techniques which result in targeted gene inactivation or disruption, e.g., by induction of breaks and/or homologous recombination. Examples include insertions, mutations, and deletions. The disruptions typically result in the repression and/or complete absence of expression of a normal or "wild type" product encoded by the gene. Exemplary of such gene disruptions are insertions, frameshift and mis sense mutations, deletions, knock-in, and knock-out of the gene or part of the gene, including deletions of the entire gene. Such disruptions can occur in the coding region, e.g., in one or more exons, resulting in the inability to produce a full-length product, functional product, or any product, such as by insertion of a stop codon. Such disruptions may also occur by disruptions in the promoter or enhancer or other region affecting activation of transcription, so as to prevent transcription of the gene. Gene disruptions include gene targeting, including targeted gene inactivation by homologous recombination.

II. Multiplex Gene Editing

In certain embodiments, the present disclosure concerns multiplex gene editing of any type of immune cells. CRISPR is one example that can be used to disrupt the expression of two or more genes, such as 3, 4, 5, 6, 7, 8, 9, 10, or more genes in an immune cell. The genes may be selected from the genes listed in Table 1, such as NK Cell Receptor A (NKG2A), Sialic Acid-Binding Ig-Like Lectin 7 (SIGLEC-7, CD328), Lymphocyte Activating 3 (LAG3), T-Cell Immunoglobulin Mucin Family Member 3 (TIM3, CD366, HAVCR2), Cytokine Inducible SH2-Containing Protein (CISH, CIS-1, SOCS), Forkhead Box O1 (FOXO1), Transforming Growth Factor Beta Receptor 2 (TGFβR2), T Cell Immunoreceptor With Ig And ITIM Domains (TIGIT), CD96, Adenosine Receptor 2A (ADORA2), Nuclear Receptor Subfamily 3 Group C Member 1 (NR3C1), Programmed Cell Death 1 (PD1), Programmed Cell Death 1 Ligand 1 (PDL-1), Programmed Cell Death 1 Ligand 2 (PDL-2), CD47, Signal Regulatory Protein Alpha (SIRPA), SH2

Domain-Containing Inositol 5-Phosphatase 1 (SHIP1), ADAM Metallopeptidase Domain 17 (ADAM17), Ribosomal Protein S6 (RPS6), Eukaryotic Translation Initiation Factor 4E Binding Protein 1 (4EBP1), CD25, CD40, Interleukin 21 Receptor (IL21R), Intercellular Adhesion Molecule 1 (ICAM1), CD95, CD80, CD86, Interleukin 21 Receptor (IL10R), CD5, CD7, or there may be other inhibitory genes. The gene editing allows for simultaneous disruption of expression of the multiple genes.

In some embodiments, the gene disruption is carried out by effecting a disruption in the gene, such as a knock-out, insertion, missense or frameshift mutation, such as biallelic frameshift mutation, deletion of all or part of the gene, e.g., one or more exons or portions therefore, and/or knock-in. For example, the disruption can be effected be sequence-specific or targeted nucleases, including DNA-binding targeted nucleases such as zinc finger nucleases (ZFN) and transcription activator-like effector nucleases (TALENs), and RNA-guided nucleases such as a CRISPR-associated nuclease (Cas), specifically designed to be targeted to the sequence of the gene or a portion thereof.

In some embodiments, the disruption is transient or reversible, such that expression of the gene is restored at a later time. In other embodiments, the disruption is not reversible or transient, e.g., is permanent.

In some embodiments, gene disruption is carried out by induction of one or more double-stranded breaks and/or one or more single-stranded breaks in the gene, typically in a targeted manner. In some embodiments, the double-stranded or single-stranded breaks are made by a nuclease, e.g., an endonuclease, such as a gene-targeted nuclease. In some aspects, the breaks are induced in the coding region of the gene, e.g., in an exon. For example, in some embodiments, the induction occurs near the N-terminal portion of the coding region, e.g., in the first exon, in the second exon, or in a subsequent exon.

The immune cell may be introduced to a guide RNA and CRISPR enzyme, or mRNA encoding the CRISPR enzyme. In some aspects, the cell is introduced to 1, 2, 3, 4, 5, or more guide RNAs simultaneously. For example, the cell may be introduced to 1, 2, or 3 guide RNAs during a first electroporation and then further introduced to 1, 2, or 3 additional guide RNAs during a second electroporation, and so forth.

In some embodiments, gene disruption is achieved using antisense techniques, such as by RNA interference (RNAi), short interfering RNA (siRNA), short hairpin (shRNA), and/or ribozymes are used to selectively suppress or repress expression of the gene. siRNA technology is RNAi that employs a double-stranded RNA molecule having a sequence homologous with the nucleotide sequence of mRNA that is transcribed from the gene, and a sequence complementary with the nucleotide sequence. siRNA generally is homologous/complementary with one region of mRNA that is transcribed from the gene, or may be siRNA including a plurality of RNA molecules that are homologous/complementary with different regions. In some aspects, the siRNA is comprised in a polycistronic construct.

In some embodiments, the disruption is achieved using a DNA-targeting molecule, such as a DNA-binding protein or DNA-binding nucleic acid, or complex, compound, or composition, containing the same, which specifically binds to or hybridizes to the gene. In some embodiments, the DNA-targeting molecule comprises a DNA-binding domain, e.g., a zinc finger protein (ZFP) DNA-binding domain, a transcription activator-like protein (TAL) or TAL effector (TALE) DNA-binding domain, a clustered regularly interspaced short palindromic repeats (CRISPR) DNA-binding domain, or a DNA-binding domain from a meganuclease. Zinc finger, TALE, and CRISPR system binding domains can be engineered to bind to a predetermined nucleotide sequence, for example via engineering (altering one or more amino acids) of the recognition helix region of a naturally occurring zinc finger or TALE protein. Engineered DNA binding proteins (zinc fingers or TALEs) are proteins that are non-naturally occurring. Rational criteria for design include application of substitution rules and computerized algorithms for processing information in a database storing information of existing ZFP and/or TALE designs and binding data.

For CRISPR-mediated disruption, the guide RNA and endonuclease may be introduced to the immune cells by any means known in the art to allow delivery inside cells or subcellular compartments, and agents/chemicals and/or molecules (proteins and nucleic acids) that can be used include liposomal delivery means, polymeric carriers, chemical carriers, lipoplexes, polyplexes, dendrimers, nanoparticles, emulsion, natural endocytosis or phagocytose pathway as non-limiting examples, as well as physical methods, such as electroporation. In specific aspects, electroporation is used to introduce the guide RNA and endonuclease, or nucleic acid encoding the endonuclease.

In one exemplary, specific method, the method for CRISPR knockout of multiple genes may comprise isolation of immune cells, such as NK cells, from cord blood or peripheral blood. The NK cells may be isolated and seeded on culture plates with irradiated feeder cells, such as at a 1:2 ratio, as one example. The cells can then be electroporated with gRNA and Cas9 in the presence of IL-2, such as at a concentration of 200 IU/mL. The media may be changed every other day, as one example. After 1-3 days, the NK cells are isolated to remove the feeder cells and can then be transduced with a CAR construct. The NK cells may then be subjected to a second CRISPR Cas9 knockout for additional gene(s). After the electroporation, the NK cells may be seeded with feeder cells, such as for 5-9 days.

TABLE 1

Genes for multiplex editing or CAR knock-in. Exemplary locations for knock-in are indicated.

| NK Cells, T cells, or MSC cells | |
| --- | --- |
| NKG2A | Exon 4 |
| SIGLEC-7 | Exon 1 |
| LAG3 | Exon 1 |
| TIM3 | Exon 2 |
| CISH | Exon 5 |
| FOXO1 | Exon 1 |
| TGFBR2 | Exon 5 |
| TIGIT | Exon 2 |
| CD96 | Exon 2 |
| ADORA2 | Exon 2 |
| NR3C1 | Exon 2 |
| PD1 | Exon 1 |
| PDL-1 | Exon 3 |
| PDL-2 | Exon 3 |
| CD47 | Exon 2 |
| SIRPA | Exon 2 |
| SHIP1 | Exon 1 |
| ADAM17 | Exon 1 |
| B2M | Exon 2 |
| CD16 | |
| B cells or T cells | |
| RPSS6 | Exon 2 |
| 4EBP1 | Exon 4 |
| CD25 | Exon 3 |

TABLE 1-continued

Genes for multiplex editing or CAR knock-in. Exemplary
locations for knock-in are indicated.

| | |
|---|---|
| CD40 | Exon 3 |
| IL21R | Exon 1 |
| ICAM1 | Exon 4 |
| CD95 | Exon 2 |
| CD80 | Exon 3 |
| CD86 | Exon 1 |
| IL10R | Exon 3 |
| CD5 | |
| CD7 | Exon 2 |

TABLE 2

Exemplary gRNA Sequences for
Gene Knockout.

| | |
|---|---|
| CISH (Exon 4) | AGGCCACATAGTGCTGCACA (gRNA1); SEQ ID NO: 1 |
| | TGTACAGCAGTGGCTGGTGG (gRNA2); SEQ ID NO: 2 |
| NKG2A (Exon 4) | AACAACTATCGTTACCACAG; SEQ ID NO: 3 |
| A2AR (Exon 3) | CTCCTCGGTGTACATCACGG (gRNA1); SEQ ID NO: 4 AGTAGTTGGTGACGTTCTGC (gRNA2); SEQ ID NO: 5 |
| TIGIT (Exon 3) | ACCCTGATGGGACGTACACT; SEQ ID NO: 6 |
| CD96 (Exon 2) | AGGCACAGTAGAAGCCGTAT; SEQ ID NO: 7 |
| TIM3 (Exon 2) | AGACGGGCACGAGGTTCCCT; SEQ ID NO: 8 |
| SHP1 (Exon 4) | TCACGCACAAGAAACGTCCA; SEQ ID NO: 9 |
| PD1 (Exon 2) | CCCCTTCGGTCACCACGAGC; SEQ ID NO: 10 |
| PDL1 (Exon 3) | ATTTACTGTCACGGTTCCCA; SEQ ID NO: 11 |
| PDL2 (Exon 3) | CCCCATAGATGATTATGCAT; SEQ ID NO: 12 |
| TGFBR2 (Exon 5) | GACGGCTGAGGAGCGGAAGA (gRNA1); SEQ ID NO: 13 |
| | TGTGGAGGTGAGCAATCCCC (gRNA2); SEQ ID NO: 14 |

In some embodiments, the immune cells of the present disclosure are modified to have altered expression of two or more genes. In some embodiments, the altered gene expression is carried out by effecting a disruption in the gene, such as a knock-out, insertion, missense or frameshift mutation, such as biallelic frameshift mutation, deletion of all or part of the gene, e.g., one or more exon or portion therefore, and/or knock-in. In specific embodiments, the altered gene expression can be effected by sequence-specific or targeted nucleases, including DNA-binding targeted nucleases such as RNA-guided nucleases such as a CRISPR-associated nuclease (Cas), specifically designed to be targeted to the sequence of the gene or a portion thereof.

In some embodiments, the alteration of the expression, activity, and/or function of the gene is carried out by disrupting the gene. In some aspects, the gene is modified so that its expression is reduced by at least at or about 10, 20, 30, or 40%, generally at least at or about 50, 60, 70, 80, 90, 91, 92, 93, 94, 95, 96, 97, 98, 99, or 100% as compared to the expression in the absence of the gene modification or in the absence of the components introduced to effect the modification.

In some embodiments, the alteration is transient or reversible, such that expression of the gene is restored at a later time if desired. In other embodiments, the alteration is not reversible or transient, e.g., is permanent.

In some embodiments, gene alteration is carried out by induction of one or more double-stranded breaks and/or one or more single-stranded breaks in the gene, typically in a targeted manner. In some embodiments, the double-stranded or single-stranded breaks are made by a nuclease, e.g. an endonuclease, such as a gene-targeted nuclease. In some aspects, the breaks are induced in the coding region of the gene, e.g. in an exon. For example, in some embodiments, the induction occurs near the N-terminal portion of the coding region, e.g. in the first exon, in the second exon, or in a subsequent exon.

In some aspects, the double-stranded or single-stranded breaks undergo repair via a cellular repair process, such as by non-homologous end-joining (NHEJ) or homology-directed repair (HDR). In some aspects, the repair process is error-prone and results in disruption of the gene, such as a frameshift mutation, e.g., biallelic frameshift mutation, which can result in complete knockout of the gene. For example, in some aspects, the disruption comprises inducing a deletion, mutation, and/or insertion. In some embodiments, the disruption results in the presence of an early stop codon. In some aspects, the presence of an insertion, deletion, translocation, frameshift mutation, and/or a premature stop codon results in disruption of the expression, activity, and/or function of the gene.

In some embodiments, the alteration is carried out using one or more DNA-binding nucleic acids, such as alteration via an RNA-guided endonuclease (RGEN). For example, the alteration can be carried out using clustered regularly interspaced short palindromic repeats (CRISPR) and CRISPR-associated (Cas) proteins. In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derive from a type I, type II, or type III CRISPR system, e.g., derived from a particular organism comprising an endogenous CRISPR system, such as *Streptococcus pyogenes*.

In some aspects, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the gRNA is targeted to the desired sequence by modifying the first 20, 19, 18, 17, 16, 15, 14, 14, 12, 11, or 10 nucleotides of the guide RNA to correspond to the target DNA sequence. In general, a CRISPR system is characterized by elements that promote the formation of a CRISPR complex at the site of a target sequence. Typically, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The CRISPR system can induce double stranded breaks (DSBs) at the target site, followed by disruptions or alterations as discussed herein. In other embodiments, Cas9 variants, deemed "nickases," are used to nick a single strand at the target site. Paired nickases can be used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor or activator, to affect gene expression.

The target sequence may comprise any polynucleotide, such as DNA or RNA polynucleotides. The target sequence may be located in the nucleus or cytoplasm of the cell, such as within an organelle of the cell. Generally, a sequence or template that may be used for recombination into the targeted locus comprising the target sequences is referred to as an "editing template" or "editing polynucleotide" or "editing sequence". In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. The tracr sequence has sufficient complementarity to a tracr mate sequence to hybridize and participate in formation of the CRISPR complex, such as at least 50%, 60%, 70%, 80%, 90%, 95% or 99% of sequence complementarity along the length of the tracr mate sequence when optimally aligned.

One or more vectors driving expression of one or more elements of the CRISPR system can be introduced into the cell such that expression of the elements of the CRISPR system direct formation of the CRISPR complex at one or more target sites. Components can also be delivered to cells as proteins and/or RNA. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. The vector may comprise one or more insertion sites, such as a restriction endonuclease recognition sequence (also referred to as a "cloning site"). In some embodiments, one or more insertion sites are located upstream and/or downstream of one or more sequence elements of one or more vectors. When multiple different guide sequences are used, a single expression construct may be used to target CRISPR activity to multiple different, corresponding target sequences within a cell.

A vector may comprise a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2.

The CRISPR enzyme can be Cas9 (e.g., from *S. pyogenes* or *S. pneumonia*). The CRISPR enzyme can direct cleavage of one or both strands at the location of a target sequence, such as within the target sequence and/or within the complement of the target sequence. The vector can encode a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (IIlumina, San Diego, Calif.), SOAP (available at soap.genomics.org.cn), and Maq (available at maq.sourceforge.net).

The CRISPR enzyme may be part of a fusion protein comprising one or more heterologous protein domains. A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CRISPR enzyme are described in US 20110059502, incorporated herein by reference.

III. Insertion of CAR and/or TCR at Inhibitory Gene Locus

In some embodiments, the present disclosure concerns the insertion of CAR and/or TCR at a specific gene locus of an immune cells. The CAR and/or TCR may be inserted at an inhibitory gene locus, such as a gene selected from the group consisting of NKG2A, Siglec 7, LAG3, TIM3, CISH, FOXO1, TGFBR2, TIGIT, CD96, Adenosine Receptor 2A, NR3C1, PD1, PDL-1, PDL-2, CD47, SIRPa, SHIP1, ADAM17, pS6, 4EBP1, CD25, CD40, IL21R, ICAM1, CD95, CD80, CD86, IL10R, CD5, CD7, and a combination thereof.

Inserting one or more CARs and/or TCRs in any of the methods disclosed herein can be site-specific. For example, one or more CARs and/or TCRs can be inserted adjacent to or near a promoter. In another example, one or more transgenes can be inserted adjacent to, near, or within an exon of a gene (e.g., an inhibitory gene). Such insertions can be used to knock-in a CAR and/or TCR while simultaneously disrupting expression of the gene. In another example, one or more CARs and/or TCRs can be inserted adjacent to, near, or within an intron of a gene. A CAR and/or TCR can be introduced by an adeno-associated viral (AAV) viral vector and integrate into a targeted genomic location. In some cases, a rAAV vector can be utilized to direct insertion of a transgene into a certain location. For example in some cases, a CAR and/or TCR can be integrated into at least a portion of a NKG2A, Siglec 7, LAG3, TIM3, CISH, FOXO1, TGFBR2, TIGIT, CD96, Adenosine Receptor 2A, NR3C1, PD1, PDL-1, PDL-2, CD47, SIRPa, SHIP1, ADAM17, pS6, 4EBP1, CD25, CD40, IL21R, ICAM1, CD95, CD80, CD86, IL10R, CD5, or CD7 gene by a rAAV or an AAV vector.

Modification of a targeted locus of a cell can be produced by introducing DNA into cells, where the DNA has homology to the target locus. DNA can include a marker gene, allowing for selection of cells comprising the integrated construct. Complementary DNA in a target vector can recombine with a chromosomal DNA at a target locus. A marker gene can be flanked by complementary DNA sequences, a 3' recombination arm, and a 5' recombination arm. Multiple loci within a cell can be targeted. For example, transgenes with recombination arms specific to 1 or more target loci can be introduced at once such that multiple genomic modifications occur in a single step. Homology arms can be about 0.2 kb to about 5 kb in length, such as from about 0.2 kb, 0.4 kb 0.6 kb, 0.8 kb, 1.0 kb, 1.2 kb, 1.4 kb, 1.6 kb, 1.8 kb, 2.0 kb, 2.2 kb, 2.4 kb, 2.6 kb, 2.8 kb, 3.0 kb, 3.2 kb, 3.4 kb, 3.6 kb, 3.8 kb, 4.0 kb, 4.2 kb, 4.4 kb, 4.6 kb, 4.8 kb, to about 5.0 kb in length, for example.

In one method, guide RNA can be designed to target a region of an inhibitory gene locus, such as the adjacent to the promoter, an exon, or intron of the gene. The guide RNA may targeting the 5' end of the an exon, such as the first, second, or third exon, of an inhibitory gene. The guide RNA may be comprise in an AAV vector repair matrix. The AAV vector may encode a self-cleaving 2A peptide, such as a P2A peptide, followed by the CAR cDNA. The CAR cassette and guide RNA sequence may be flanked by homology arms to the inhibitory gene. The immune cell may then be introduced to, such as electroporated with, the AAV vector and Cas9, such as Cas9 mRNA.

IV. Immune Cells

Certain embodiments of the present disclosure concern immune cells that are engineered to have knockout of multiple genes and/or to have knocking of a CAR at an inhibitory gene locus. The immune cells may be T cells (e.g., regulatory T cells, CD4+ T cells, CD8+ T cells, or gammadelta T cells), NK cells, invariant NK cells, NKT cells, B cells, stem cells (e.g., mesenchymal stem cells (MSCs) or induced pluripotent stem (iPSC) cells). The immune cells may be virus-specific, express a CAR, and/or express a TCR. In some embodiments, the cells are monocytes or granulocytes, e.g., myeloid cells, macrophages, neutrophils, dendritic cells, mast cells, eosinophils, and/or basophils. Also provided herein are methods of producing and engineering the immune cells as well as methods of using and administering the cells for adoptive cell therapy, in which case the cells may be autologous or allogeneic. Thus, the immune cells may be used as immunotherapy, such as to target cancer cells.

The immune cells may be isolated from subjects, particularly human subjects. The immune cells can be obtained from a subject of interest, such as a subject suspected of having a particular disease or condition, a subject suspected of having a predisposition to a particular disease or condition, or a subject who is undergoing therapy for a particular disease or condition. Immune cells can be collected from any location in which they reside in the subject including, but not limited to, blood, cord blood, spleen, thymus, lymph nodes, and bone marrow. The isolated immune cells may be used directly, or they can be stored for a period of time, such as by freezing.

The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors. In particular embodiments, the immune cells are isolated from blood, such as peripheral blood or cord blood or a mixture thereof. In some aspects, immune cells isolated from cord blood have enhanced immunomodulation capacity, such as measured by CD4-positive or CD8-positive T cell suppression. In specific aspects, the immune cells are isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

The population of immune cells can be obtained from a subject in need of therapy or suffering from a disease associated with reduced immune cell activity. Thus, the cells may be autologous to the subject in need of therapy. Alternatively, the population of immune cells can be obtained from a donor, preferably a histocompatibility matched donor. The immune cell population can be harvested from the peripheral blood, cord blood, bone marrow, spleen, or any other organ/tissue in which immune cells reside in the subject or donor. The immune cells can be isolated from a pool of subjects and/or donors, such as from pooled cord blood.

When the population of immune cells is obtained from a donor distinct from the subject, the donor is preferably allogeneic, provided the cells obtained are subject-compatible in that they can be introduced into the subject. Allogeneic donor cells are may or may not be human-leukocyte-antigen (HLA)-compatible.

A. T Cells

In some embodiments, the immune cells are T cells. Several basic approaches for the derivation, activation and expansion of functional anti-tumor effector cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods described herein.

In some embodiments, the T cells are derived from the blood, bone marrow, lymph, umbilical cord, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, CD4$^+$ cells, CD8$^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., CD4$^+$ and/or CD8$^+$ T cells) are naive T (T$_N$) cells, effector T cells (T$_{EFF}$), memory T cells and sub-types thereof, such as stem cell memory T (TSC$_M$), central memory T (TC$_M$), effector memory T (T$_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations.

In some embodiments, CD8$^+$ T cells are further enriched for or depleted of naive, central memory, effector memory, and/or central memory stem cells, such as by positive or negative selection based on surface antigens associated with the respective subpopulation. In some embodiments, enrichment for central memory T (T$_{CM}$) cells is carried out to increase efficacy, such as to improve long-term survival, expansion, and/or engraftment following administration, which in some aspects is particularly robust in such subpopulations.

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2).

The cultured T cells can be pooled and rapidly expanded. Rapid expansion provides an increase in the number of antigen-specific T-cells of at least about 50-fold (e.g., 50-, 60-, 70-, 80-, 90-, or 100-fold, or greater) over a period of about 10 to about 14 days. More preferably, rapid expansion provides an increase of at least about 200-fold (e.g., 200-, 300-, 400-, 500-, 600-, 700-, 800-, 900-, or greater) over a period of about 10 to about 14 days.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being preferred. The non-specific T-cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A2 (HLA-A2) binding peptide, in the presence of a T-cell growth factor, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2$^+$ allogeneic lymphocytes and IL-2, for example.

The autologous T cells can be modified to express a T cell growth factor that promotes the growth and activation of the autologous T cells. Suitable T cell growth factors include, for example, interleukin (IL)-2, IL-7, IL-15, and IL-12. Suitable methods of modification are known in the art. See, for instance, Sambrook et al., *Molecular Cloning: A Laboratory Manual, 3$^{rd}$* ed., Cold Spring Harbor Press, Cold Spring Harbor, N.Y. 2001; and Ausubel et al., *Current Protocols in Molecular Biology*, Greene Publishing Associates and John Wiley & Sons, N Y, 1994. In particular aspects, modified autologous T cells express the T cell growth factor at high levels. T cell growth factor coding sequences, such as that of IL-12, are readily available in the art, as are promoters, the operable linkage of which to a T cell growth factor coding sequence promote high-level expression.

B. NK Cells

In some embodiments, the immune cells are natural killer (NK) cells. NK cells are a subpopulation of lymphocytes that have spontaneous cytotoxicity against a variety of tumor cells, virus-infected cells, and some normal cells in the bone marrow and thymus. NK cells differentiate and mature in the bone marrow, lymph nodes, spleen, tonsils, and thymus. NK cells can be detected by specific surface markers, such as CD16, CD56, and CD8 in humans. NK cells do not express T cell antigen receptors, the pan T marker CD3, or surface immunoglobulin B cell receptors.

In certain embodiments, NK cells are derived from human peripheral blood mononuclear cells (PBMC), unstimulated leukapheresis products (PBSC), human embryonic stem cells (hESCs), induced pluripotent stem cells (iPSCs), bone marrow, or umbilical cord blood by methods well known in the art. Particularly, umbilical CB is used to derive NK cells. In certain aspects, the NK cells are isolated and expanded by the previously described method of ex vivo expansion of NK cells (Spanholtz et al., 2011; Shah et al., 2013). In this method, CB mononuclear cells are isolated by ficoll density gradient centrifugation and cultured in a bioreactor with IL-2 and artificial antigen presenting cells (aAPCs). After 7 days, the cell culture is depleted of any cells expressing CD3 and re-cultured for an additional 7 days. The cells are again CD3-depleted and characterized to determine the percentage of CD56$^+$/CD3$^-$ cells or NK cells. In other methods, umbilical CB is used to derive NK cells by the isolation of CD34$^+$ cells and differentiation into CD56$^+$/CD3$^-$ cells by culturing in medium contain SCF, IL-7, IL-15, and IL-2.

In specific embodiments, the NK cells are expanded at some point during their preparation. In specific cases, expansion of the NK cells comprises: stimulating mononuclear cells (MNCs) from cord blood in the presence of antigen presenting cells (APCs) and IL-2; and re-stimulating the cells with APCs to produce expanded NK cells, wherein in at least some cases the method is performed in a bioreactor. The stimulating step can direct the MNCs towards NK cells. The re-stimulating step may or may not comprise the presence of IL-2. In particular aspects, the method does not comprise removal or addition of any media components during a stimulating step. In particular aspects, the method is performed within a certain time frame, such as in less than 15 days, for example in 14 days.

In a certain embodiment, the NK cells are expanded by an ex vivo method for the expansion comprising: (a) obtaining a starting population of mononuclear cells (MNCs) from cord blood; (b) stimulating the MNCs in the presence of antigen presenting cells (APCs) and IL-2; and (c) re-stimulating the cells with APCs to produce expanded NK cells, wherein the method is performed in a bioreactor and is good manufacturing practice (GMP) compliant. The stimulating of step (b) can direct the MNCs towards NK cells. Step (c) may or may not comprise the presence of IL-2. In particular aspects, the method does not comprise removal or addition of any media components during step (b). In particular aspects, the method is performed in less than 15 days, such as in 14 days.

In some aspects, the method further comprises depleting cells positive for one or more particular markers, such as CD3, for example. In certain aspects, the depleting step is performed between steps (b) and (c). In some aspects, the cells are removed from the bioreactor for CD3 depletion and placed in the bioreactor for step (c).

In certain aspects, obtaining the starting population of MNCs from cord blood comprises thawing cord blood in the presence of dextran, human serum albumin (HSA), DNAse, and/or magnesium chloride. In particular aspects, obtaining the starting population of MNCs from cord blood comprises thawing cord blood in the presence of dextran and/or DNase. In specific aspects, the cord blood is washed in the presence of 5-20%, such as 10%, dextran. In certain aspects, the cord blood is suspended in the presence of magnesium chloride, such as at a concentration of 100-300 mM, particularly 200 mM. In some aspects, obtaining comprises performing ficoll density gradient centrifugation to obtain mononuclear cells (MNCs).

In certain aspects, the bioreactor is a gas permeable bioreactor. In particular aspects, the gas permeable bioreactor is G-Rex100M or G-Rex100. In some aspects, the stimulating of step (b) is performed in 3-5 L of media, such as 3, 3.5, 4, 4.5, or 5 L.

In some aspects, the APCs are gamma-irradiated. In certain aspects, the APCs are engineered to express membrane-bound IL-21 (mbIL-21). In particular aspects, the APCs are engineered to express IL-21, IL-15, and/or IL-2. In some aspects, the MNCs and APCs are cultured at a ratio of 1:2. In some aspects, the IL-2 is at a concentration of 50-200 IU/mL, such as 100 IU/mL. In particular aspects, the IL-2 is replenished every 2-3 days.

In particular aspects, step (b) is performed for 6-8 days, such as 7 days. In some aspects, step (c) is performed for 6-8 days, such as 7 days. In some aspects, step (c) does not comprise splitting of the cells. In particular aspects, the cells are fed twice with IL-2 during step (c), and in specific cases, no other media components are added or removed during step (c).

In some aspects, the method comprises the use of 3, 4, 5, or 6 bioreactors. In particular aspects, the method comprises the use of less than 10 bioreactors.

In specific aspects, the NK cells are expanded at least 500-fold, 800-fold, 1000-fold, 1200-fold, 1500-fold, 2000-fold, 2500-fold, 3000-fold, or 5000-fold. In particular aspects, culturing the NK cells in the bioreactor produces more than 1000-fold NK cells as compared to static liquid culture.

In certain aspects, the method does not comprise human leukocyte antigen (HLA) matching. In some aspects, the starting population of NK cells are not obtained from a haploidentical donor.

In some aspects, the expanded NK cells have enhanced anti-tumor activity as comprises to NK cells expanded from peripheral blood. In certain aspects, the expanded NK cells have higher expression of one or more cell cycle genes, one or more cell division genes, and/or one or more DNA replication genes, as compared to NK cells expanded from peripheral blood. In some aspects, the expanded NK cells have higher proliferative capacity as compared to NK cells expanded from peripheral blood. In some aspects, the expanded NK cells do not exhibit exhaustion. In certain aspects, exhaustion is detected by measuring expression of perforin, granzyme, CD57, KLRG1, and/or PD1. In some aspects, the expanded NK cells have high expression of perforin and/or granzyme. In certain aspects, the expanded NK cells have low or no expression of CD57, KLRG1, and/or PD1.

In some aspects, the expanded NK cells comprise a clinically relevant dose. In certain aspects, the cord blood is frozen cord blood. In particular aspects, the frozen cord blood has been tested for one or more infectious diseases, such as hepatitis A, hepatitis B, hepatitis C, *Trypanosoma cruzi*, HIV, Human T-Lymphotropic virus, syphyllis, Zika virus, and so forth. In some aspects, the cord blood is pooled cord blood, such as from 3, 4, 5, 6, 7, or 8 individual cord blood units.

In some aspects, the NK cells are not autologous, such as with respect to a recipient individual. In certain aspects, the NK cells are not allogeneic, such as with respect to a recipient individual.

In some aspects, the APCs are universal antigen presenting cells (uAPCs). In certain aspects, the uAPCs are engineered to express (1) CD48 and/or CS1 (CD319), (2) membrane-bound interleukin-21 (mbIL-21), and (3) 41BB ligand (41BBL). In some aspects, the uAPCs express CD48. In certain aspects, the uAPCs express CS1. In particular aspects, the uAPCs express CD48 and CS1. In some aspects, the uAPCs have essentially no expression of endogenous HLA class I, II, and/or CD1d molecules. In certain aspects, the uAPCs express ICAM-1 (CD54) and/or LFA-3 (CD58). In particular aspects, the uAPCs are further defined as leukemia cell-derived aAPCs, such as K562 cells.

C. Stem Cells

In some embodiments, the immune cells of the present disclosure may be stem cells, such as induced pluripotent stem cells (PSCs), mesenchymal stem cells (MSCs), or hematopoietic stem cells (HSCs).

The pluripotent stem cells used herein may be induced pluripotent stem (iPS) cells, commonly abbreviated iPS cells or iPSCs. With the exception of germ cells, any cell can be used as a starting point for iPSCs. For example, cell types could be keratinocytes, fibroblasts, hematopoietic cells, mesenchymal cells, liver cells, or stomach cells. There is no limitation on the degree of cell differentiation or the age of an animal from which cells are collected; even undifferentiated progenitor cells (including somatic stem cells) and finally differentiated mature cells can be used as sources of somatic cells in the methods disclosed herein.

Somatic cells can be reprogrammed to produce iPS cells using methods known to one of skill in the art. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 are utilized or Oct3/4, Sox2, Nanog, and Lin28.

Once derived, iPSCs can be cultured in a medium sufficient to maintain pluripotency. In certain embodiments, undefined conditions may be used; for example, pluripotent cells may be cultured on fibroblast feeder cells or a medium that has been exposed to fibroblast feeder cells in order to maintain the stem cells in an undifferentiated state. In some embodiments, the cell is cultured in the co-presence of mouse embryonic fibroblasts treated with radiation or an antibiotic to terminate the cell division, as feeder cells. Alternately, pluripotent cells may be cultured and maintained in an essentially undifferentiated state using a defined, feeder-independent culture system, such as a TESR™ medium or E8™/Essential 8™ medium.

V. Genetically Engineered Antigen Receptors

The immune cells of the present disclosure can be genetically engineered to express antigen receptors such as engineered TCRs, CARs, chimeric cytokine receptors, chemokine receptors, a combination thereof, and so on. For example, the immune cells are modified to express a CAR and/or TCR having antigenic specificity for a cancer antigen. Multiple CARs and/or TCRs, such as to different antigens, may be added to the immune cells. In some aspects, the immune cells are engineered to express the CAR or TCR by knock-in of the CAR or TCR at an inhibitory gene locus using CRISPR.

Suitable methods of modification are known in the art. See, for instance, Sambrook and Ausubel, supra. For example, the cells may be transduced to express a TCR having antigenic specificity for a cancer antigen using transduction techniques described in Heemskerk et al., 2008 and Johnson et al., 2009.

Electroporation of RNA coding for the full length TCR α and β (or γ and δ) chains can be used as alternative to overcome long-term problems with autoreactivity caused by pairing of retrovirally transduced and endogenous TCR chains. Even if such alternative pairing takes place in the transient transfection strategy, the possibly generated autore-active T cells will lose this autoreactivity after some time, because the introduced TCR α and β chain are only transiently expressed. When the introduced TCR α and β chain expression is diminished, only normal autologous T cells are left. This is not the case when full length TCR chains are introduced by stable retroviral transduction, which will never lose the introduced TCR chains, causing a constantly present autoreactivity in the patient.

In some embodiments, the cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

In some embodiments, the CAR contains an extracellular antigen-recognition domain that specifically binds to an antigen. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., 2013; Davila et al., 2013; Turtle et al., 2012; Wu et al., 2012. In some aspects, the genetically engineered antigen receptors include a CAR as described in U.S. Pat. No. 7,446,190, and those described in International Patent Application Publication No.: WO/2014055668 A1.

A. Chimeric Antigen Receptors

In some embodiments, the CAR comprises: a) one or more intracellular signaling domains, b) a transmembrane domain, and c) an extracellular domain comprising an antigen binding region.

In some embodiments, the engineered antigen receptors include CARs, including activating or stimulatory CARs, costimulatory CARs (see WO2014/055668), and/or inhibitory CARs (iCARs, see Fedorov et al., 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

Certain embodiments of the present disclosure concern the use of nucleic acids, including nucleic acids encoding an antigen-specific CAR polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprising the shared space between one or more antigens. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor.

It is contemplated that the human CAR nucleic acids may be human genes used to enhance cellular immunotherapy for human patients. In a specific embodiment, the invention includes a full-length CAR cDNA or coding region. The antigen binding regions or domain can comprise a fragment of the VH and VL chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, DAP12, and 4-1BB (CD137). In addition to a primary signal initiated by CD3ζ, an additional signal provided by a human costimulatory receptor inserted in a human CAR is important for full activation of NK cells and could help improve in vivo persistence and the therapeutic success of the adoptive immunotherapy.

In some embodiments, CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In certain embodiments of the chimeric antigen receptor, the antigen-specific portion of the receptor (which may be referred to as an extracellular domain comprising an antigen binding region) comprises a tumor associated antigen or a pathogen-specific antigen binding domain. Antigens include carbohydrate antigens recognized by pattern-recognition receptors, such as Dectin-1. A tumor associated antigen may be of any kind so long as it is expressed on the cell surface of tumor cells. Exemplary embodiments of tumor associated antigens include CD19, CD20, carcinoembryonic antigen, alphafetoprotein, CA-125, MUC-1, CD56, EGFR, c-Met, AKT, Her2, Her3, epithelial tumor antigen, melanoma-associated antigen, mutated p53, mutated ras, and so forth. In certain embodiments, the CAR may be co-expressed with a cytokine to improve persistence when there is a low amount of tumor-associated antigen. For example, CAR may be co-expressed with one or more cytokines, such as IL-7, IL-2, IL-15, IL-12, IL-18, IL-21, or a combination thereof.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into immune cells as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into immune cells. Suitable vectors for use in accordance with the method of the present disclosure are non-replicating in the immune cells. A large number of vectors are known that are based on viruses, where the copy number of the virus maintained in the cell is low enough to maintain the viability of the cell, such as, for example, vectors based on HIV, SV40, EBV, HSV, or BPV.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source.

Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 zeta, CD3 epsilon, CD3 gamma, CD3 delta, CD45, CD4, CD5, CD8, CD9, CD 16, CD22, CD33, CD37, CD64, CD80, CD86, CD 134, CD137, CD154, ICOS/CD278, GITR/CD357, NKG2D, and DAP molecules. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

In certain embodiments, the platform technologies disclosed herein to genetically modify immune cells, such as NK cells, comprise (i) non-viral gene transfer using an electroporation device (e.g., a nucleofector), (ii) CARs that signal through endodomains (e.g., CD28/CD3-ζ, CD137/CD3-ζ, or other combinations), (iii) CARs with variable lengths of extracellular domains connecting the antigen-recognition domain to the cell surface, and, in some cases, (iv) artificial antigen presenting cells (aAPC) derived from K562 to be able to robustly and numerically expand CAR$^+$ immune cells (Singh et al., 2008; Singh et al., 2011).

B. T Cell Receptor (TCR)

In some embodiments, the genetically engineered antigen receptors include recombinant TCRs and/or TCRs cloned from naturally occurring T cells. A "T cell receptor" or "TCR" refers to a molecule that contains a variable α and β chains (also known as TCRα and TCRβ, respectively) or a variable γ and δ chains (also known as TCRγ and TCRδ, respectively) and that is capable of specifically binding to an antigen peptide bound to a MHC receptor. In some embodiments, the TCR is in the αβ form.

Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable a chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., 1990; Chothia et al., 1988; Lefranc et al., 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., α-chain, β-chain) can contain two immunoglobulin domains, a variable domain (e.g., $V_a$ or Vp; typically amino acids 1 to 116 based on Kabat numbering Kabat et al., "Sequences of Proteins of Immunological Interest, US Dept. Health and Human Services, Public Health Service National Institutes of Health, 1991, $5^{th}$ ed.) at the N-terminus, and one constant domain (e.g., a-chain constant domain or $C_a$, typically amino acids 117 to 259 based on Kabat, β-chain constant domain or Cp, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T cell hybridomas or other publicly available source. In some embodiments, the T cells can be obtained from in vivo isolated cells. In some embodiments, a high-affinity T cell clone can be isolated from a patient, and the TCR isolated. In some embodiments, the T cells can be a cultured T cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al., 2009 and Cohen et al., 2005). In some embodiments, phage display is used to isolate TCRs against a target antigen (see, e.g., Varela-Rohena et al., 2008 and Li, 2005). In some embodiments, the TCR or antigen-binding portion thereof can be synthetically generated from knowledge of the sequence of the TCR.

C. Antigen-Presenting Cells

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane. The MHC is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

In some cases, aAPCs are useful in preparing therapeutic compositions and cell therapy products of the embodiments. For general guidance regarding the preparation and use of antigen-presenting systems, see, e.g., U.S. Pat. Nos. 6,225, 042, 6,355,479, 6,362,001 and 6,790,662; U.S. Patent Application Publication Nos. 2009/0017000 and 2009/0004142; and International Publication No. WO2007/103009.

aAPC systems may comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD86, CD64 (FcγRI), 41BB ligand, and IL-21. Adhesion molecules may include carbohydrate-binding glycoproteins such as selectins, transmembrane binding glycoproteins such as integrins, calcium-dependent proteins such as cadherins, and singlepass transmembrane immunoglobulin (Ig) superfamily proteins, such as intercellular adhesion molecules (ICAMs), which promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

D. Antigens

Among the antigens targeted by the genetically engineered antigen receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

Any suitable antigen may be targeted in the present method. The antigen may be associated with certain cancer cells but not associated with non-cancerous cells, in some cases. Exemplary antigens include, but are not limited to, antigenic molecules from infectious agents, auto-/self-antigens, tumor-/cancer-associated antigens, and tumor neoantigens (Linnemann et al., 2015). In particular aspects, the antigens include NY-ESO, EGFRvIII, Muc-1, Her2, CA-125, WT-1, Mage-A3, Mage-A4, Mage-A10, TRAIL/DR4, and CEA. In particular aspects, the antigens for the two or more antigen receptors include, but are not limited to, CD19, EBNA, WT1, CD123, NY-ESO, EGFRvIII, MUC1, HER2, CA-125, WT1, Mage-A3, Mage-A4, Mage-A10, TRAIL/DR4, and/or CEA. The sequences for these antigens are known in the art, for example, in the GenBank® database: CD19 (Accession No. NG_007275.1), EBNA (Accession No. NG_002392.2), WT1 (Accession No. NG_009272.1), CD123 (Accession No. NC_000023.11), NY-ESO (Accession No. NC_000023.11), EGFRvIII (Accession No. NG_007726.3), MUC1 (Accession No. NG_029383.1), HER2 (Accession No. NG_007503.1), CA-125 (Accession No. NG_055257.1), WT1 (Accession No. NG_009272.1), Mage-A3 (Accession No. NG_013244.1), Mage-A4 (Accession No. NG_013245.1), Mage-A10 (Accession No. NC_000023.11), TRAIL/DR4 (Accession No. NC_000003.12), and/or CEA (Accession No. NC_000019.10).

Tumor-associated antigens may be derived from prostate, breast, colorectal, lung, pancreatic, renal, mesothelioma, ovarian, liver, brain, bone, stomach, spleen, testicular, cervical, anal, gall bladder, thyroid, or melanoma cancers, as examples. Exemplary tumor-associated antigens or tumor cell-derived antigens include MAGE 1, 3, and MAGE 4 (or other MAGE antigens such as those disclosed in International Patent Publication No. WO 99/40188); PRAME; BAGE; RAGE, Lage (also known as NY ESO 1); SAGE; and HAGE or GAGE. These non-limiting examples of tumor antigens are expressed in a wide range of tumor types such as melanoma, lung carcinoma, sarcoma, and bladder carcinoma. See, e.g., U.S. Pat. No. 6,544,518. Prostate cancer tumor-associated antigens include, for example, prostate specific membrane antigen (PSMA), prostate-specific antigen (PSA), prostatic acid phosphates, NKX3.1, and six-transmembrane epithelial antigen of the prostate (STEAP).

Other tumor associated antigens include Plu-1, HASH-1, HasH-2, Cripto and Criptin. Additionally, a tumor antigen may be a self-peptide hormone, such as whole length gonadotrophin hormone releasing hormone (GnRH), a short 10 amino acid long peptide, useful in the treatment of many cancers.

Tumor antigens include tumor antigens derived from cancers that are characterized by tumor-associated antigen expression, such as HER-2/neu expression. Tumor-associated antigens of interest include lineage-specific tumor antigens such as the melanocyte-melanoma lineage antigens MART-1/Melan-A, gp100, gp75, mda-7, tyrosinase and tyrosinase-related protein. Illustrative tumor-associated antigens include, but are not limited to, tumor antigens derived from or comprising any one or more of, p53, Ras, c-Myc, cytoplasmic serine/threonine kinases (e.g., A-Raf, B-Raf, and C-Raf, cyclin-dependent kinases), MAGE-A1, MAGE-A2, MAGE-A3, MAGE-A4, MAGE-A6, MAGE-A10, MAGE-A12, MART-1, BAGE, DAM-6, -10, GAGE-1, -2, -8, GAGE-3, -4, -5, -6, -7B, NA88-A, MART-1, MC1R, Gp100, PSA, PSM, Tyrosinase, TRP-1, TRP-2, ART-4, CAMEL, CEA, Cyp-B, hTERT, hTRT, iCE, MUC1, MUC2, Phosphoinositide 3-kinases (PI3Ks), TRK receptors, PRAME, P15, RU1, RU2, SART-1, SART-3, Wilms' tumor antigen (WT1), AFP, -catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD1) TACSTD2, receptor tyrosine kinases (e.g., Epidermal Growth Factor receptor (EGFR) (in particular, EGFRvIII), platelet derived growth factor receptor (PDGFR), vascular endothelial growth factor receptor (VEGFR)), cytoplasmic tyrosine kinases (e.g., src-family, syk-ZAP70 family), integrin-linked kinase (ILK), signal transducers and activators of transcription STAT3, STAT5, and STATE, hypoxia inducible factors (e.g., HIF-1 and HIF-2), Nuclear Factor-Kappa B (NF-B), Notch receptors (e.g., Notch1-4), c-Met, mammalian targets of rapamycin (mTOR), WNT, extracellular signal-regulated kinases (ERKs), and their regulatory subunits, PMSA, PR-3, MDM2, Mesothelin, renal cell carcinoma-5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGsS, SART3, STn, PAXS, OY-TES1, sperm protein 17, LCK, HMWMAA, AKAP-4, SSX2, XAGE 1, B7H3, legumain, TIE2, Page4, MAD-CT-1, FAP, MAD-CT-2, fos related antigen 1, CBX2, CLDN6, SPANX, TPTE, ACTL8, ANKRD30A, CDKN2A, MAD2L1, CTAG1B, SUNC1, LRRN1 and idiotype.

Antigens may include epitopic regions or epitopic peptides derived from genes mutated in tumor cells or from genes transcribed at different levels in tumor cells compared to normal cells, such as telomerase enzyme, survivin, mesothelin, mutated ras, bcr/abl rearrangement, Her2/neu, mutated or wild-type p53, cytochrome P450 1B 1, and abnormally expressed intron sequences such as N-acetyl-glucosaminyltransferase-V; clonal rearrangements of immunoglobulin genes generating unique idiotypes in myeloma and B-cell lymphomas; tumor antigens that include epitopic regions or epitopic peptides derived from oncoviral processes, such as human papilloma virus proteins E6 and E7; Epstein bar virus protein LMP2; nonmutated oncofetal proteins with a tumor-selective expression, such as carcinoembryonic antigen and alpha-fetoprotein.

In other embodiments, an antigen is obtained or derived from a pathogenic microorganism or from an opportunistic pathogenic microorganism (also called herein an infectious disease microorganism), such as a virus, fungus, parasite, and bacterium. In certain embodiments, antigens derived from such a microorganism include full-length proteins.

Illustrative pathogenic organisms whose antigens are contemplated for use in the method described herein include human immunodeficiency virus (HIV), herpes simplex virus (HSV), respiratory syncytial virus (RSV), cytomegalovirus (CMV), Epstein-Barr virus (EBV), Influenza A, B, and C, vesicular stomatitis virus (VSV), vesicular stomatitis virus (VSV), polyomavirus (e.g., BK virus and JC virus), adenovirus, *Staphylococcus* species including Methicillin-resistant *Staphylococcus aureus* (MRSA), and *Streptococcus* species including *Streptococcus pneumoniae*. As would be understood by the skilled person, proteins derived from these and other pathogenic microorganisms for use as antigen as described herein and nucleotide sequences encoding the proteins may be identified in publications and in public databases such as GENBANK®, SWISS-PROT®, and TREMBL®.

Antigens derived from human immunodeficiency virus (HIV) include any of the HIV virion structural proteins (e.g., gp120, gp41, p17, p24), protease, reverse transcriptase, or HIV proteins encoded by tat, rev, nef, vif, vpr and vpu.

Antigens derived from herpes simplex virus (e.g., HSV 1 and HSV2) include, but are not limited to, proteins expressed from HSV late genes. The late group of genes predominantly encodes proteins that form the virion particle. Such proteins include the five proteins from (UL) which form the viral capsid: UL6, UL18, UL35, UL38 and the major capsid protein UL19, UL45, and UL27, each of which may be used as an antigen as described herein. Other illustrative HSV proteins contemplated for use as antigens herein include the ICP27 (H1, H2), glycoprotein B (gB) and glycoprotein D (gD) proteins. The HSV genome comprises at least 74 genes, each encoding a protein that could potentially be used as an antigen.

Antigens derived from cytomegalovirus (CMV) include CMV structural proteins, viral antigens expressed during the immediate early and early phases of virus replication, glycoproteins I and III, capsid protein, coat protein, lower matrix protein pp65 (ppUL83), p52 (ppUL44), IE1 and IE2 (UL123 and UL122), protein products from the cluster of genes from UL128-UL150 (Rykman, et al., 2006), envelope glycoprotein B (gB), gH, gN, and pp150. As would be understood by the skilled person, CMV proteins for use as antigens described herein may be identified in public databases such as GENBANK®, SWISS-PROT®, and TREMBL® (see e.g., Bennekov et al., 2004; Loewendorf et al., 2010; Marschall et al., 2009).

Antigens derived from Epstein-Ban virus (EBV) that are contemplated for use in certain embodiments include EBV lytic proteins gp350 and gp110, EBV proteins produced during latent cycle infection including Epstein-Ban nuclear antigen (EBNA)-1, EBNA-2, EBNA-3A, EBNA-3B, EBNA-3C, EBNA-leader protein (EBNA-LP) and latent membrane proteins (LMP)-1, LMP-2A and LMP-2B (see, e.g., Lockey et al., 2008).

Antigens derived from respiratory syncytial virus (RSV) that are contemplated for use herein include any of the eleven proteins encoded by the RSV genome, or antigenic fragments thereof: NS 1, NS2, N (nucleocapsid protein), M (Matrix protein) SH, G and F (viral coat proteins), M2 (second matrix protein), M2-1 (elongation factor), M2-2 (transcription regulation), RNA polymerase, and phosphoprotein P.

Antigens derived from Vesicular stomatitis virus (VSV) that are contemplated for use include any one of the five major proteins encoded by the VSV genome, and antigenic fragments thereof: large protein (L), glycoprotein (G), nucleoprotein (N), phosphoprotein (P), and matrix protein (M) (see, e.g., Rieder et al., 1999).

Antigens derived from an influenza virus that are contemplated for use in certain embodiments include hemagglutinin (HA), neuraminidase (NA), nucleoprotein (NP), matrix proteins M1 and M2, NS1, NS2 (NEP), PA, PB1, PB1-F2, and PB2.

Exemplary viral antigens also include, but are not limited to, adenovirus polypeptides, alphavirus polypeptides, calicivirus polypeptides (e.g., a calicivirus capsid antigen), coronavirus polypeptides, distemper virus polypeptides, Ebola virus polypeptides, enterovirus polypeptides, flavivirus polypeptides, hepatitis virus (AE) polypeptides (a hepatitis B core or surface antigen, a hepatitis C virus E1 or E2 glycoproteins, core, or non-structural proteins), herpesvirus polypeptides (including a herpes simplex virus or varicella zoster virus glycoprotein), infectious peritonitis virus polypeptides, leukemia virus polypeptides, Marburg virus polypeptides, orthomyxovirus polypeptides, papilloma virus polypeptides, parainfluenza virus polypeptides (e.g., the hemagglutinin and neuraminidase polypeptides), paramyxovirus polypeptides, parvovirus polypeptides, pestivirus polypeptides, picorna virus polypeptides (e.g., a poliovirus capsid polypeptide), pox virus polypeptides (e.g., a vaccinia virus polypeptide), rabies virus polypeptides (e.g., a rabies virus glycoprotein G), reovirus polypeptides, retrovirus polypeptides, and rotavirus polypeptides.

In certain embodiments, the antigen may be bacterial antigens. In certain embodiments, a bacterial antigen of interest may be a secreted polypeptide. In other certain embodiments, bacterial antigens include antigens that have a portion or portions of the polypeptide exposed on the outer cell surface of the bacteria.

Antigens derived from *Staphylococcus* species including Methicillin-resistant *Staphylococcus aureus* (MRSA) that are contemplated for use include virulence regulators, such as the Agr system, Sar and Sae, the Arl system, Sar homologues (Rot, MgrA, SarS, SarR, SarT, SarU, SarV, SarX, SarZ and TcaR), the Srr system and TRAP. Other *Staphylococcus* proteins that may serve as antigens include Clp proteins, HtrA, MsrR, aconitase, CcpA, SvrA, Msa, CfvA and CfvB (see, e.g., *Staphylococcus*: Molecular Genetics, 2008 Caister Academic Press, Ed. Jodi Lindsay). The genomes for two species of *Staphylococcus aureus* (N315 and Mu50) have been sequenced and are publicly available, for example at PATRIC (PATRIC: The VBI PathoSystems Resource Integration Center, Snyder et al., 2007). As would be understood by the skilled person, *Staphylococcus* proteins for use as antigens may also be identified in other public databases such as GenBank®, Swiss-Prot®, and TrEMBL®.

Antigens derived from *Streptococcus pneumoniae* that are contemplated for use in certain embodiments described herein include pneumolysin, PspA, choline-binding protein A (CbpA), NanA, NanB, SpnHL, PavA, LytA, Pht, and pilin proteins (RrgA; RrgB; RrgC). Antigenic proteins of *Streptococcus pneumoniae* are also known in the art and may be used as an antigen in some embodiments (see, e.g., Zysk et al., 2000). The complete genome sequence of a virulent strain of *Streptococcus pneumoniae* has been sequenced and, as would be understood by the skilled person, *S. pneumoniae* proteins for use herein may also be identified in other public databases such as GENBANK®, SWISS-PROT®, and TREMBL®. Proteins of particular interest for antigens according to the present disclosure include virulence factors and proteins predicted to be exposed at the surface of the pneumococci (see, e.g., Frolet et al., 2010).

Examples of bacterial antigens that may be used as antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides (e.g., *B. burgdorferi* OspA), *Brucella* polypeptides, *Campylobacter* polypeptides, *Capnocytophaga* polypeptides, *Chlamydia* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides (e.g., *H. influenzae* type b outer membrane protein), *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides (i.e., *S. pneumoniae* polypeptides) (see description herein), *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, group A streptococcus polypeptides (e.g., *S. pyogenes* M proteins), group B *Streptococcus* (*S. agalactiae*) polypeptides, *Treponema* polypeptides, and *Yersinia* polypeptides (e.g., *Y pestis* F1 and V antigens).

Examples of fungal antigens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammon-*

*dia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides. Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides. (e.g., *P. falciparum* circumsporozoite (PfCSP)), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of ectoparasite antigens include, but are not limited to, polypeptides (including antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

E. Suicide Genes

In some cases, any cells of the disclosure are modified to produce one or more agents other than heterologous cytokines, engineered receptors, and so forth. In specific embodiments, the cells, such as NK cells, are engineered to harbor one or more suicide genes, and the term "suicide gene" as used herein is defined as a gene which, upon administration of a prodrug, effects transition of a gene product to a compound which kills its host cell. In some cases, the NK cell therapy may be subject to utilization of one or more suicide genes of any kind when an individual receiving the NK cell therapy and/or having received the NK cell therapy shows one or more symptoms of one or more adverse events, such as cytokine release syndrome, neurotoxicity, anaphylaxis/allergy, and/or on-target/off tumor toxicities (as examples) or is considered at risk for having the one or more symptoms, including imminently. The use of the suicide gene may be part of a planned protocol for a therapy or may be used only upon a recognized need for its use. In some cases the cell therapy is terminated by use of agent(s) that targets the suicide gene or a gene product therefrom because the therapy is no longer required.

Examples of suicide genes include engineered nonsecretable (including membrane bound) tumor necrosis factor (TNF)-alpha mutant polypeptides (see PCT/US19/62009, which is incorporated by reference herein in its entirety), and they may be targeted by delivery of an antibody that binds the TNF-alpha mutant. Examples of suicide gene/prodrug combinations that may be used are Herpes Simplex Virus-thymidine kinase (HSV-tk) and ganciclovir, acyclovir, or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside. The *E. coli* purine nucleoside phosphorylase, a so-called suicide gene that converts the prodrug 6-methylpurine deoxyriboside to toxic purine 6-methylpurine, may be utilized. Other suicide genes include CD20, CD52, inducible caspase 9, purine nucleoside phosphorylase (PNP), Cytochrome p450 enzymes (CYP), Carboxypeptidases (CP), Carboxylesterase (CE), Nitroreductase (NTR), Guanine Ribosyltransferase (XGRTP), Glycosidase enzymes, Methionine-α,γ-lyase (MET), and Thymidine phosphorylase (TP), as examples.

F. Methods of Delivery

One of skill in the art would be well-equipped to construct a vector through standard recombinant techniques (see, for example, Sambrook et al., 2001 and Ausubel et al., 1996, both incorporated herein by reference) for the expression of the antigen receptors of the present disclosure. Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors, parvovirus vectors, polio virus vectors, vesicular stomatitis virus vectors, maraba virus vectors and group B adenovirus enadenotucirev vectors.

In specific embodiments, the vector is a multicistronic vector, such as is described in PCT/US19/62014, which is incorporated by reference herein in its entirety. In such cases, a single vector may encode the CAR or TCR (and the expression construct may be configured in a modular format to allow for interchanging parts of the CAR or TCR), a suicide gene, and one or more cytokines.

a. Viral Vectors

Viral vectors encoding an antigen receptor may be provided in certain aspects of the present disclosure. In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor mediated-endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present invention are described below.

Lentiviruses are complex retroviruses, which, in addition to the common retroviral genes gag, pol, and env, contain other genes with regulatory or structural function. Lentiviral vectors are well known in the art (see, for example, U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

b. Regulatory Elements

Expression cassettes included in vectors useful in the present disclosure in particular contain (in a 5'-to-3' direction) a eukaryotic transcriptional promoter operably linked to a protein-coding sequence, splice signals including intervening sequences, and a transcriptional termination/polyadenylation sequence. The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation. A promoter used in the context of the present disclosure includes constitutive, inducible, and tissue-specific promoters.

(i) Promoter/Enhancers

The expression constructs provided herein comprise a promoter to drive expression of the antigen receptor. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30110 bp-upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the βlactamase (penicillinase), lactose and tryptophan (trp-) promoter systems. In addition to producing nucleic acid sequences of promoters and enhancers synthetically, sequences may be produced using recombinant cloning and/or nucleic acid amplification technology, including PCR™, in connection with the compositions disclosed herein. Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally, any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e. g., beta actin promoter, GADPH promoter, metallothionein promoter; and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at GenBank® Accession No. X05244, nucleotide 283-341) or a mouse mammary tumor promoter (available from the ATCC, Cat. No. ATCC 45007). In certain embodiments, the promoter is CMV IE, dectin-1, dectin-2, human CD11c, F4/80, SM22, RSV, SV40, Ad MLP, beta-actin, MHC class I or MHC class II promoter, however any other promoter that is useful to drive expression of the therapeutic gene is applicable to the practice of the present disclosure.

In certain aspects, methods of the disclosure also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

(ii) Initiation Signals and Linked Expression

A specific initiation signal also may be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Additionally, certain 2A sequence elements could be used to create linked- or co-expression of genes in the constructs provided in the present disclosure. For example, cleavage sequences could be used to co-express genes by linking open reading frames to form a single cistron. An exemplary cleavage sequence is the F2A (Foot-and-mouth disease virus 2A) or a "2A-like" sequence (e.g., Thosea asigna virus 2A; T2A).

(iii) Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extrachromosomally replicating virus as described above or an autonomously replicating sequence (ARS) can be employed.

c. Selection and Screenable Markers

In some embodiments, cells containing a construct of the present disclosure may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

d. Other Methods of Nucleic Acid Delivery

In addition to viral delivery of the nucleic acids encoding the antigen receptor, the following are additional methods of recombinant gene delivery to a given host cell and are thus considered in the present disclosure.

Introduction of a nucleic acid, such as DNA or RNA, into the immune cells of the current disclosure may use any suitable methods for nucleic acid delivery for transformation of a cell, as described herein or as would be known to one of ordinary skill in the art. Such methods include, but are not limited to, direct delivery of DNA such as by ex vivo transfection, by injection, including microinjection); by electroporation; by calcium phosphate precipitation; by using DEAE-dextran followed by polyethylene glycol; by direct sonic loading; by liposome mediated transfection and receptor-mediated transfection; by microprojectile bombardment; by agitation with silicon carbide fibers; by *Agrobacterium*-mediated transformation; by desiccation/inhibition-mediated DNA uptake, and any combination of such methods. Through the application of techniques such as these, organelle(s), cell(s), tissue(s) or organism(s) may be stably or transiently transformed.

VI. Methods of Treatment

Embodiments of the disclosure include methods of treating an individual for cancer, infections of any kind, and any immune disorder. The individual may utilize the treatment method of the disclosure as an initial treatment or after another treatment or during another treatment. The immunotherapy methods may be tailored to the need of an individual with cancer based on the type or stage of cancer, and in at least some cases the immunotherapy may be modified during the course of treatment for the individual.

In specific cases, the treatment methods are as follows: 1) Adoptive cellular therapy with T or NK cells (ex vivo expanded or expressing CARs or TCRs) to treat cancer patients with any type of hematologic malignancy, (2) Adoptive cellular therapy with T or NK cells (ex vivo expanded or expressing CARs or TCRs) to treat cancer patients with any type of solid cancers, (3) Adoptive cellular therapy (ex vivo expanded or expressing CARs or TCRs) with Tregs and regulatory B cells to treat patients with immune disorders, (4) Adoptive cellular therapy with T or NK cells (ex vivo expanded or expressing CARs or TCRs)

to treat patients with infectious diseases. The present disclosure is the first to show that knocking down/out multiple genes in human NK cells contributes to the cell's improved functionality and resistance to tumor microenvironment. In specific embodiments, this has direct implications on patient care using a novel immunotherapeutic approach that enhances the function of a patient's own immune cells or adoptively transferred immune cells. Embodiments provide a novel approach to produce highly functional T, NK and B cells (both ex vivo expanded and CAR or TCR engineered) for immunotherapy. These include targeting cancers—both hematologic and solid tumors—(NK cells and T cells, also CAR T cells and CAR NK cells), autoimmune and alloimmune disorders (B cells, regulatory B cells and regulatory T cells) and treatment of infections (for pathogen-specific T cells).

In some embodiments, the present disclosure provides methods for immunotherapy comprising administering an effective amount of the immune cells of the present disclosure. In one embodiment, a medical disease or disorder is treated by transfer of immune NK cell population that elicits an immune response. In certain embodiments of the present disclosure, cancer or infection is treated by transfer of an immune cell population that elicits an immune response. Provided herein are methods for treating or delaying progression of cancer in an individual comprising administering to the individual an effective amount an antigen-specific cell therapy. The present methods may be applied for the treatment of immune disorders, solid cancers, hematologic cancers, and viral infections.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

Particular embodiments concern methods of treatment of leukemia. Leukemia is a cancer of the blood or bone marrow and is characterized by an abnormal proliferation (production by multiplication) of blood cells, usually white blood cells (leukocytes). It is part of the broad group of diseases called hematological neoplasms. Leukemia is a broad term covering a spectrum of diseases. Leukemia is clinically and pathologically split into its acute and chronic forms.

In certain embodiments of the present disclosure, immune cells are delivered to an individual in need thereof, such as an individual that has cancer or an infection. The cells then enhance the individual's immune system to attack the respective cancer or pathogenic cells. In some cases, the individual is provided with one or more doses of the immune cells. In cases where the individual is provided with two or more doses of the immune cells, the duration between the administrations should be sufficient to allow time for propagation in the individual, and in specific embodiments the duration between doses is 1, 2, 3, 4, 5, 6, 7, or more days.

Certain embodiments of the present disclosure provide methods for treating or preventing an immune-mediated disorder. In one embodiment, the subject has an autoimmune disease. Non-limiting examples of autoimmune diseases include: alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac spate-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, nephrotic syndrome (such as minimal change disease, focal glomerulosclerosis, or mebranous nephropathy), pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon, Reiter's syndrome, Rheumatoid arthritis, sarcoidosis, scleroderma, Sjogren's syndrome, stiff-man syndrome, systemic lupus erythematosus, lupus erythematosus, ulcerative colitis, uveitis, vasculitides (such as polyarteritis nodosa, takayasu arteritis, temporal arteritis/giant cell arteritis, or dermatitis herpetiformis vasculitis), vitiligo, and Wegener's granulomatosis. Thus, some examples of an autoimmune disease that can be treated using the methods disclosed herein include, but are not limited to, multiple sclerosis, rheumatoid arthritis, systemic lupus erythematosis, type I diabetes mellitus, Crohn's disease; ulcerative colitis, myasthenia gravis, glomerulonephritis, ankylosing spondylitis, vasculitis, or psoriasis. The subject can also have an allergic disorder such as Asthma.

In yet another embodiment, the subject is the recipient of a transplanted organ or stem cells and immune cells are used to prevent and/or treat rejection. In particular embodiments, the subject has or is at risk of developing graft versus host disease. GVHD is a possible complication of any transplant that uses or contains stem cells from either a related or an unrelated donor. There are two kinds of GVHD, acute and chronic. Acute GVHD appears within the first three months following transplantation. Signs of acute GVHD include a reddish skin rash on the hands and feet that may spread and become more severe, with peeling or blistering skin. Acute GVHD can also affect the stomach and intestines, in which case cramping, nausea, and diarrhea are present. Yellowing of the skin and eyes (jaundice) indicates that acute GVHD has affected the liver. Chronic GVHD is ranked based on its severity: stage/grade 1 is mild; stage/grade 4 is severe. Chronic GVHD develops three months or later following transplantation. The symptoms of chronic GVHD are similar to those of acute GVHD, but in addition, chronic GVHD may also affect the mucous glands in the eyes, salivary glands in the mouth, and glands that lubricate the stomach lining and intestines. Any of the populations of immune cells disclosed herein can be utilized. Examples of a transplanted organ include a solid organ transplant, such as kidney, liver, skin, pancreas, lung and/or heart, or a cellular transplant such as islets, hepatocytes, myoblasts, bone marrow, or hematopoietic or other stem cells. The transplant can be a composite transplant, such as tissues of the face. Immune cells can be administered prior to transplantation, concurrently with transplantation, or following transplantation. In some embodiments, the immune cells are administered prior to the transplant, such as at least 1 hour, at least 12 hours, at least 1 day, at least 2 days, at least 3 days, at least 4 days, at least 5 days, at least 6 days, at least 1 week, at least 2 weeks, at least 3 weeks, at least 4 weeks, or at least 1 month prior to the transplant. In one specific, non-limiting example, administration of the therapeutically effective amount of immune cells occurs 3-5 days prior to transplantation.

In some embodiments, the subject can be administered nonmyeloablative lymphodepleting chemotherapy prior to the immune cell therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously. Likewise, any suitable dose of cyclophosphamide and fludarabine can be administered. In particular aspects, around 60 mg/kg of cyclophosphamide is administered for two days after which around 25 mg/m² fludarabine is administered for five days.

In certain embodiments, a growth factor that promotes the growth and activation of the immune cells is administered to the subject either concomitantly with the immune cells or subsequently to the immune cells. The immune cell growth factor can be any suitable growth factor that promotes the growth and activation of the immune cells. Examples of suitable immune cell growth factors include interleukin (IL)-2, IL-7, IL-12, IL-15, IL-18, and IL-21, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Therapeutically effective amounts of immune cells can be administered by a number of routes, including parenteral administration, for example, intravenous, intraperitoneal, intramuscular, intrasternal, or intraarticular injection, or infusion.

The therapeutically effective amount of immune cells for use in adoptive cell therapy is that amount that achieves a desired effect in a subject being treated. For instance, this can be the amount of immune cells necessary to inhibit advancement, or to cause regression of an autoimmune or alloimmune disease, or which is capable of relieving symptoms caused by an autoimmune disease, such as pain and inflammation. It can be the amount necessary to relieve symptoms associated with inflammation, such as pain, edema and elevated temperature. It can also be the amount necessary to diminish or prevent rejection of a transplanted organ.

The immune cell population can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective amount of immune cells will be dependent on the subject being treated, the severity and type of the affliction, and the manner of administration. In some embodiments, doses that could be used in the treatment of human subjects range from at least $3.8 \times 10^4$, at least $3.8 \times 10^5$, at least $3.8 \times 10^6$, at least $3.8 \times 10^7$, at least $3.8 \times 10^8$, at least $3.8 \times 10^9$, or at least $3.8 \times 10^{10}$ immune cells/m². In a certain embodiment, the dose used in the treatment of human subjects ranges from about $3.8 \times 10^9$ to about $3.8 \times 10^{10}$ immune cells/m². In additional embodiments, a therapeutically effective amount of immune cells can vary from about $5 \times 10^6$ cells per kg body weight to about $7.5 \times 10^8$ cells per kg body weight, such as about $2 \times 10^7$ cells to about $5 \times 10^8$ cells per kg body weight, or about $5 \times 10^7$ cells to about $2 \times 10^8$ cells per kg body weight. The exact amount of immune cells is readily determined by one of skill in the art based on the age, weight, sex, and physiological condition of the subject. Effective doses can be extrapolated from dose-response curves derived from in vitro or animal model test systems.

The immune cells may be administered in combination with one or more other therapeutic agents for the treatment of the immune-mediated disorder. Combination therapies can include, but are not limited to, one or more antimicrobial agents (for example, antibiotics, anti-viral agents and anti-fungal agents), anti-tumor agents (for example, fluorouracil, methotrexate, paclitaxel, fludarabine, etoposide, doxorubicin, or vincristine), immune-depleting agents (for example, fludarabine, etoposide, doxorubicin, or vincristine), immunosuppressive agents (for example, azathioprine, or glucocorticoids, such as dexamethasone or prednisone), anti-inflammatory agents (for example, glucocorticoids such as hydrocortisone, dexamethasone or prednisone, or non-steroidal anti-inflammatory agents such as acetylsalicylic acid, ibuprofen or naproxen sodium), cytokines (for example, interleukin-10 or transforming growth factor-beta), hormones (for example, estrogen), or a vaccine. In addition, immunosuppressive or tolerogenic agents including but not limited to calcineurin inhibitors (e.g., cyclosporin and tacrolimus); mTOR inhibitors (e.g., Rapamycin); mycophenolate mofetil, antibodies (e.g., recognizing CD3, CD4, CD40, CD154, CD45, IVIG, or B cells); chemotherapeutic agents (e.g., Methotrexate, Treosulfan, Busulfan); irradiation; or chemokines, interleukins or their inhibitors (e.g., BAFF, IL-2, anti-IL-2R, IL-4, JAK kinase inhibitors) can be administered. Such additional pharmaceutical agents can be administered before, during, or after administration of the immune cells, depending on the desired effect. This administration of the cells and the agent can be by the same route or by different routes, and either at the same site or at a different site.

A. Pharmaceutical Compositions

Also provided herein are pharmaceutical compositions and formulations comprising immune cells (e.g., T cells, B cells, or NK cells) and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences $22^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn— protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

B. Combination Therapies

In certain embodiments, the compositions and methods of the present embodiments involve an immune cell population in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

An immune cell therapy may be administered before, during, after, or in various combinations relative to an additional cancer therapy, such as immune checkpoint therapy. The administrations may be in intervals ranging from concurrently to minutes to days to weeks. In embodiments where the immune cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below an immune cell therapy is "A" and an anti-cancer therapy is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegal1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation, and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates (ADCs) comprise monoclonal antibodies (MAbs) that are covalently linked to cell-killing drugs and may be used in combination therapies. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. Exemplary ADC drugs include ADCETRIS® (brentuximab vedotin) and KADCYLA® (trastuzumab emtansine or T-DM1).

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include immune adjuvants, e.g., *Mycobacterium bovis, Plasmodium falciparum,* dinitrochlorobenzene, and aromatic compounds); cytokine therapy, e.g., interferons α, β, and γ, IL-1, GM-CSF, and TNF; gene therapy, e.g., TNF, IL-1, IL-2, and p53; and monoclonal antibodies, e.g., anti-CD20, anti-ganglioside GM2, and anti-p185. It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lympho-cyte-associated protein 4 (CTLA-4, also known as CD152), indoleamine 2,3-dioxygenase (IDO), killer-cell immuno-globulin (KIR), lymphocyte activation gene-3 (LAG3), pro-grammed death 1 (PD-1), T-cell immunoglobulin domain and mucin domain 3 (TIM-3) and V-domain Ig suppressor of T cell activation (VISTA). In particular, the immune check-point inhibitors target the PD-1 axis and/or CTLA-4.

The immune checkpoint inhibitors may be drugs such as small molecules, recombinant forms of ligand or receptors, or, in particular, are antibodies, such as human antibodies. Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodi-ment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen bind-ing fragment thereof, an immunoadhesin, a fusion protein, or oligopeptide.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodi-ments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody that may be used. Pembrolizumab, also known as MK-3475, Merck 3475, lambrolizumab, KEYTRUDA®, and SCH-900475, is an exemplary anti-PD-1 antibody. CT-011, also known as hBAT or hBAT-1, is also an anti-PD-1 antibody. AMP-224, also known as B7-DCIg, is a PDL2-Fc fusion soluble receptor.

Another immune checkpoint that can be targeted in the methods provided herein is the cytotoxic T-lymphocyte-associated protein 4 (CTLA-4), also known as CD152. The complete cDNA sequence of human CTLA-4 has the Gen-bank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respec-tively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a human-ized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. An exemplary anti-CTLA-4 antibody is ipili-mumab (also known as 10D1, MDX-010, MDX-101, and Yervoy®) or antigen binding fragments and variants thereof. In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-men-tioned antibodies (e.g., at least about 90%, 95%, or 99% variable region identity with ipilimumab).

4. Surgery

Approximately 60% of persons with cancer will undergo surgery of some type, which includes preventative, diagnos-tic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radio-therapy, hormonal therapy, gene therapy, immunotherapy, and/or alternative therapies. Tumor resection refers to physi-cal removal of at least part of a tumor. In addition to tumor resection, treatment by surgery includes laser surgery, cryo-surgery, electrosurgery, and microscopically-controlled sur-gery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodi-ments to improve the therapeutic efficacy of treatment. These additional agents include agents that affect the upregulation of cell surface receptors and GAP junctions, cytostatic and differentiation agents, inhibitors of cell adhe-sion, agents that increase the sensitivity of the hyperprolif-erative cells to apoptotic inducers, or other biological agents. Increases in intercellular signaling by elevating the number of GAP junctions would increase the anti-hyperproliferative effects on the neighboring hyperproliferative cell popula-tion. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

VII. Articles of Manufacture or Kits

An article of manufacture or a kit is provided comprising immune cells is also provided herein. The article of manufacture or kit can further comprise a package insert comprising instructions for using the immune cells to treat or delay progression of cancer in an individual or to enhance immune function of an individual having cancer. Any of the antigen-specific immune cells described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Multiplex Gene Editing

To test the efficacy of simultaneously disrupting the expression of multiple genes in immune cells, such as T cell and NK cells, several studies were performed to test the disruption of different combinations of genes using CRISPR. In a first study, CRISPR/Cas9 was used to disrupt expression of NKG2A, CD47, TGFBR2, and CISH in NK cells. In this set of genes, NKG2A and CD47 were knocked out in the first round of electroporation and in the second round of electroporation CISH and TGFBR2 were targeted. Knockout efficiency was successfully validated using PCR and flow-cytometry for both rounds of electroporation (FIG. 1).

Figure 2:
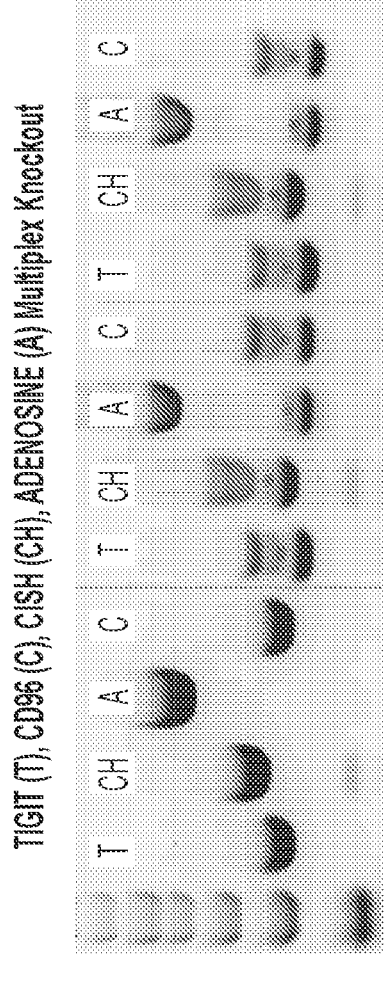
FIG. 2: Validation of multiplex gene editing in NK cells using another set of genes (TIGIT (T), CD96 (C), CISH (CH), Adenosine (A)). In this set of genes, TIGIT and CD96 were knocked out in the first round of electroporation and in the second round of electroporation CISH and Adenosine were targeted. Knockout efficiency was successfully validated using PCR and flow-cytometry for both rounds of electroporation. The red (peaks on the right) and blue (peaks on the left) histograms in the flow panels represent expression of the protein before and after CRISPR KO, respectively.
Figure 2:
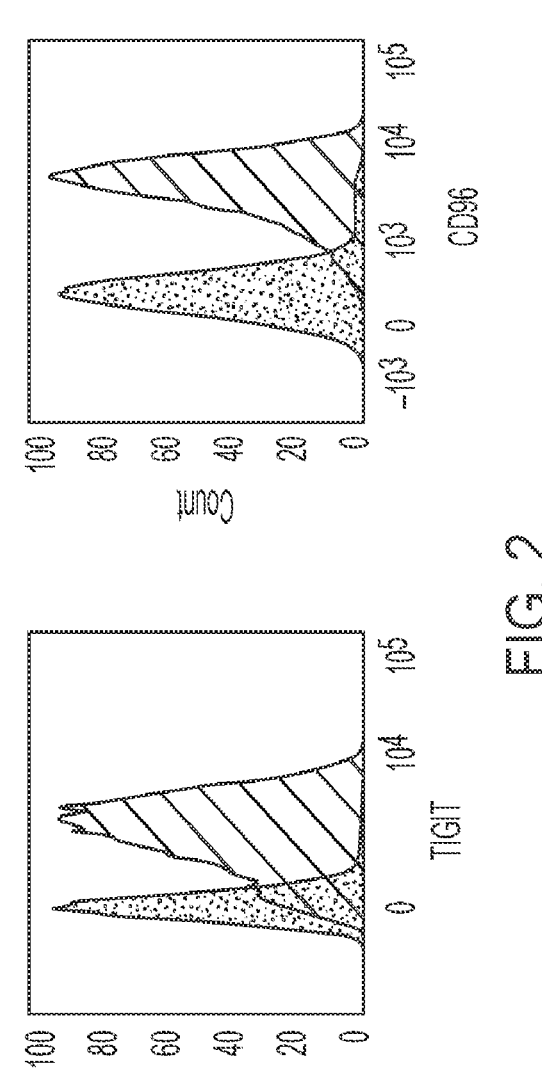
Figure 2:
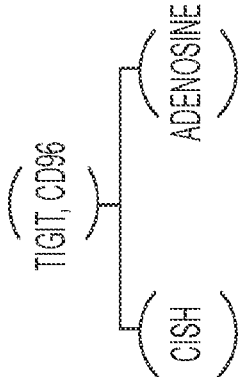
Figure 3:
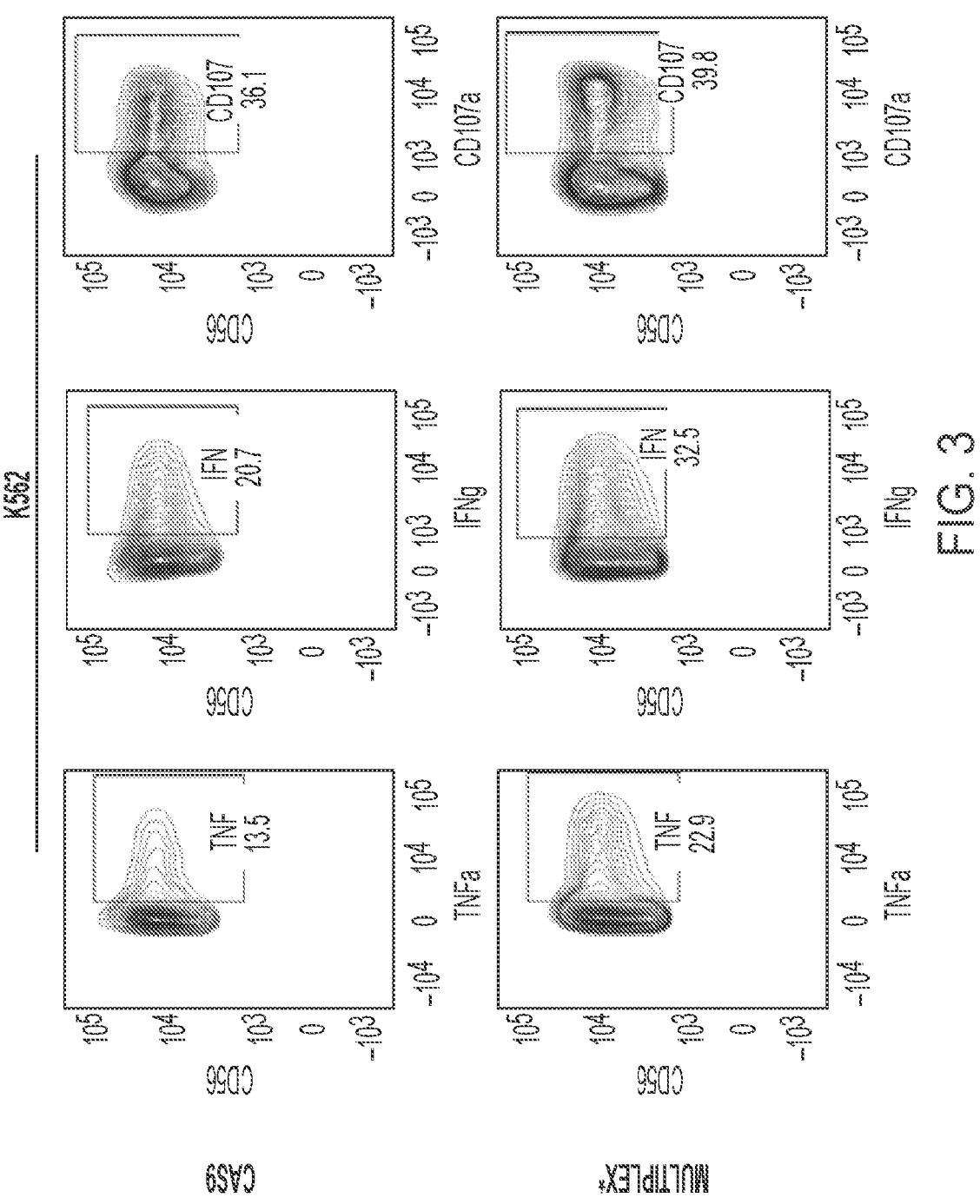
FIG. 3: Disruption of multiple genes (NKG2A, CD47, TGFBR2 and CISH) in NK cells leads to enhanced functionality against target tumor cells. There was enhanced IFN-γ, TNFα and CD107 secretion following stimulation with target cell lines. Flow cytometric analysis of IFN-γ, TNFα and CD107 production was performed with varying NK cells (Edited vs Cas9 alone) co-stimulated with target cell lines for 5 hr in the presence of Brefeldin A.
Figure 3:
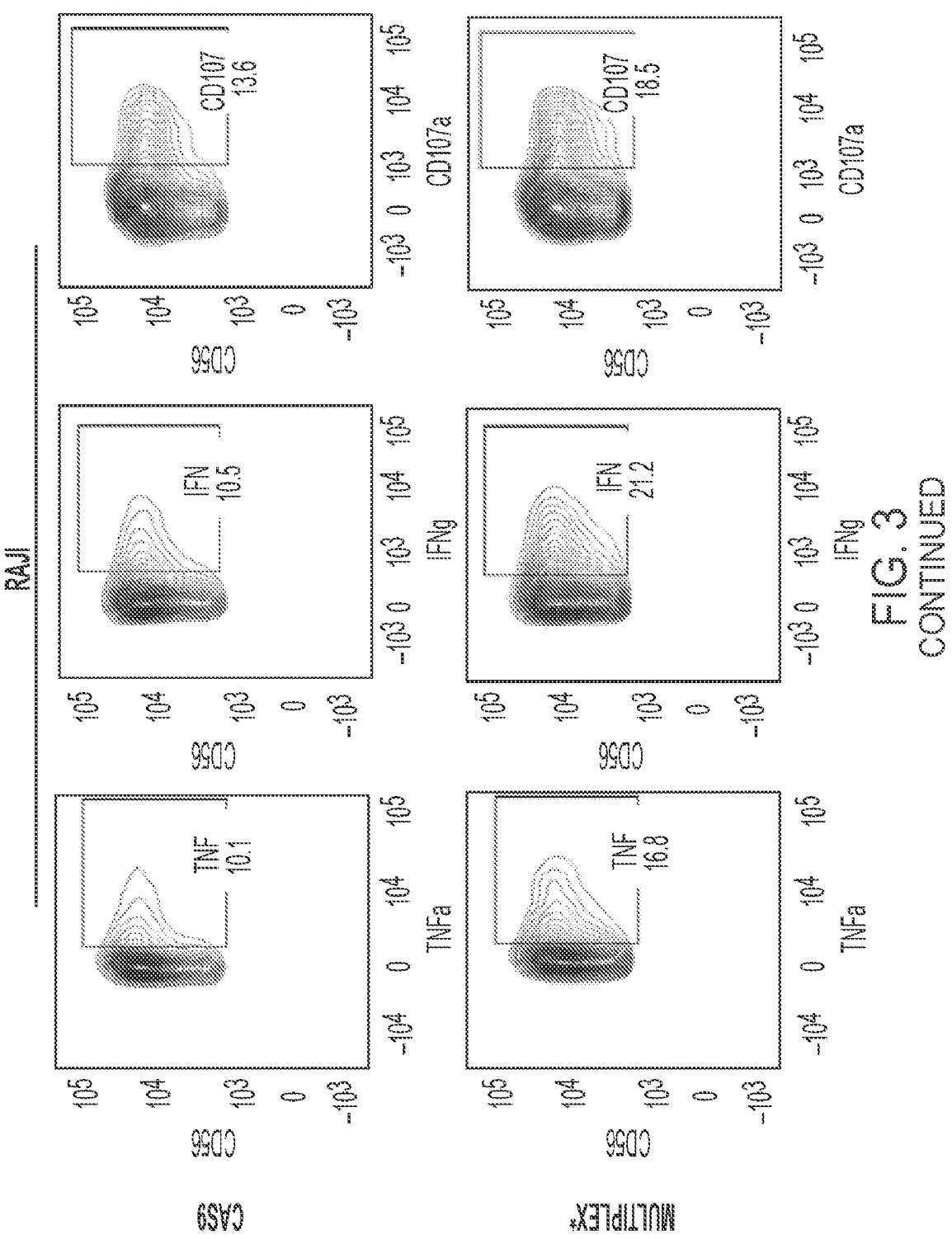

The method of disrupting multiple genes was validated in additional sets of genes including TIGIT, CD96, CISH, Adenosine (FIG. 2) and NKG2A, CD47, TGFBR2 and CISH (FIG. 3). It was found that the disruption of the multiple genes results in enhanced functionality against target tumor cells. Flow cytometric analysis of IFN-γ, TNFα and CD107 production was performed with varying NK cells (Edited vs Cas9 alone) co-stimulated with target cell lines for 5 hr in the presence of Brefeldin A. There was enhanced IFN-γ, TNFα and CD107 secretion following stimulation with target cell lines (FIG. 3)

Figure 4B:
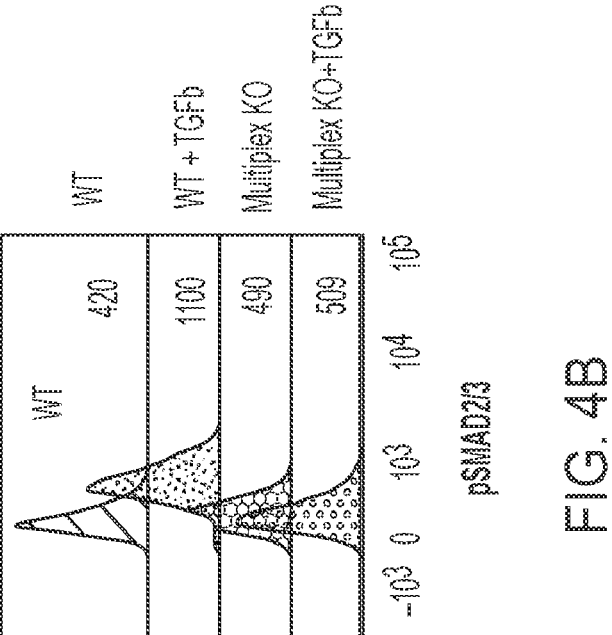
FIGS. 4A-4B: Disruption of multiple genes (NKG2A, CD47, TGFBR2 and CISH) in NK cells leads to enhanced antitumor cytotoxicity.
Figure 4A:
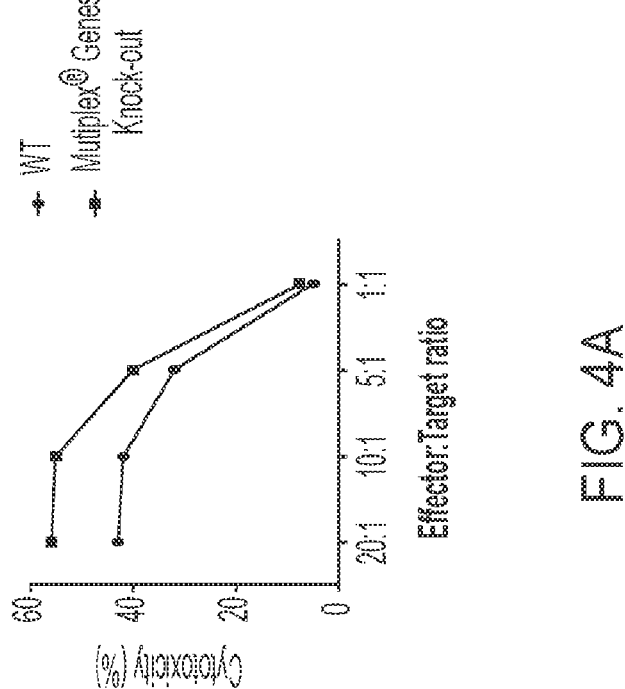
Figure 5:
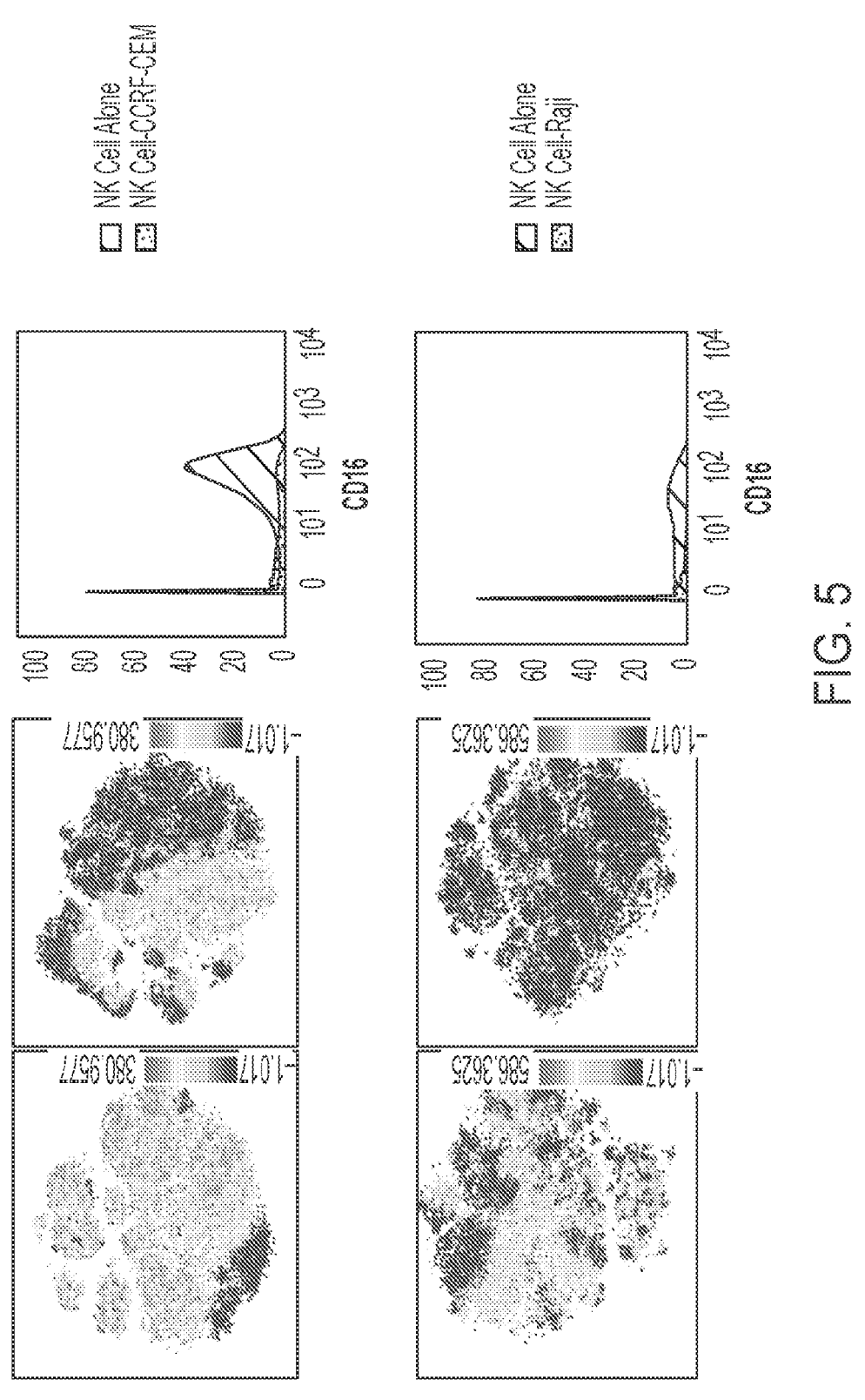
FIG. 5: NK cells lose CD16 and CD62L expression upon cytokine stimulation or target recognition as depicted by CyTOF analysis.
Figure 6:
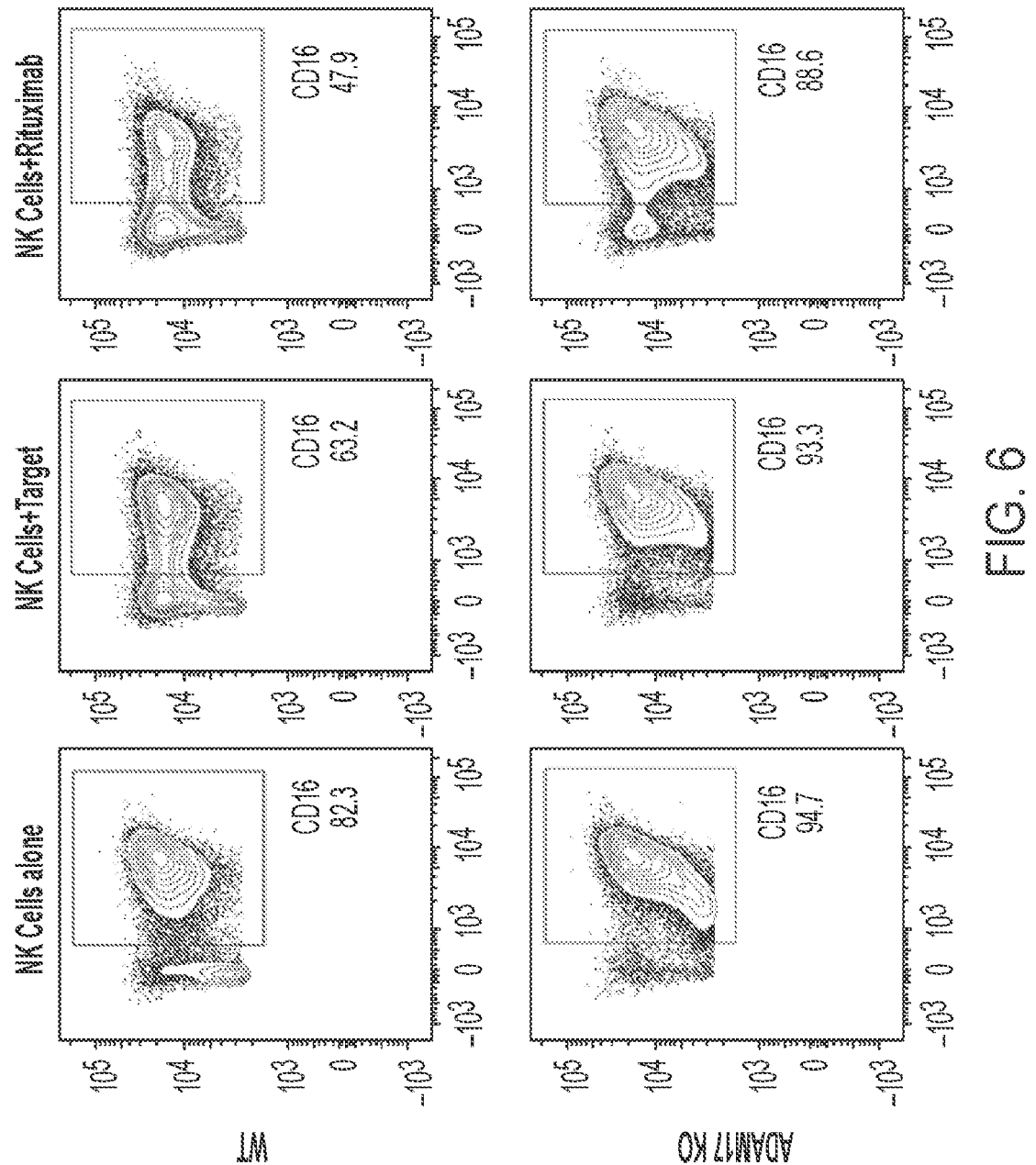
FIG. 6: Knockout of ADAM17 in NK cells prevent shedding of CD16 and CD62L.
Figure 6:
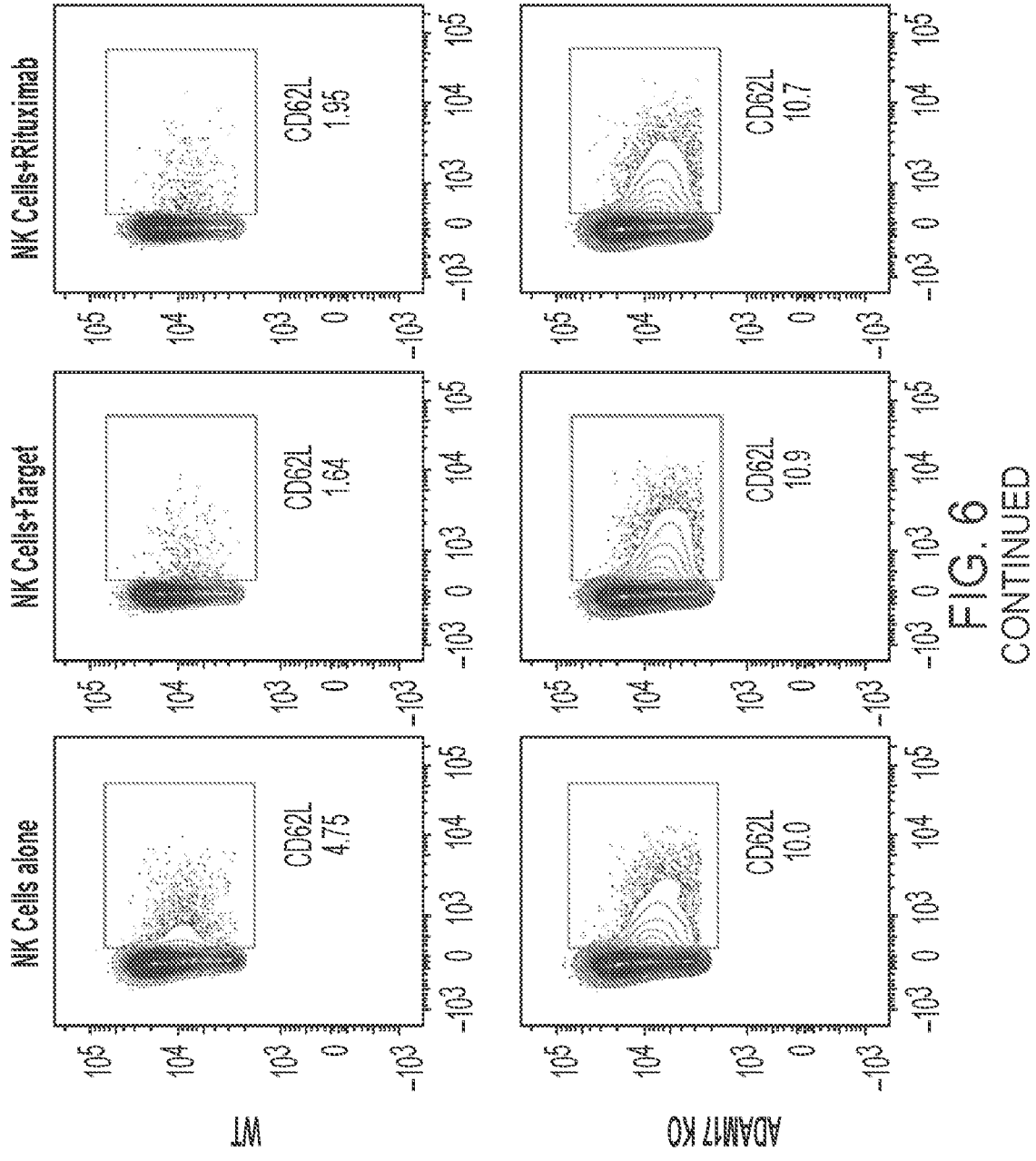
Figure 7:
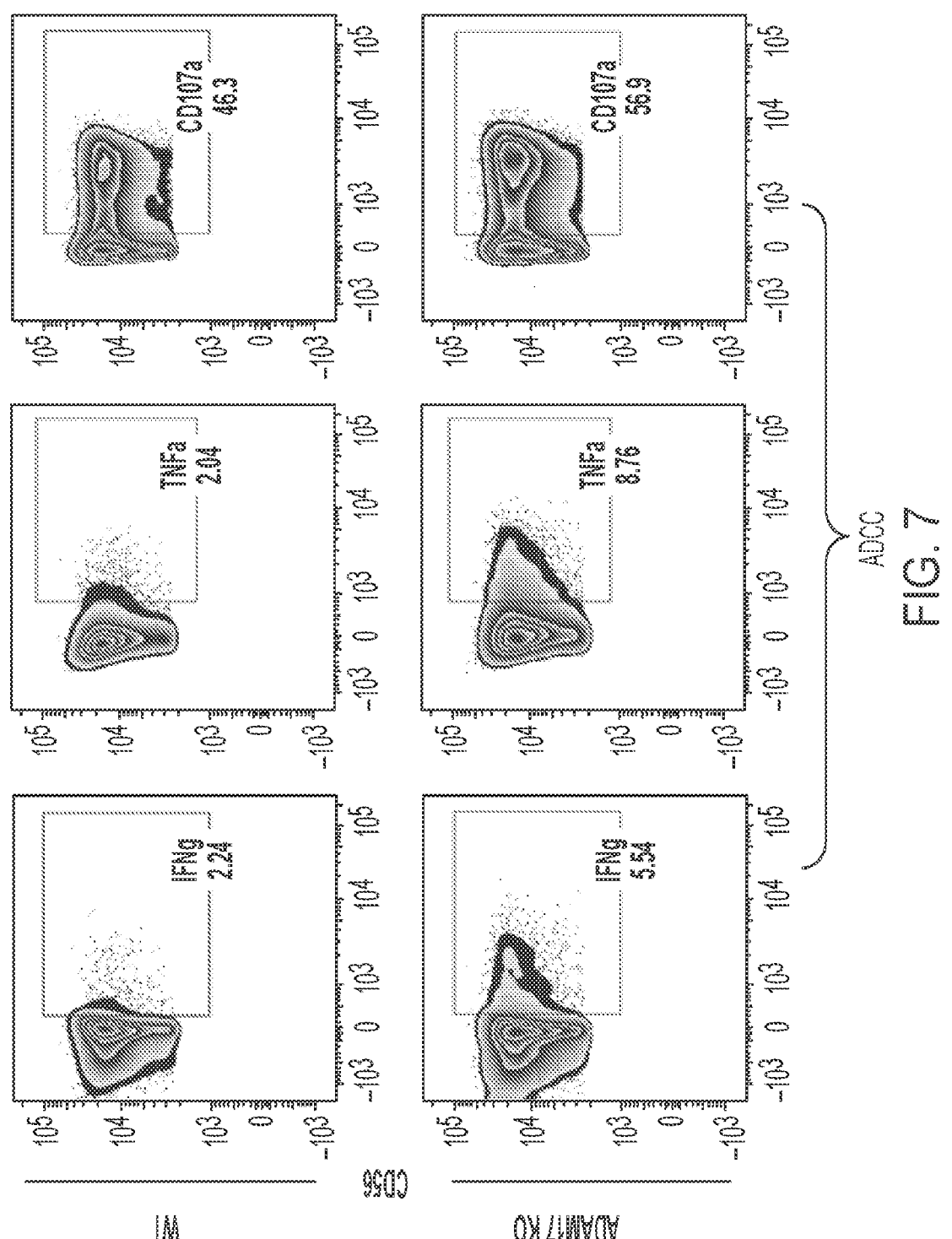
FIG. 7: Knockout ADAM17 in NK cells improves ADCC and cytotoxicity against K562 targets.
Figure 7:
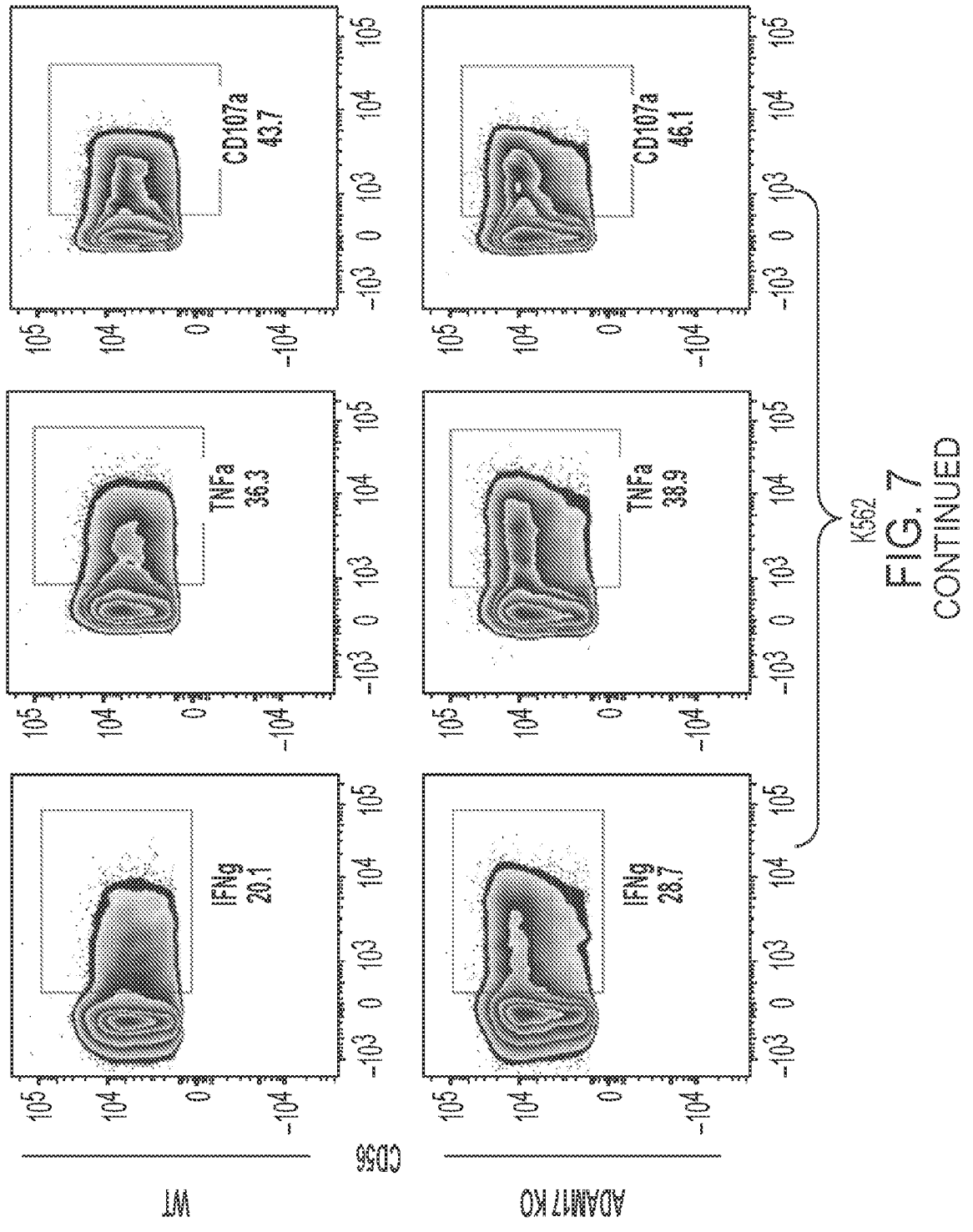
Figure 8:
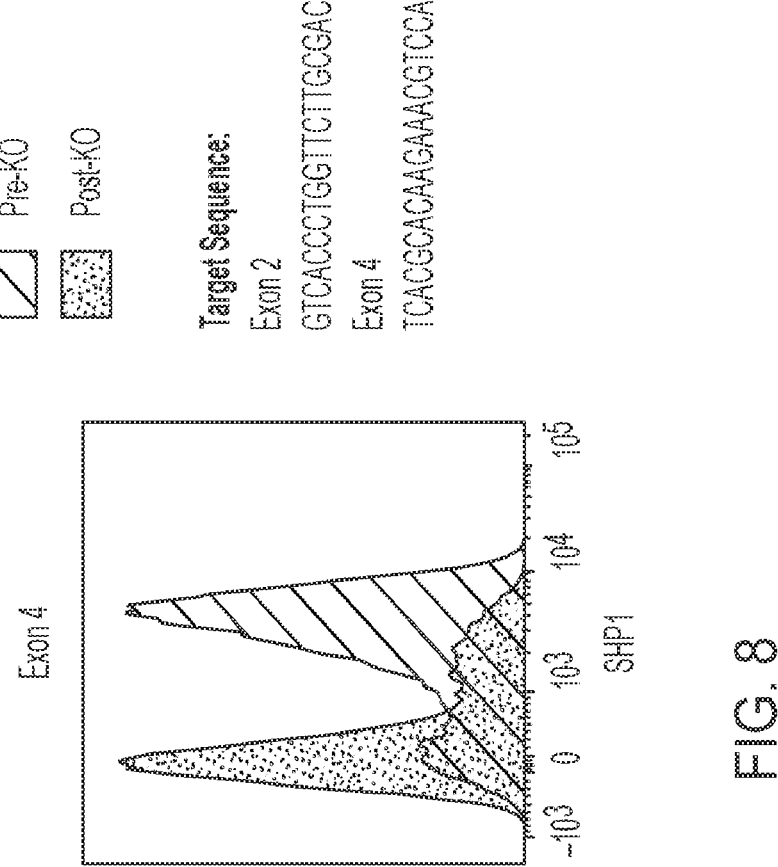
FIG. 8: FACS-based screening of SHP1 knockout efficiency in NK cells at 72 h.
Figure 8:
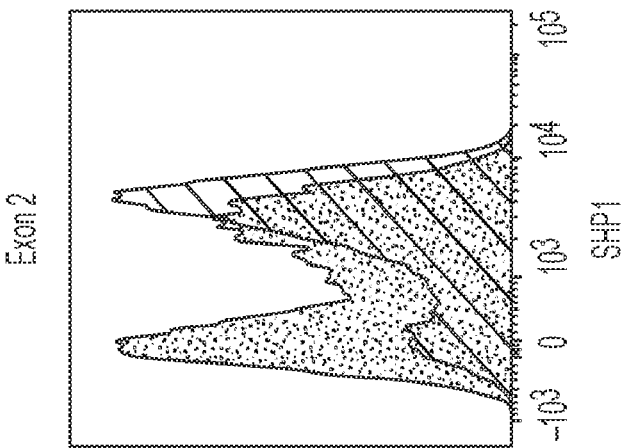

This enhanced functionality was confirmed by disruption of NKG2A, CD47, TGFBR2 and CISH in NK cells which showed enhanced antitumor cytotoxicity. (FIG. 4A) as measured by $^{51}$Cr-release assay, against K562 cells. In addition, following 30 minutes of recombinant TGF-B treatment (50 ng/ml) pSMAD activity was measured by flow cytometry (FIG. 4B). It was also observed that NK cells lose CD16 and CD62L expression upon cytokine stimulation or target recognition (FIG. 5) and knockout of ADAM17 in NK cells prevent shedding of CD16 and CD62L (FIG. 6) and improves ADCC and cytotoxicity against K562 targets (FIG. 7).

Figure 9:
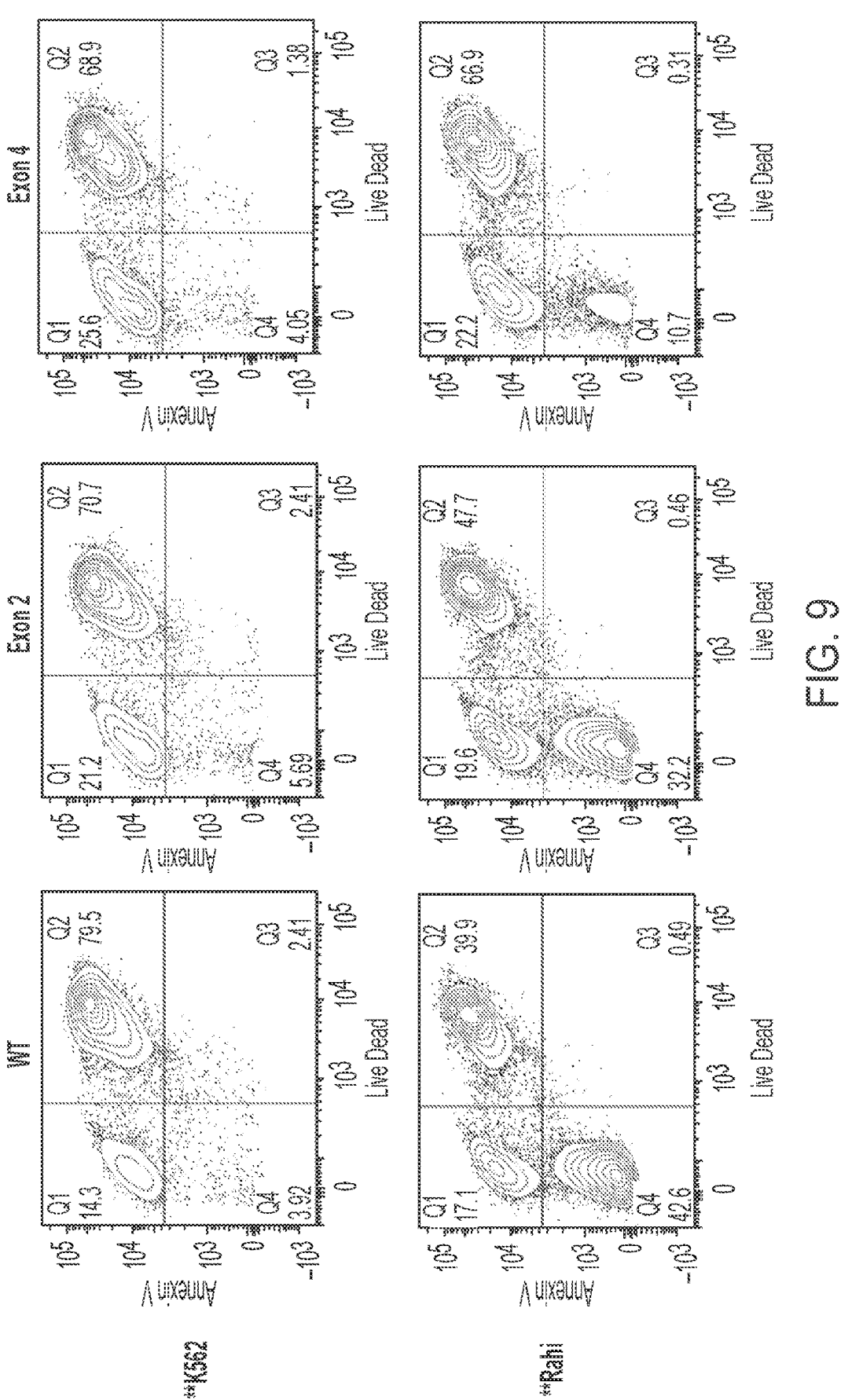
FIG. 9: Disruption of SHP1 in NK cells leads to enhanced antitumor efficacy. NK cells were co-cultured with K562 or Raji cells at a 1:1 ratio for 4 hours. After the incubation, the cells were stained with annexin V and live and dead cells were analyzed. The K562 cells are sensitive to NK cell killing and the Raji cells are resistant to NK cell killing.
Figure 10A:
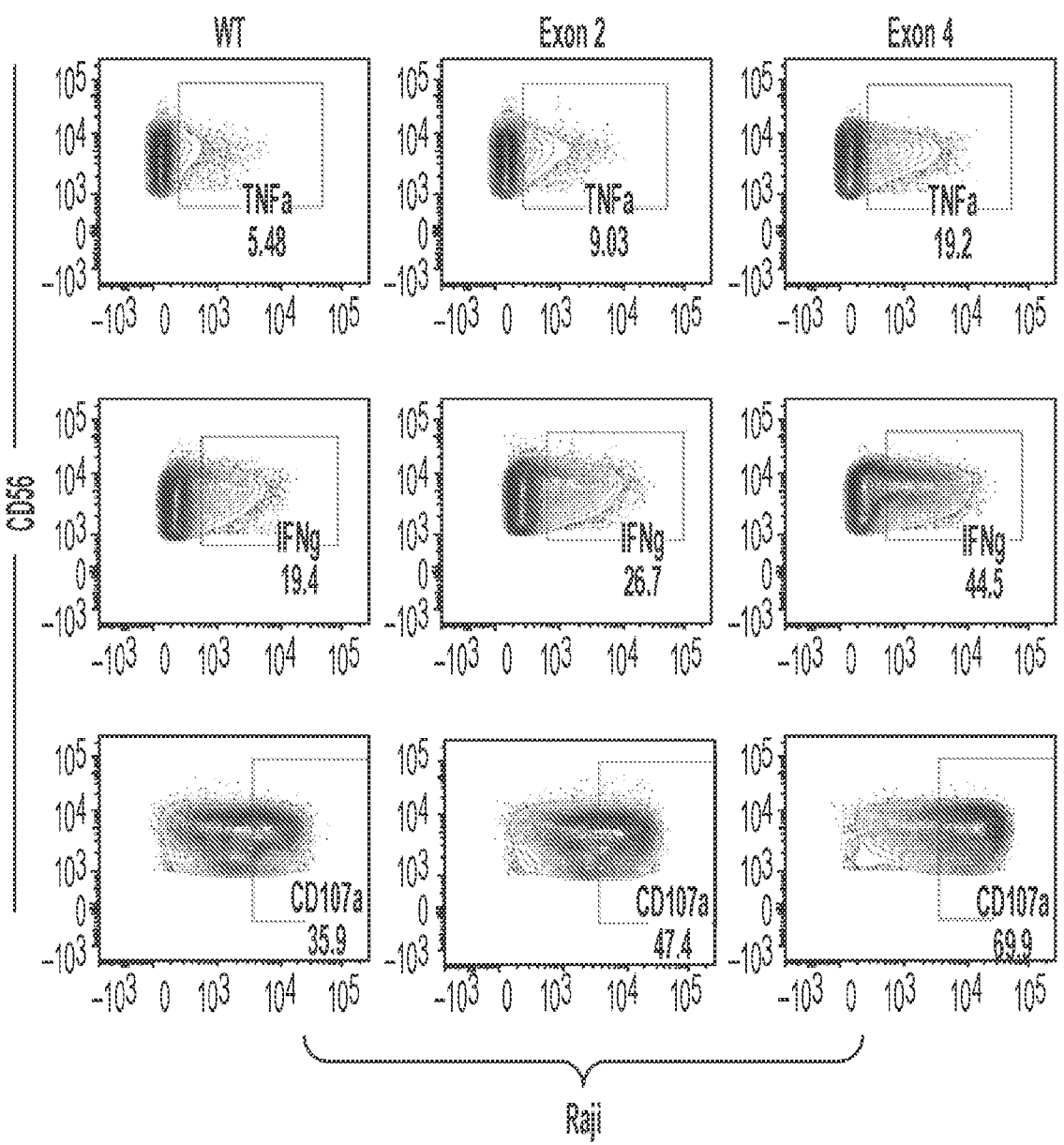
FIGS. 10A-10B: Disruption of SHP1 in NK cells leads to enhanced antitumor efficacy (FIG. 10A). NK cells were co-cultured with K562 or Raji cells at a 2:1 ratio for 5 hours (FIG. 10B). Percent of lysis at various effector:target ratios, percentage of IFNγ, TNFα, and CD107a, and percentage of live or dead cells are shown.
Figure 10A:
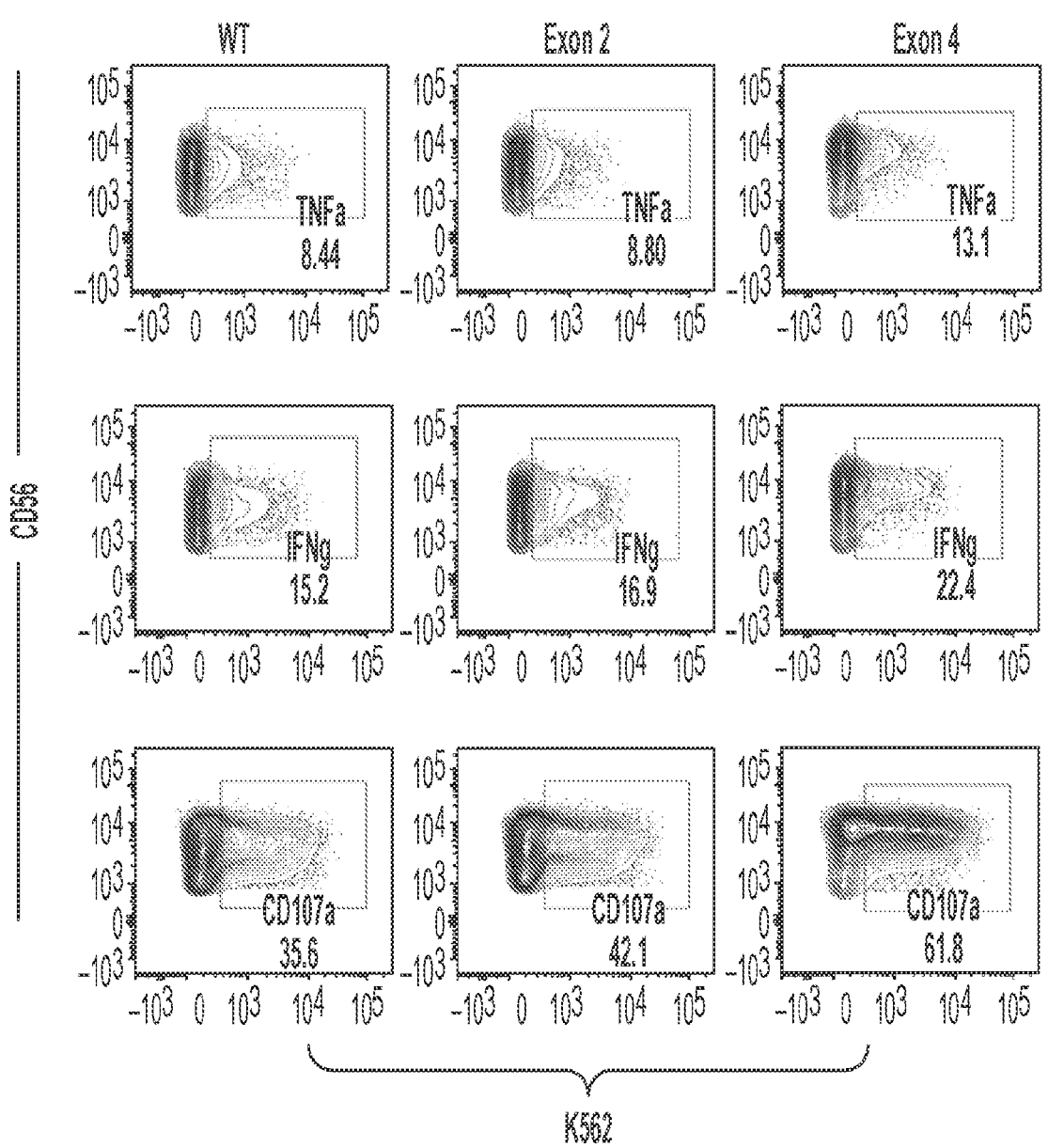
Figure 10B:
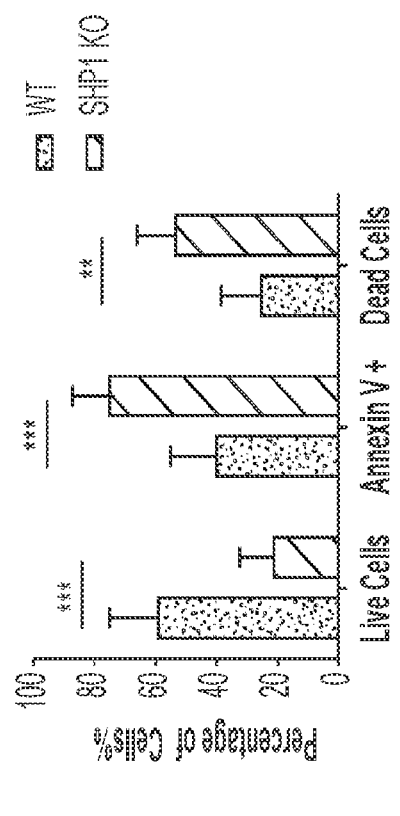
Figure 10B:
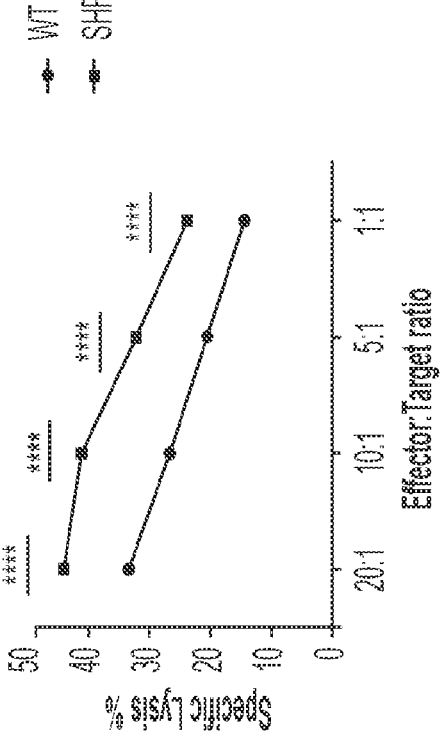
Figure 10B:
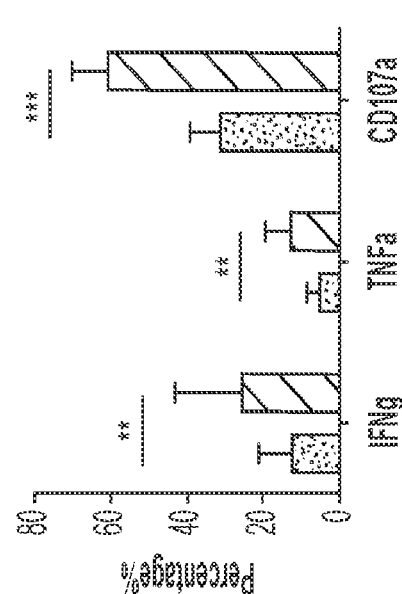
Figure 11:
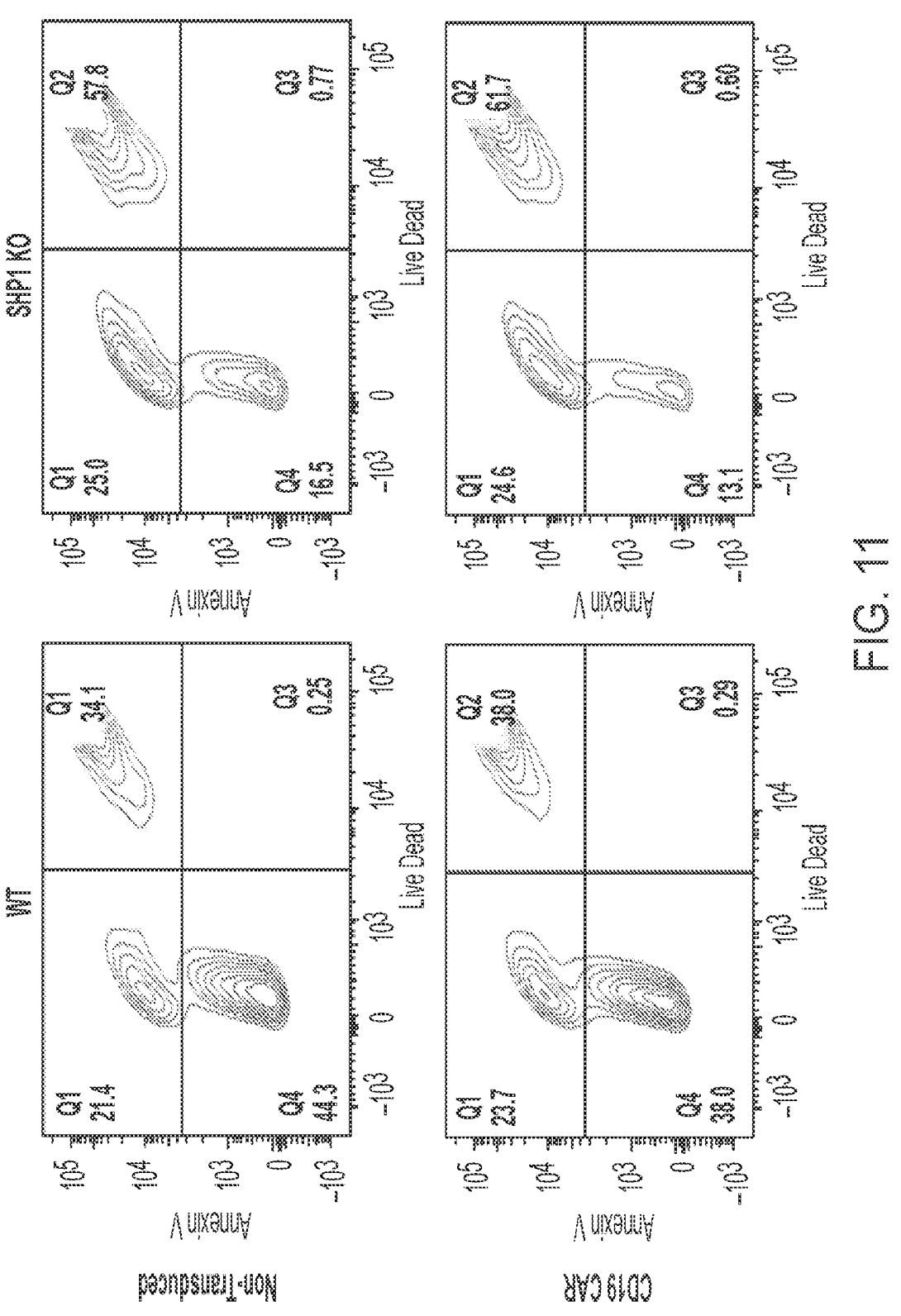
FIG. 11: Disruption of SHP1 in NK-CAR cells leads to enhanced antitumor efficacy as assessed by apoptosis assay.
Figure 12A:
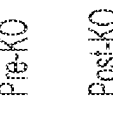
FIGS. 12A-12C.
Figure 12A:
Figure 12A:
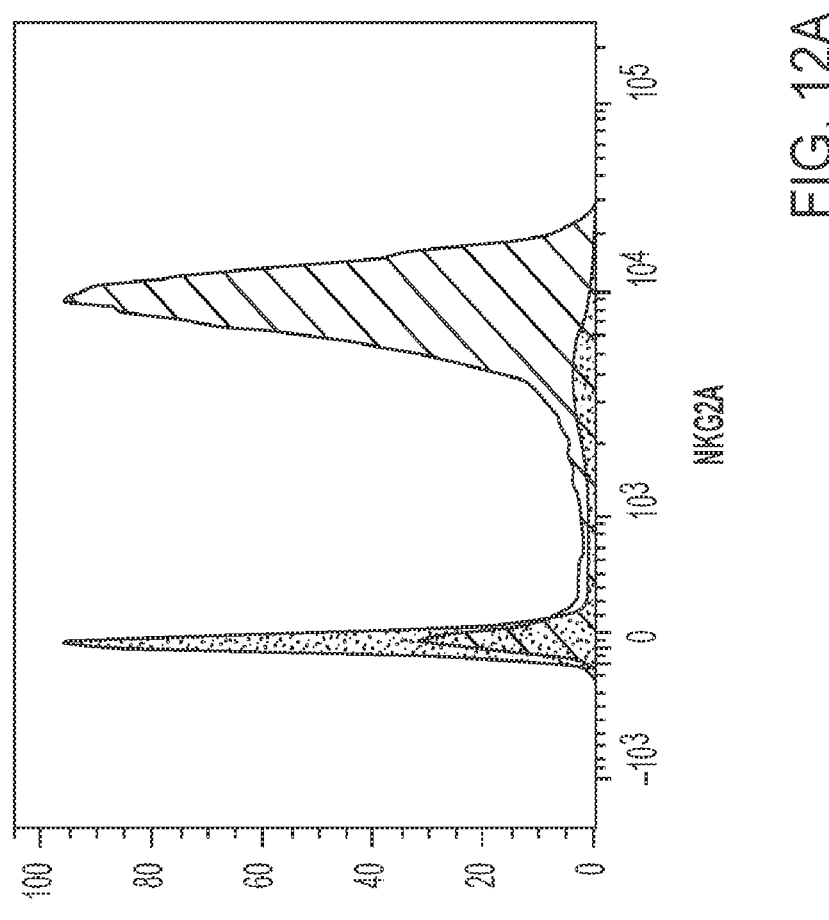
Figure 12B:
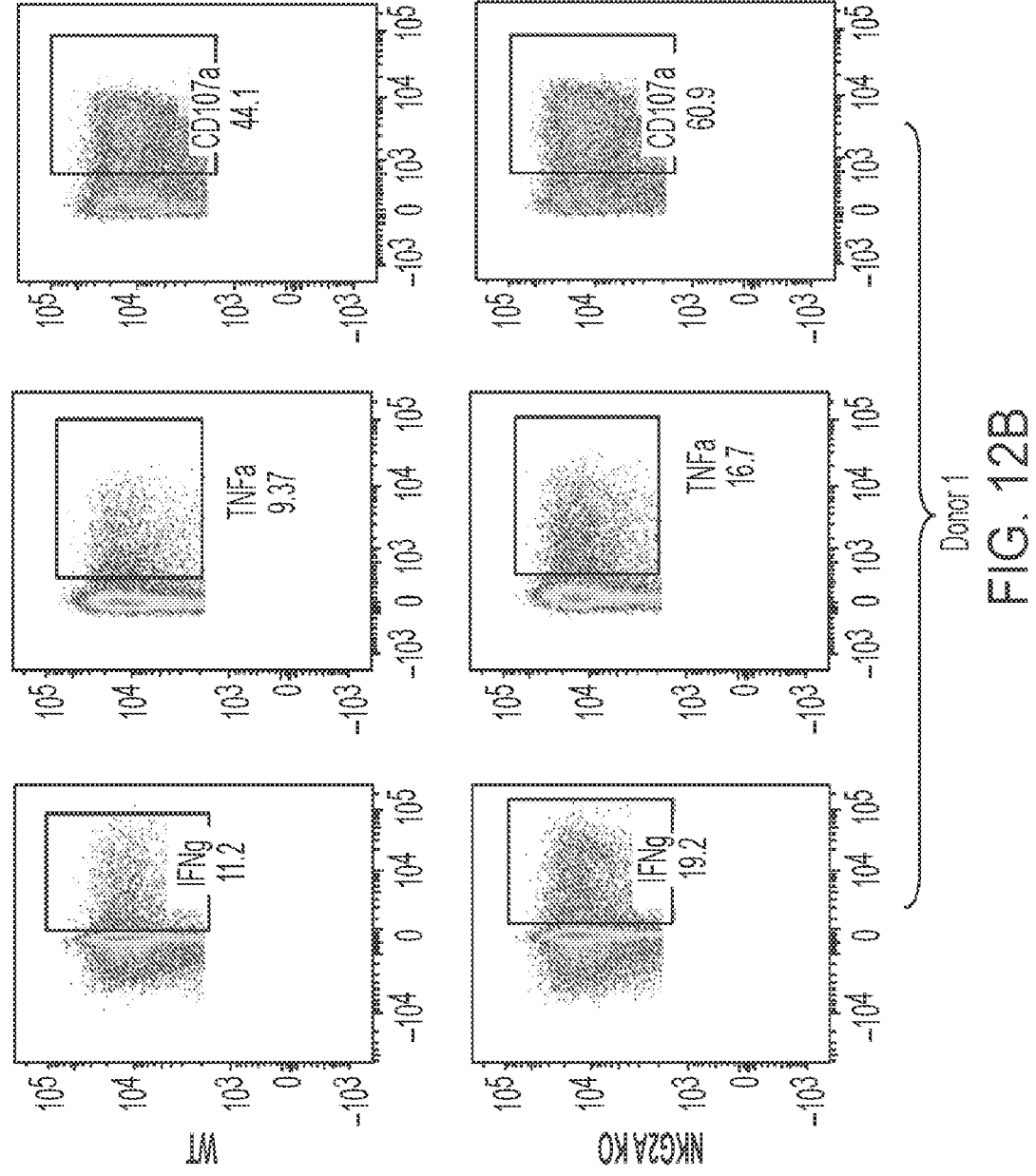
Figure 12B:
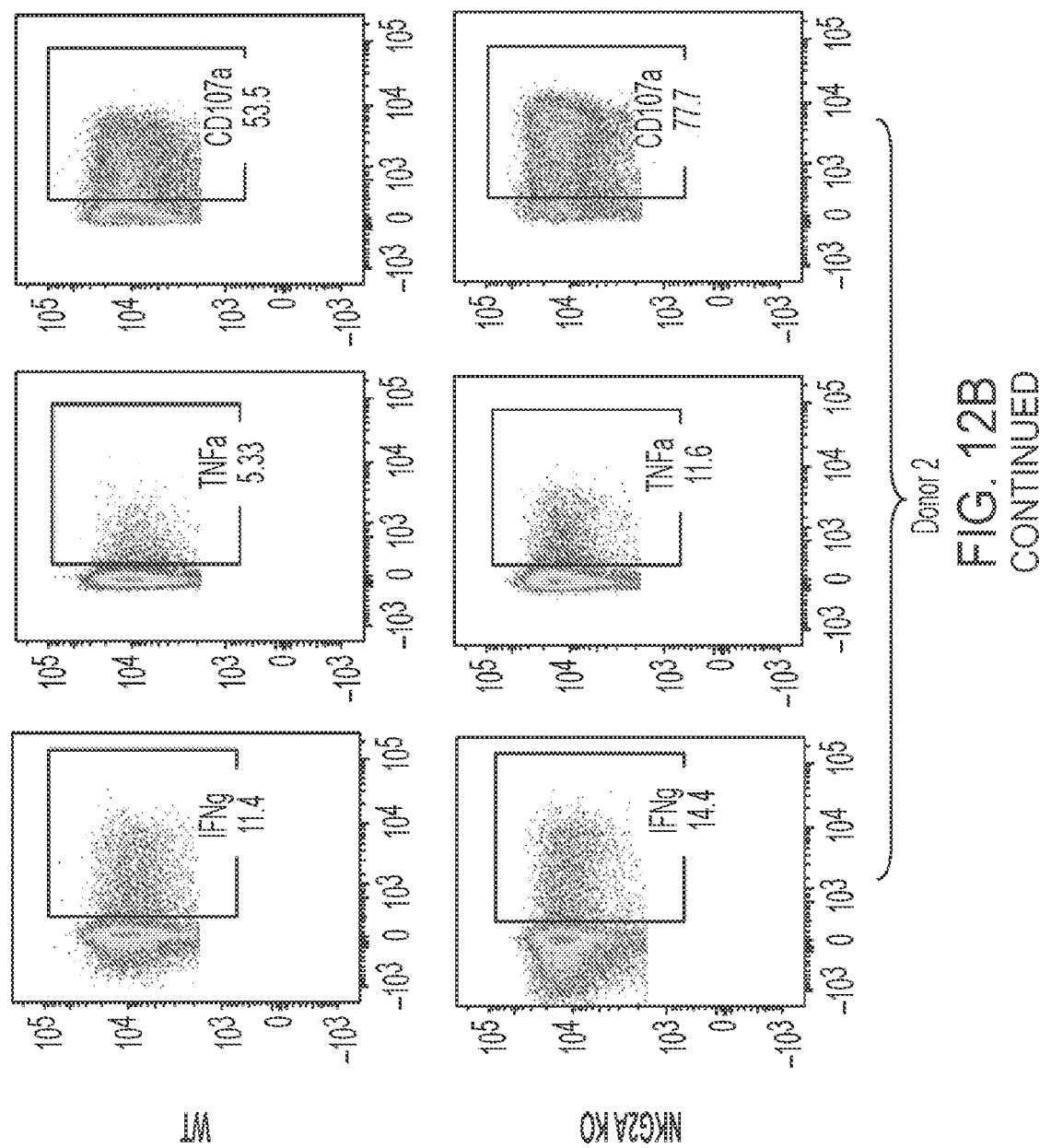
Figure 12C:
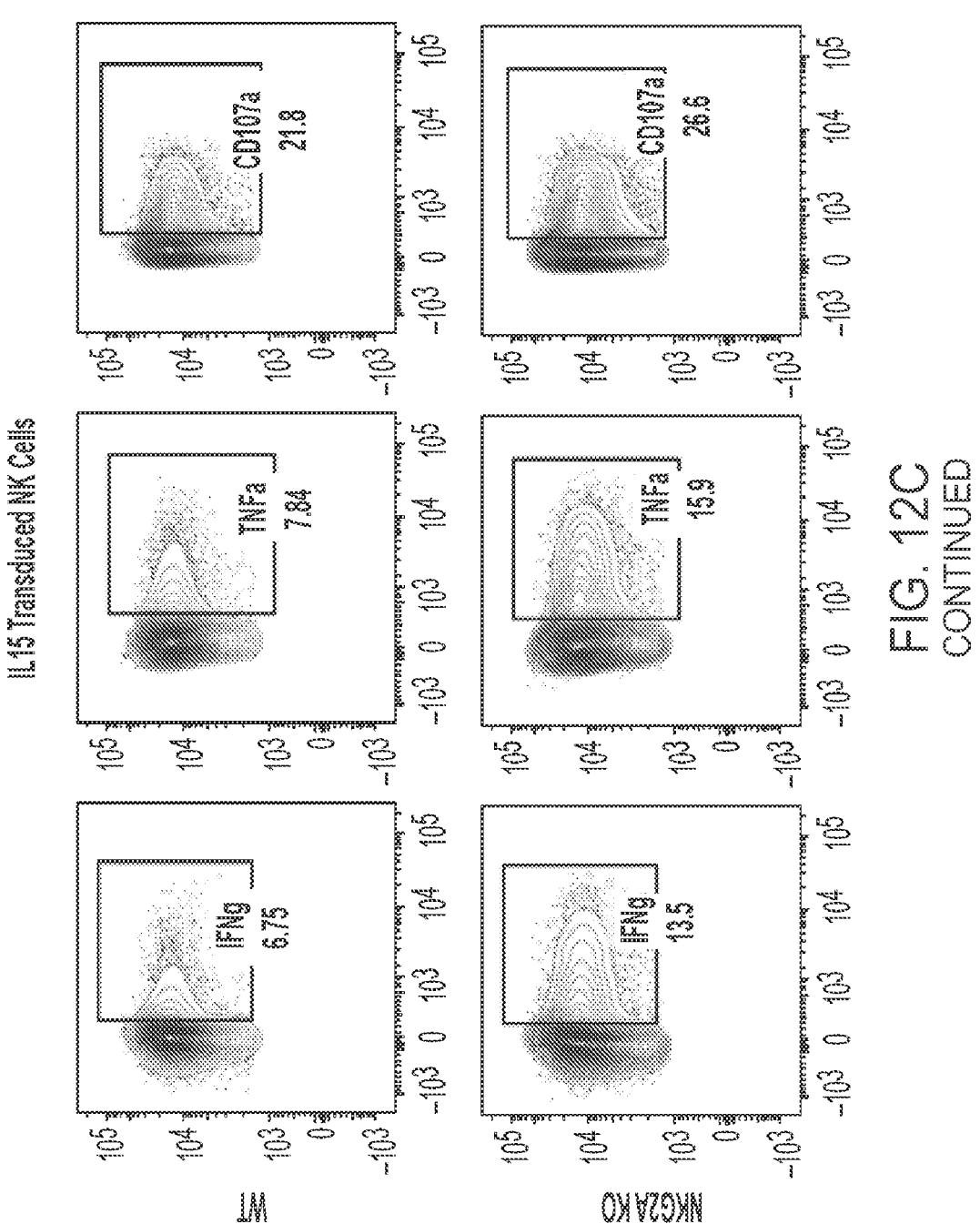
Figure 12C:
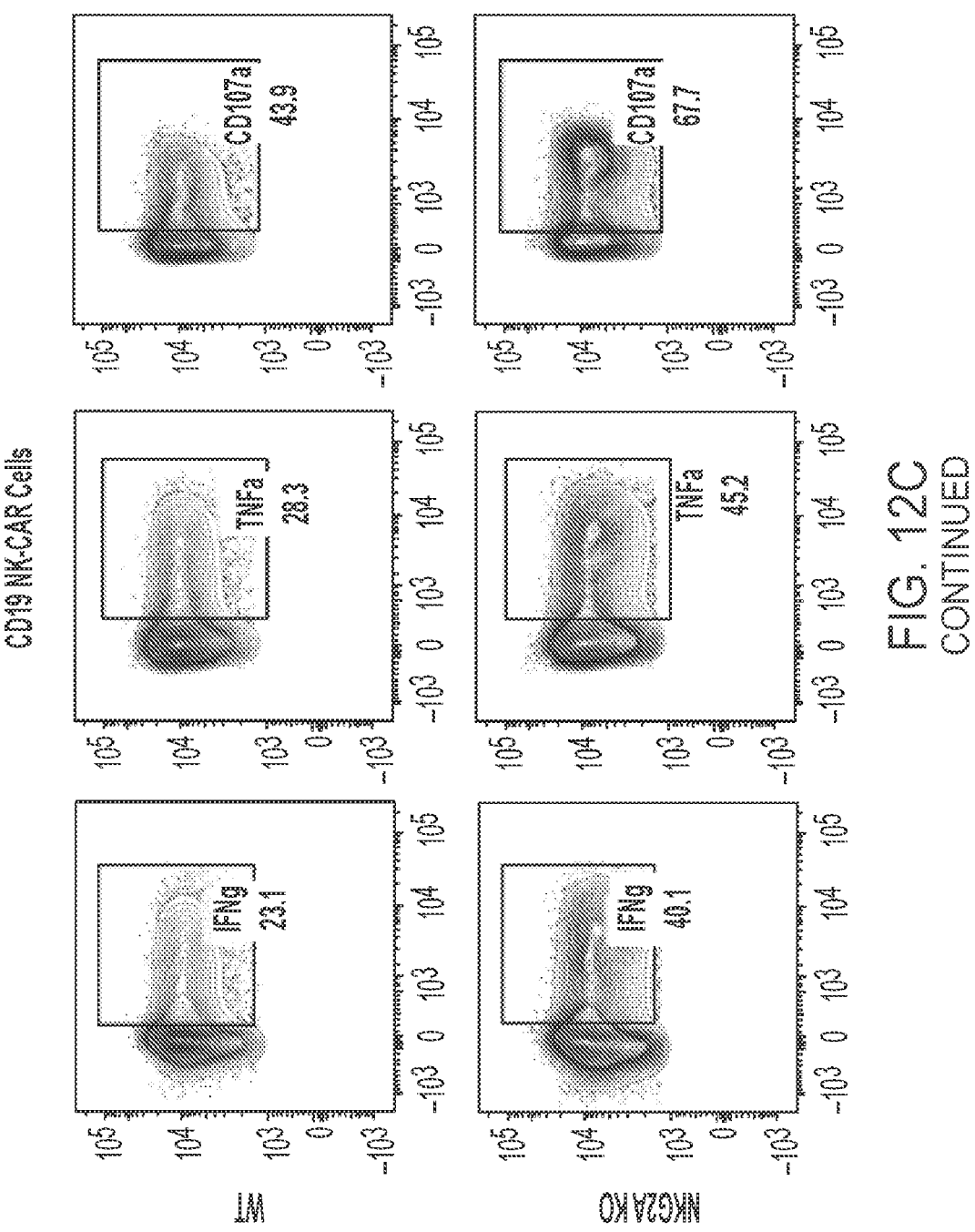
Figure 12C:
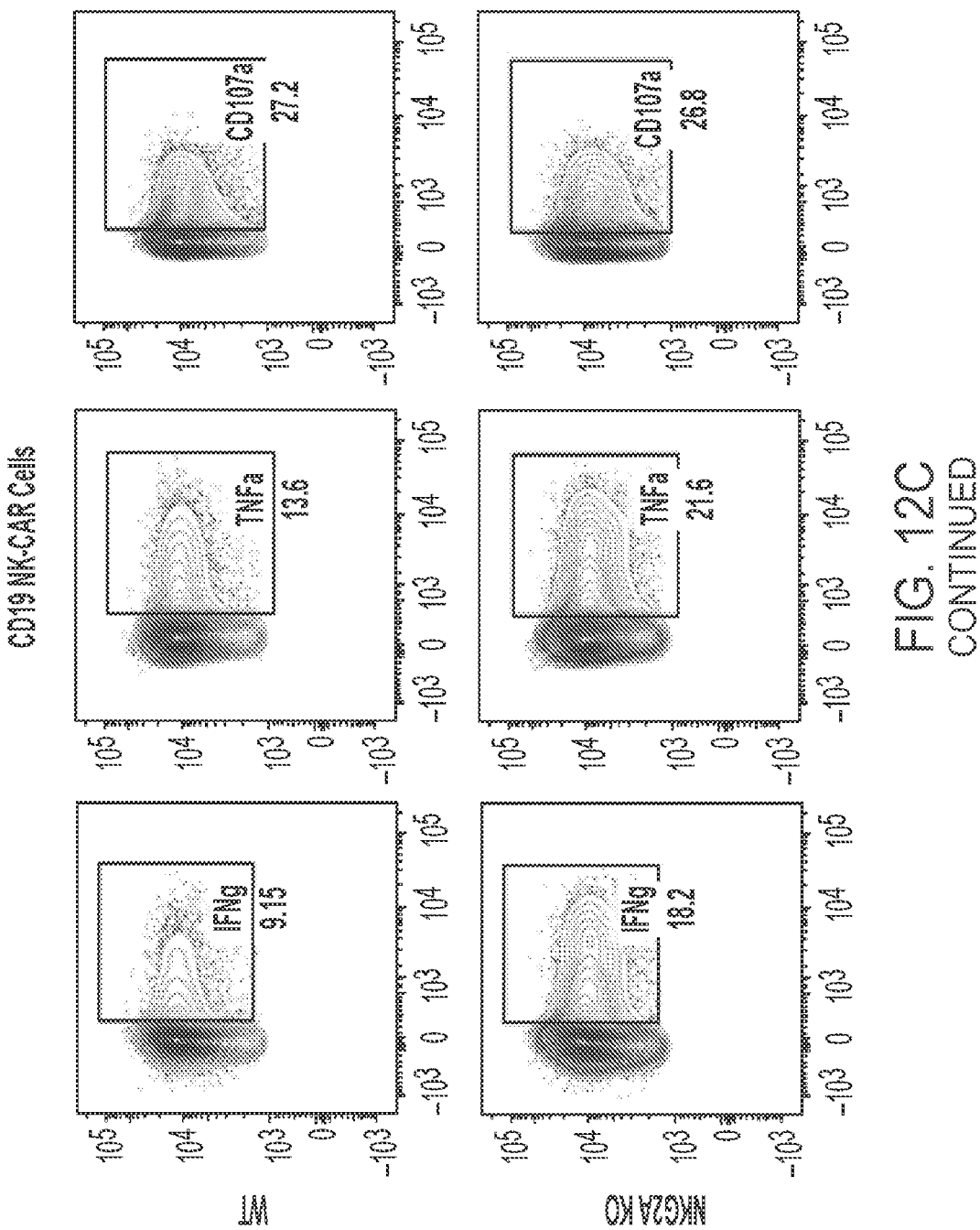
Figure 12C:
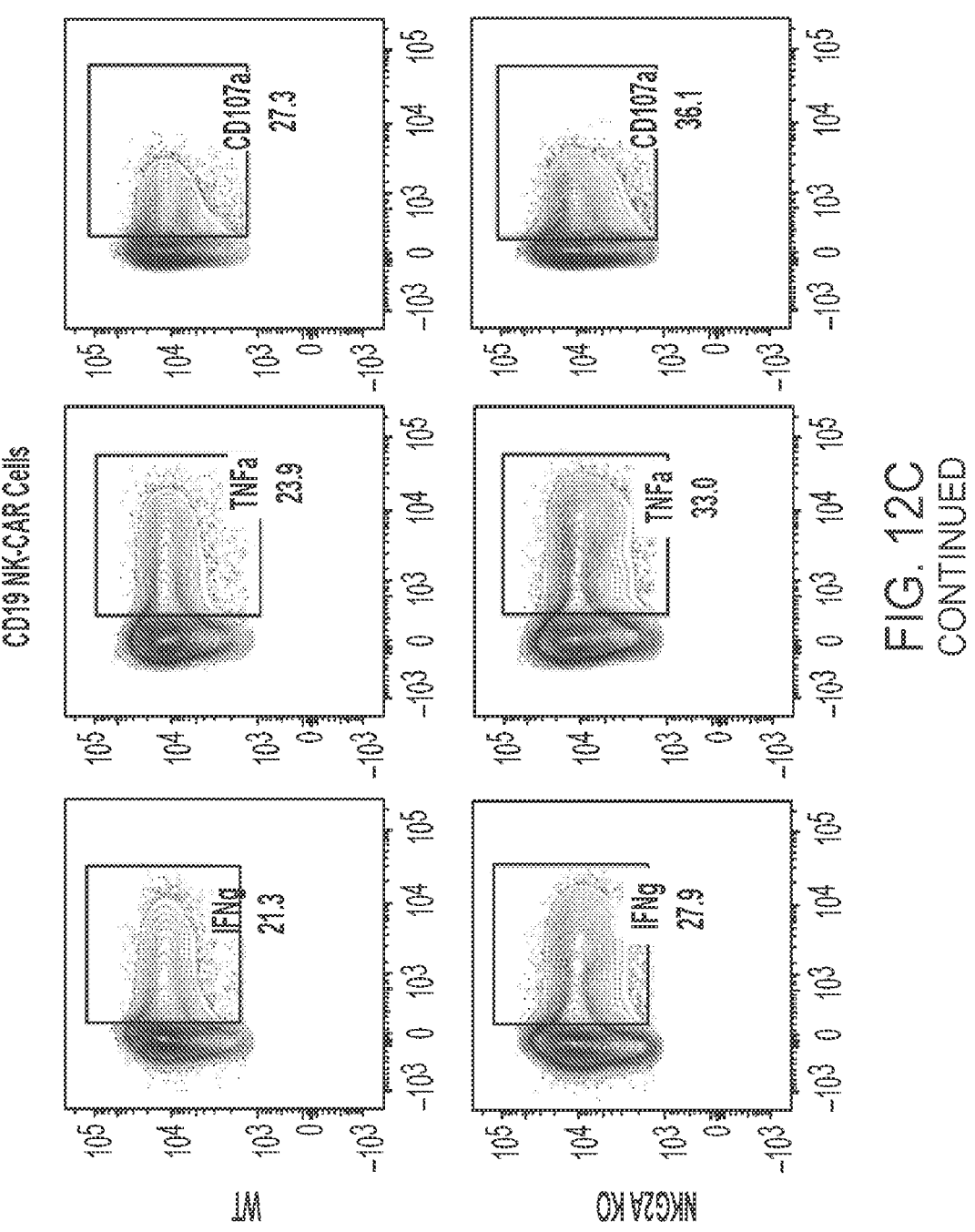

Further studies showed that disruption of SHP1 in NK cells leads to enhanced antitumor efficacy (FIGS. 9 and 10). NK cells were co-cultured with K562\Raji cells at a 1:1 ratio for 4 hours. After the incubation, the cells were stained with annexin V and live and dead cells were analyzed. The K562 cells are sensitive to NK cell killing and the Raji cells are resistant to NK cell killing. In addition, disruption of NKG2A in NK-CAR cells led to enhanced antitumor efficacy against Raji targets (FIG. 12).

Figure 13:
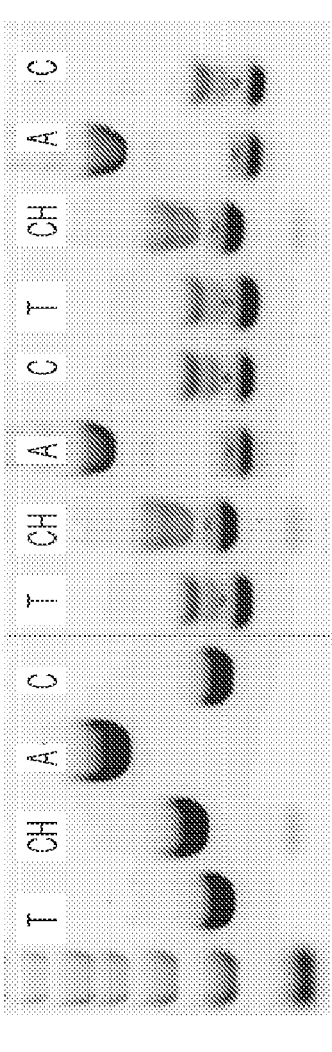
FIG. 13: The approach was validated with another set of genes—TIGIT (T), CD96 (C), CISH (CH), and Adenosine (ADORA2A) (A). For this set of genes, TIGIT and CD96 were knocked out in one set of NK cells during the first round of electroporation. CISH and Adenosine (ADORA2A) were targeted for the second round of knockout in the TIGIT and CD96 KO cells. Knockout efficiency was successfully validated using PCR and flow-cytometry for both rounds of electroporation. The red (peaks on the right) and blue (peaks on the left) histograms in the flow panels represent expression of the protein before and after CRISPR KO, respectively.
Figure 13:
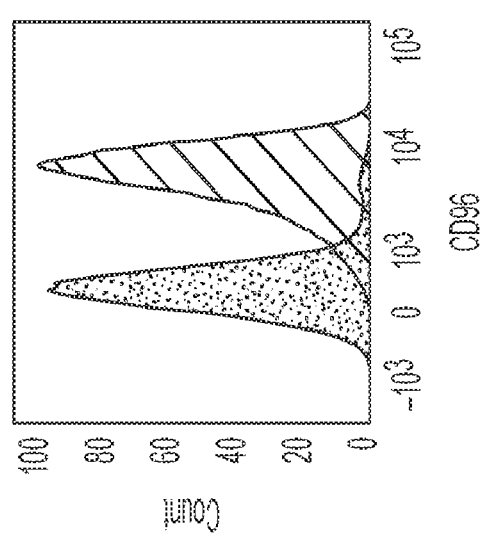
Figure 13:
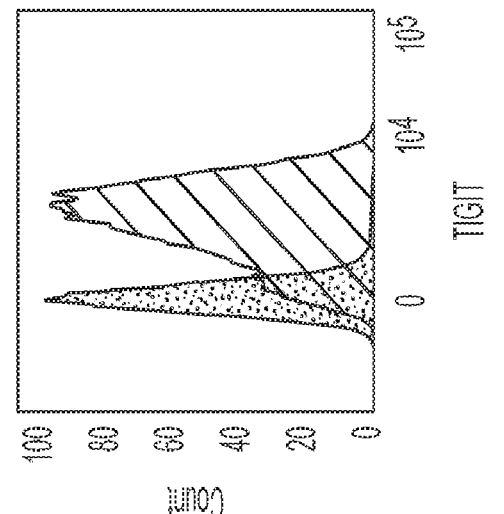
Figure 13:
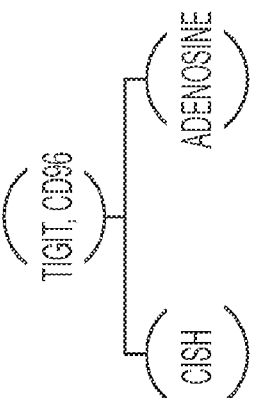
Figure 14:
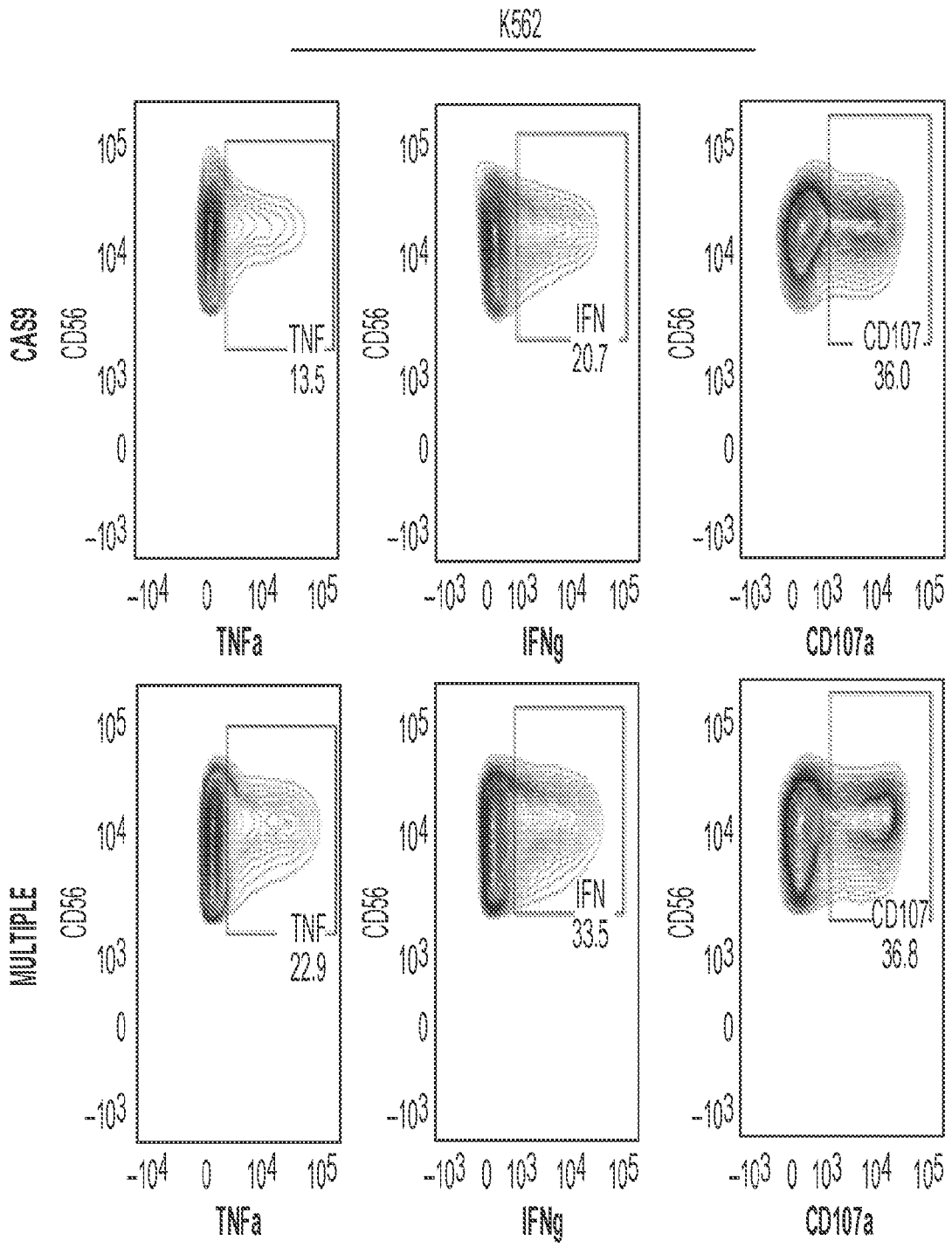
FIG. 14: Disruption of multiple genes in NK cells leads to enhanced antitumor efficacy. To evaluate this, multiple gene (NKG2A, CISH, TGFBRII and Adenosine (ADORA2A)) knockout cells and cells electroporated with cas9 only were used as the control with K562 (NK sensitive) and Raji (NK resistant) cells for 5 hours. NK cell function was evaluated by flow cytometric measurement and observed increases in TNFα, IFNγ, and CD107a in KO cells upon target cell line stimulation.
Figure 14:
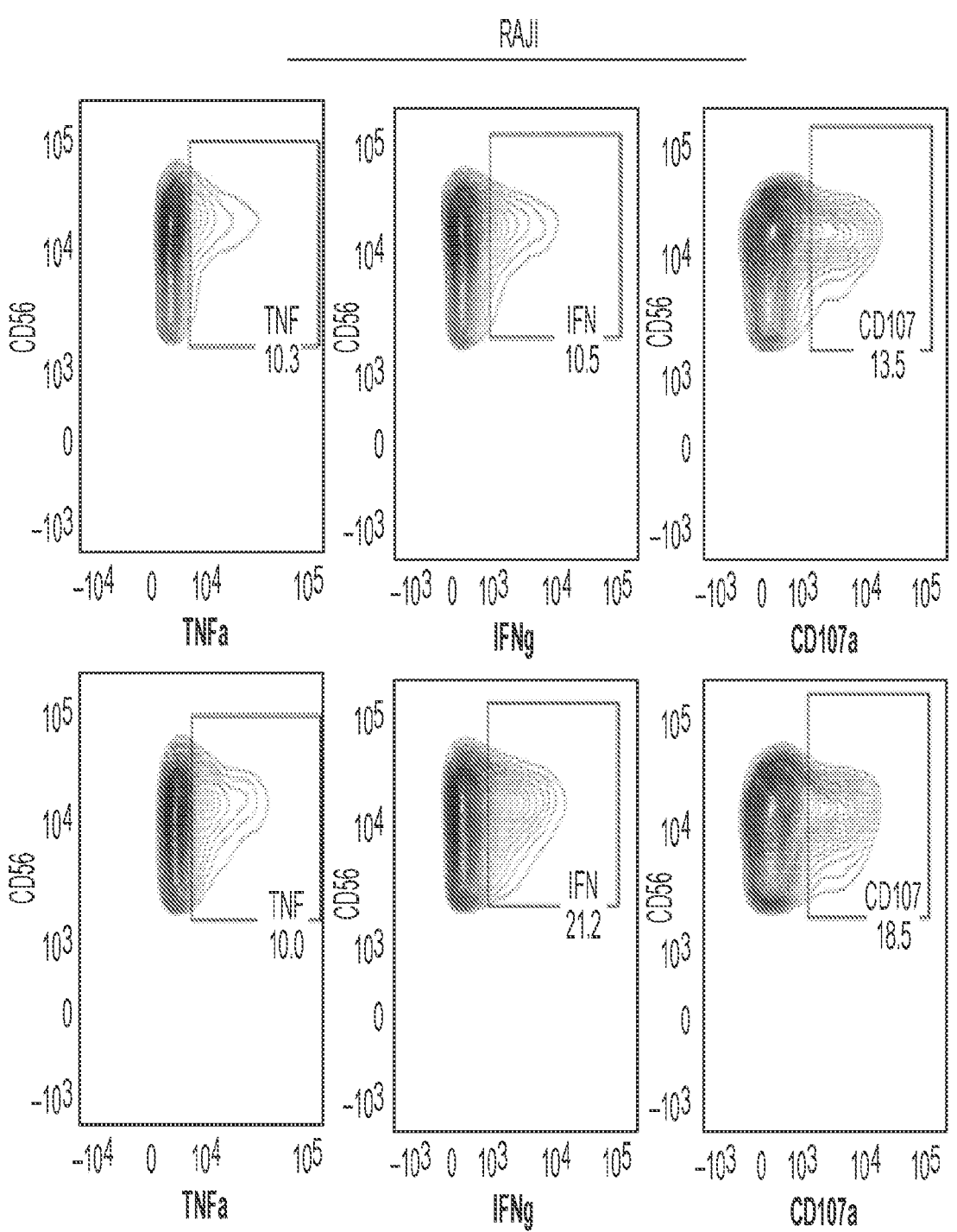
Figure 14:
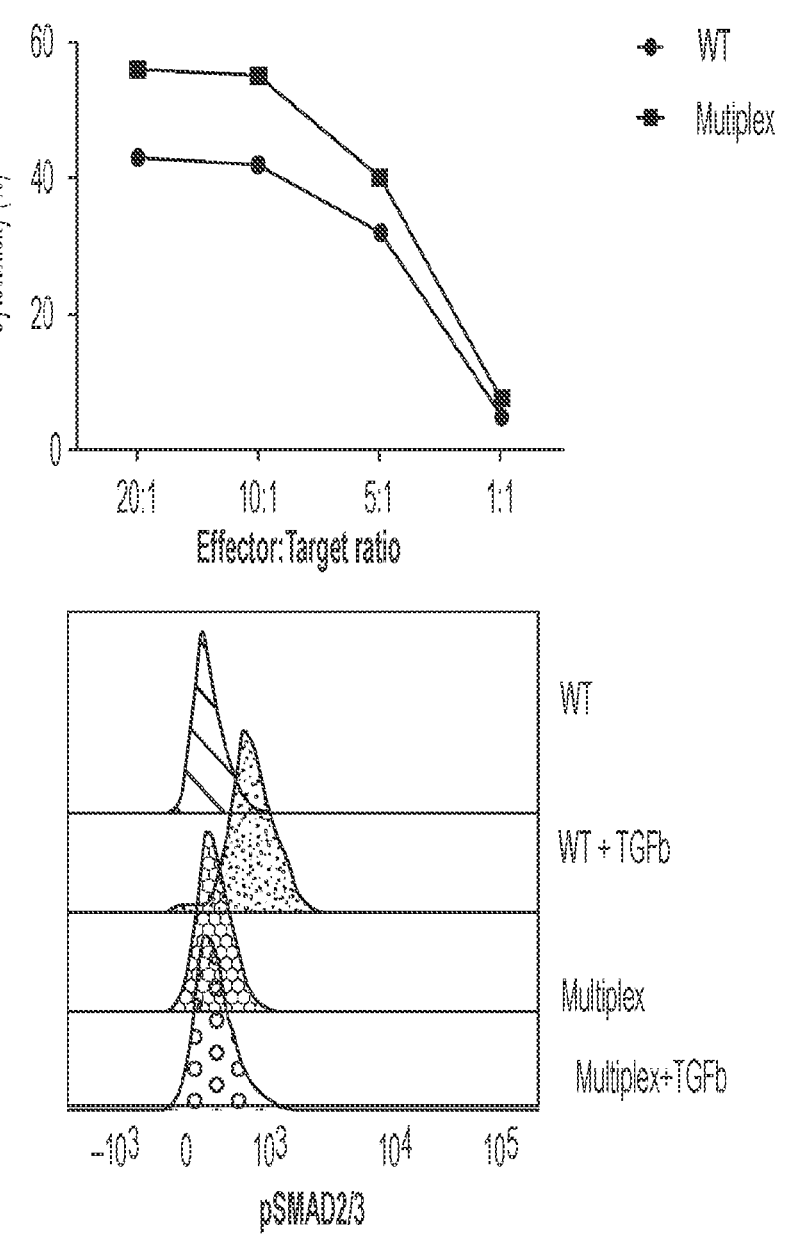
Figure 15:
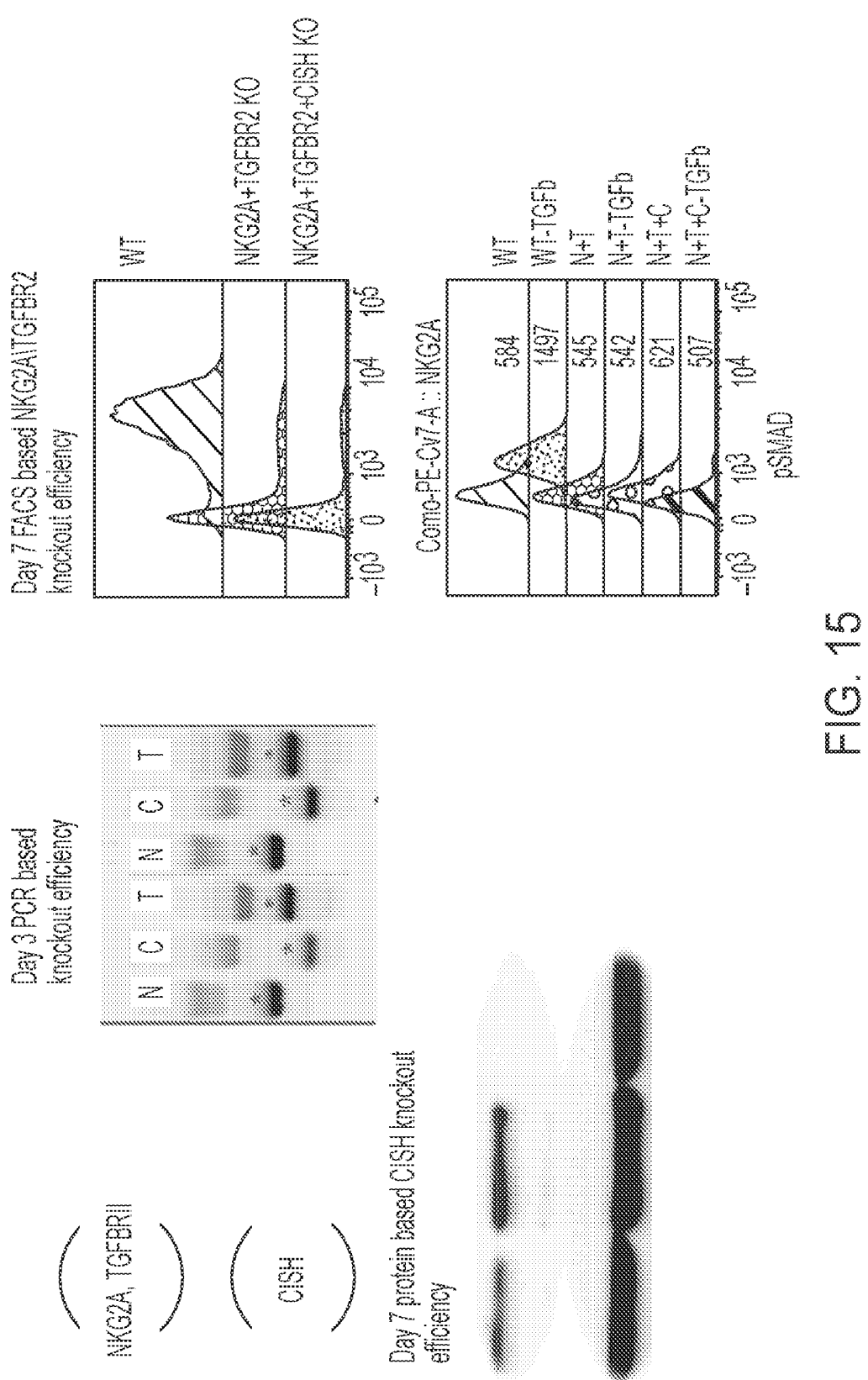
FIG. 15: Disruption of multiple genes in NK cells leads to enhanced antitumor efficacy. To evaluate this, multiple gene (NKG2A, CISH, TGFBRII) knockout cells and cells electroporated with cas9 only were used as the control. NKG2A expression was confirmed by flow cytometry. The addition of exogenous TGF-β failed to induce activation of pSMAD in the KO CAR-NK cells
Figure 16:
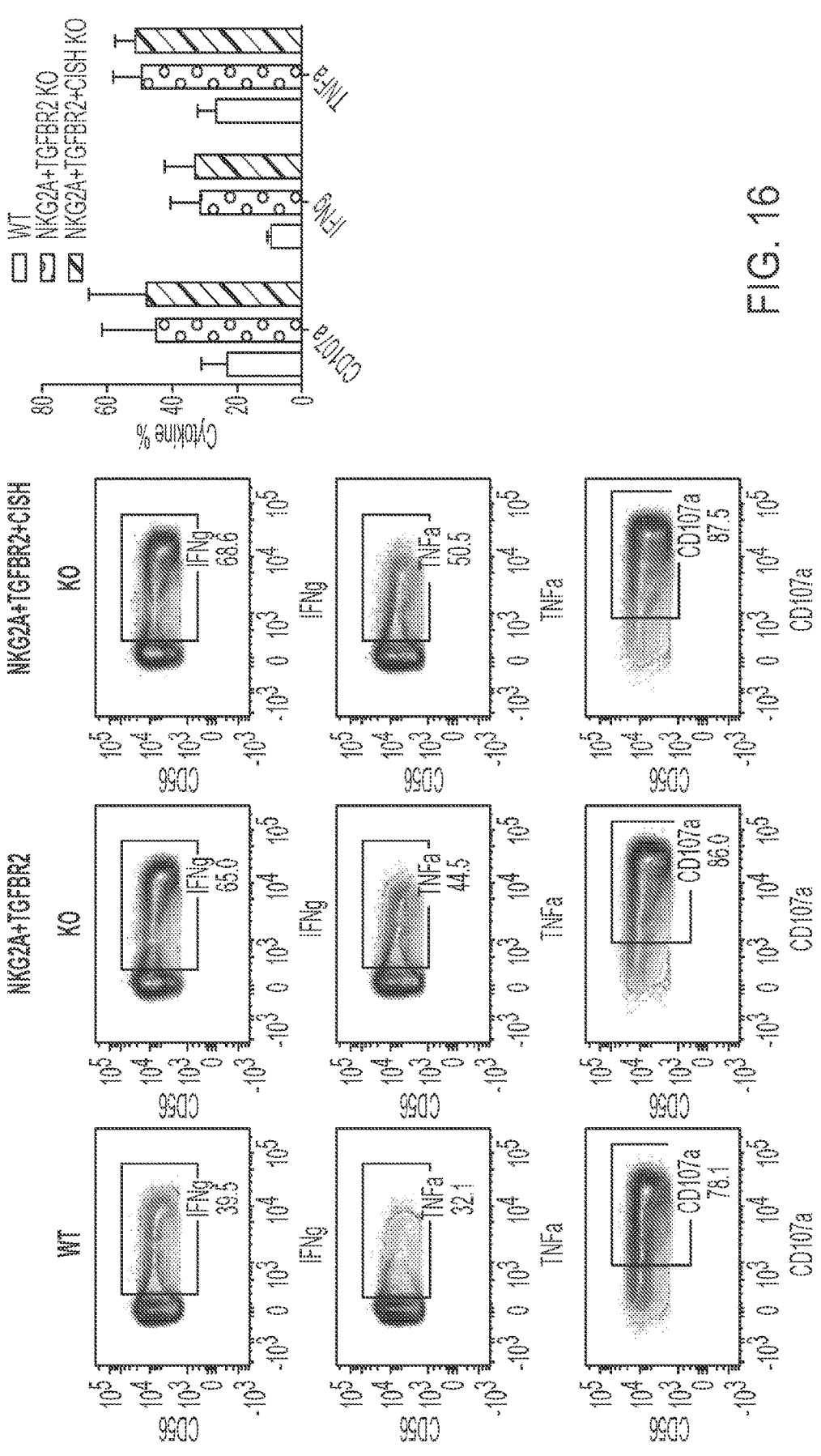
FIG. 16: Disruption of multiple genes (NKG2A, TGFβR2 and CISH) in NK-CAR cells leads to enhanced antitumor efficacy.
Figure 16:
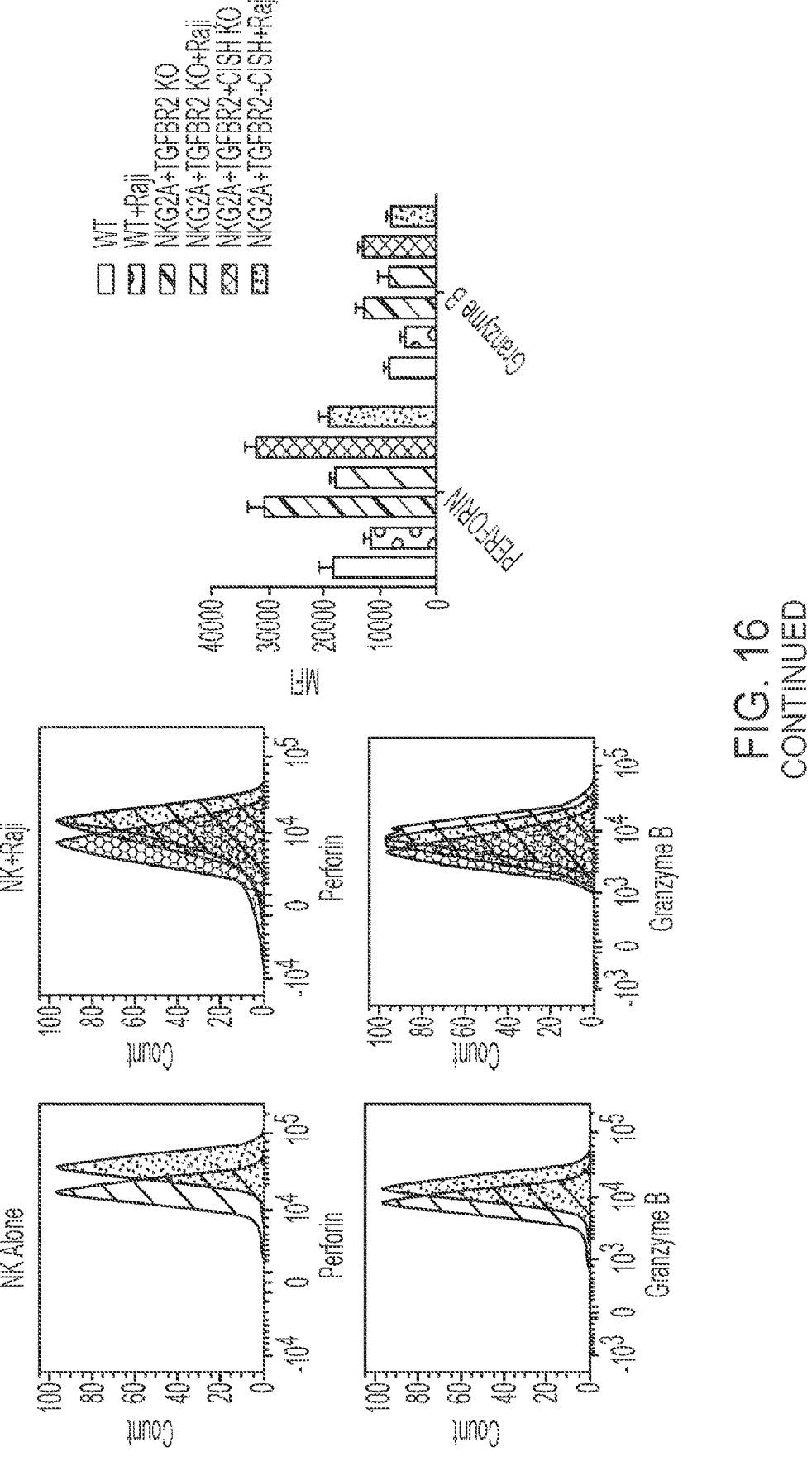
Figure 16:
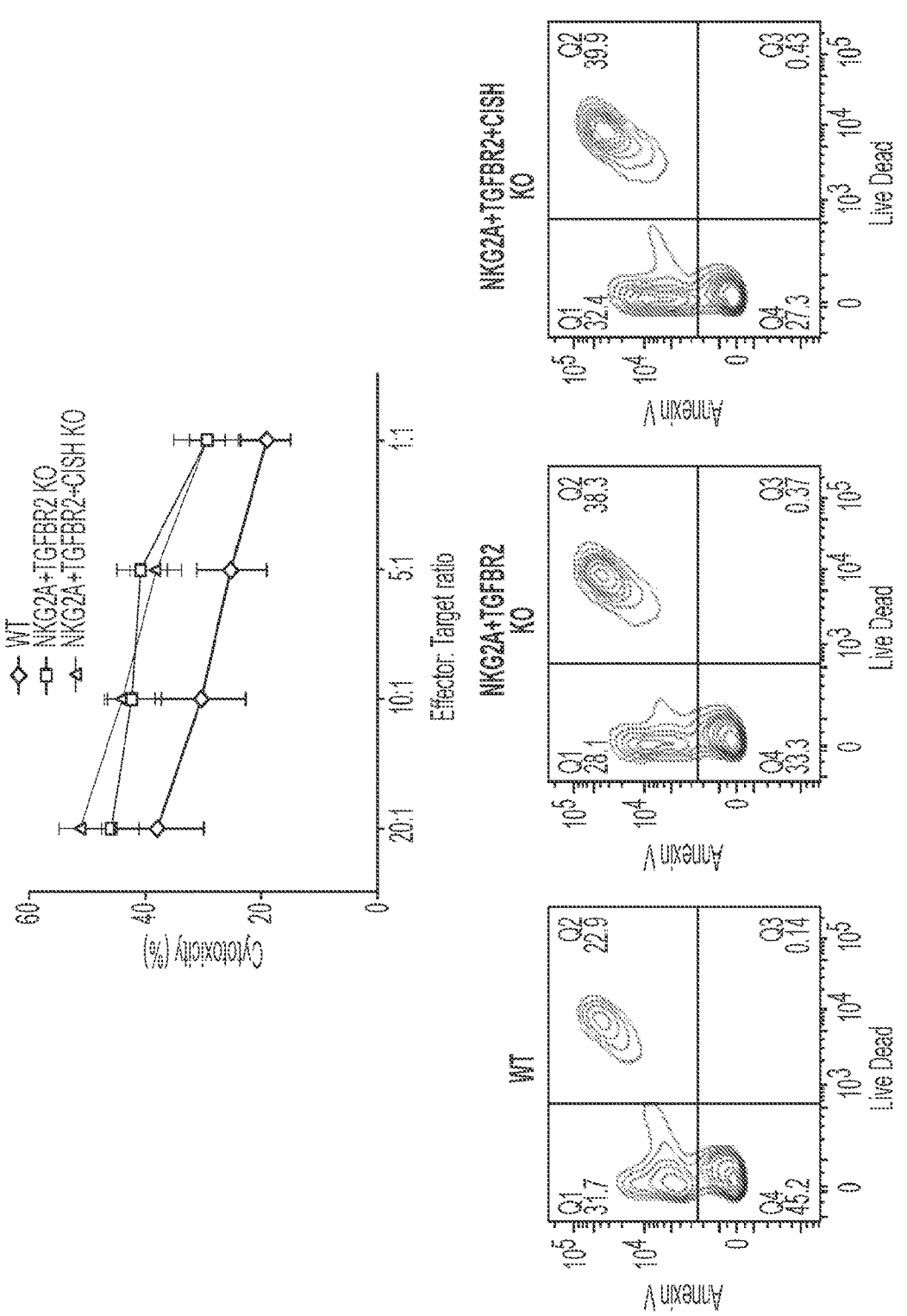
Figure 17:
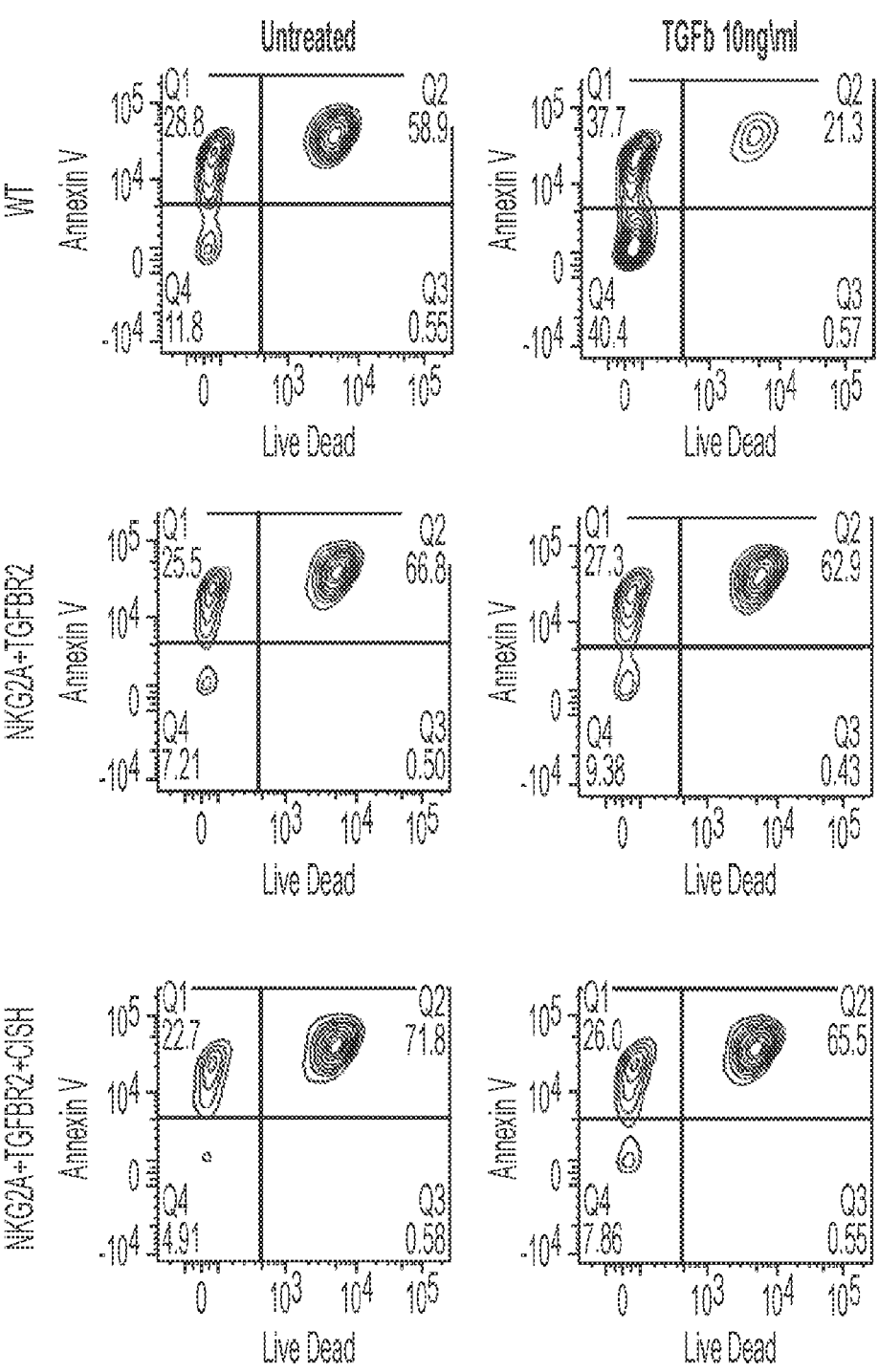
FIG. 17: TGFβR2 KO protects NK-CAR cells from the suppressive effect of TGFβ.
Figure 17:
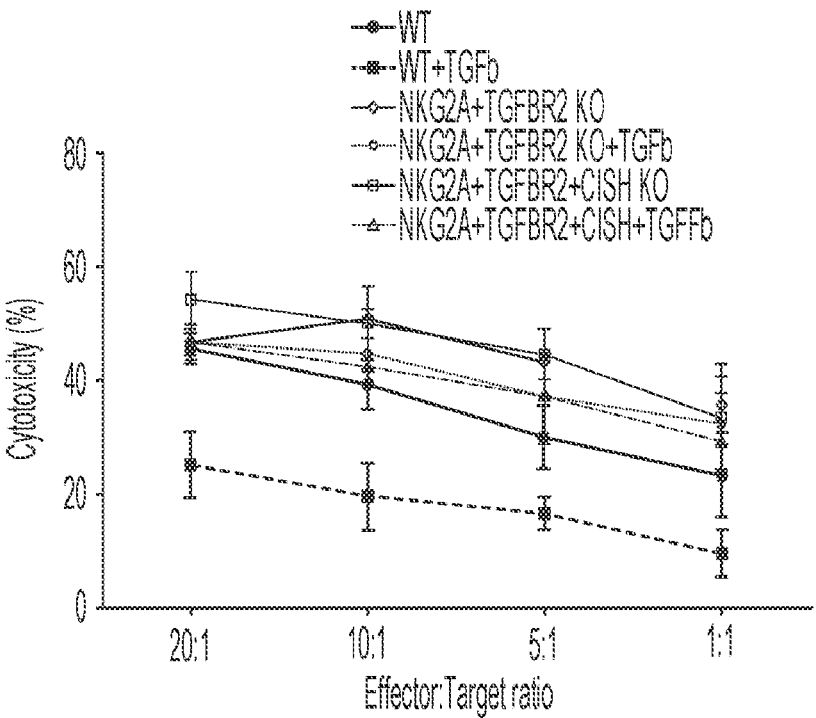
Figure 17:
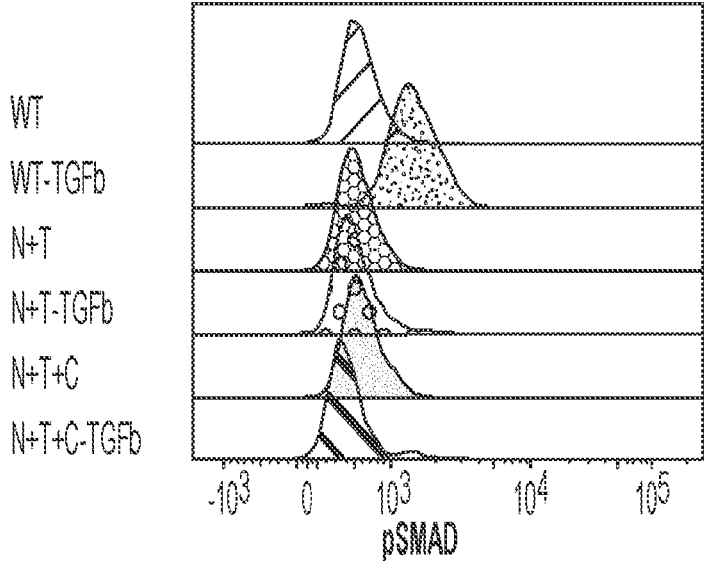
Figure 18:
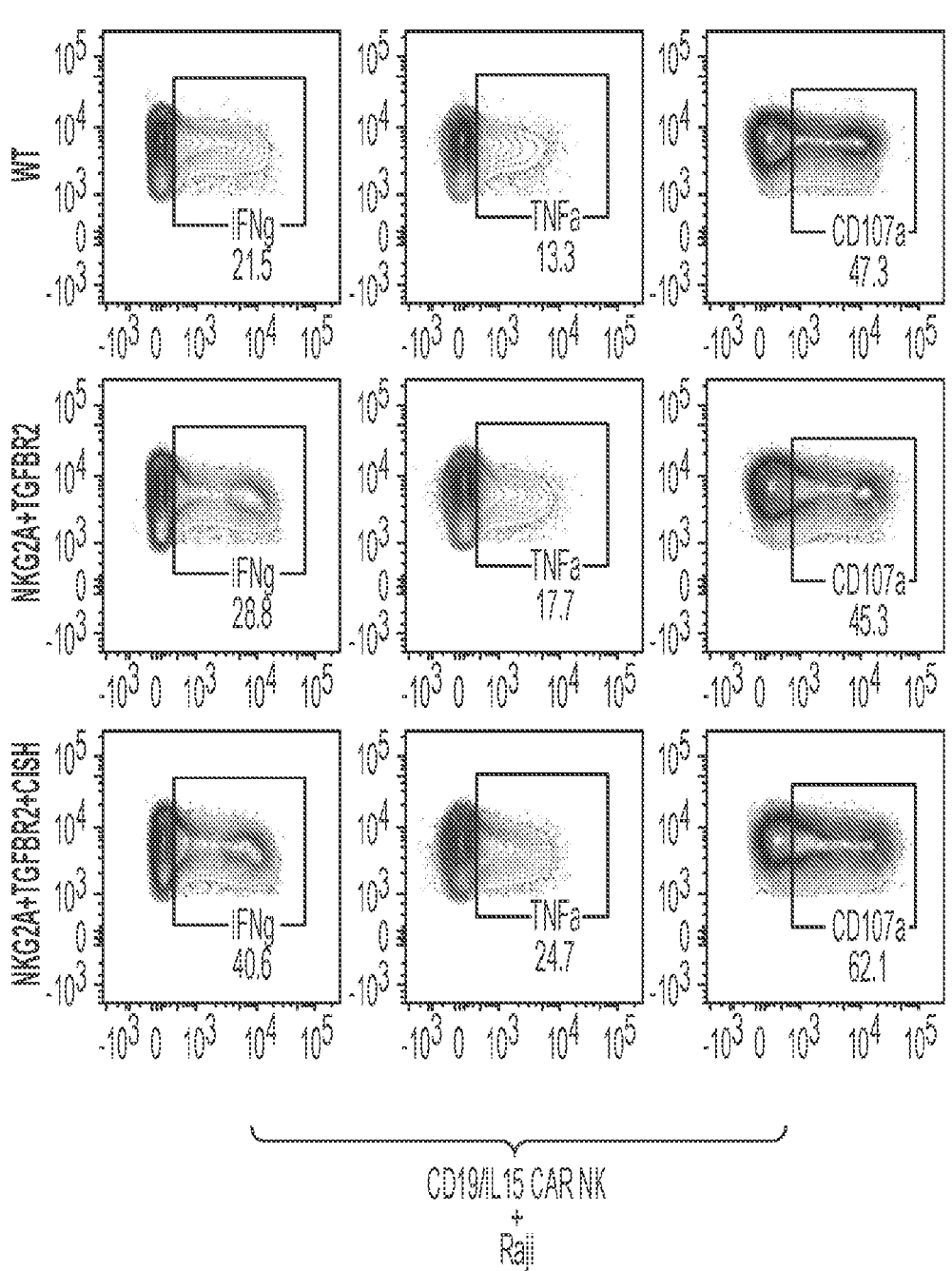
FIG. 18: Multiplex gene editing is reproducible with different NK-CAR constructs and against different targets.
Figure 18:
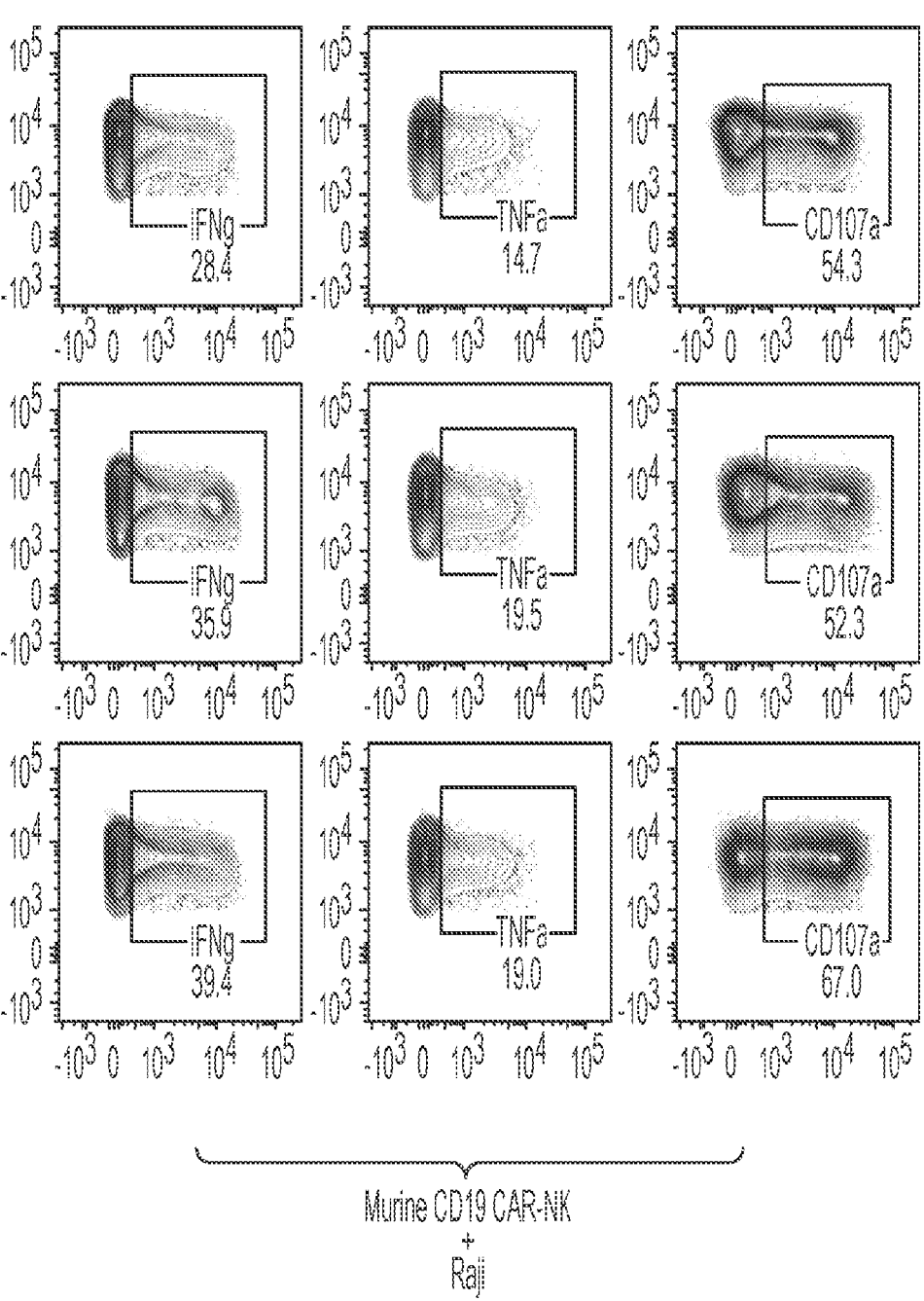
Figure 18:
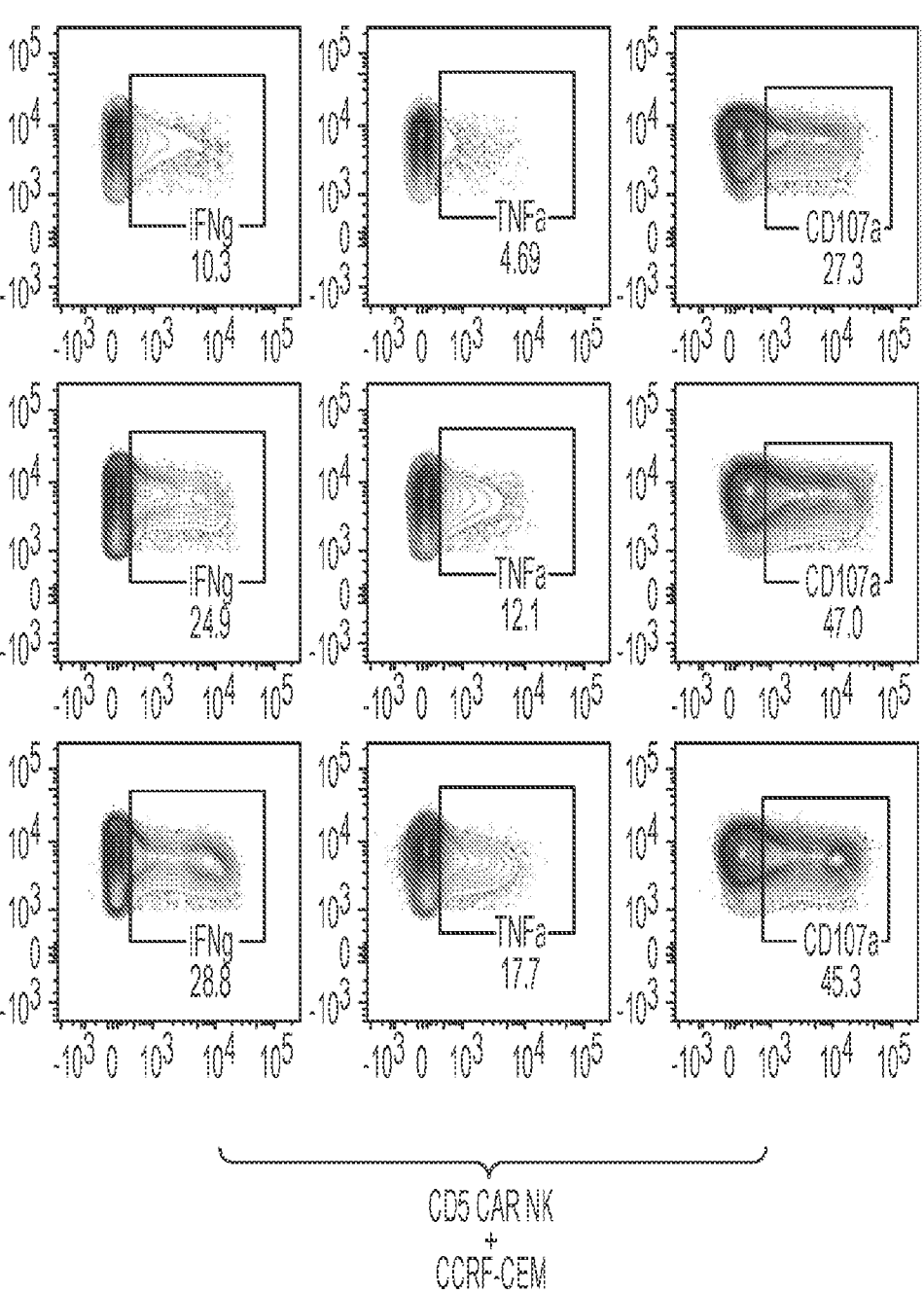
Figure 19:
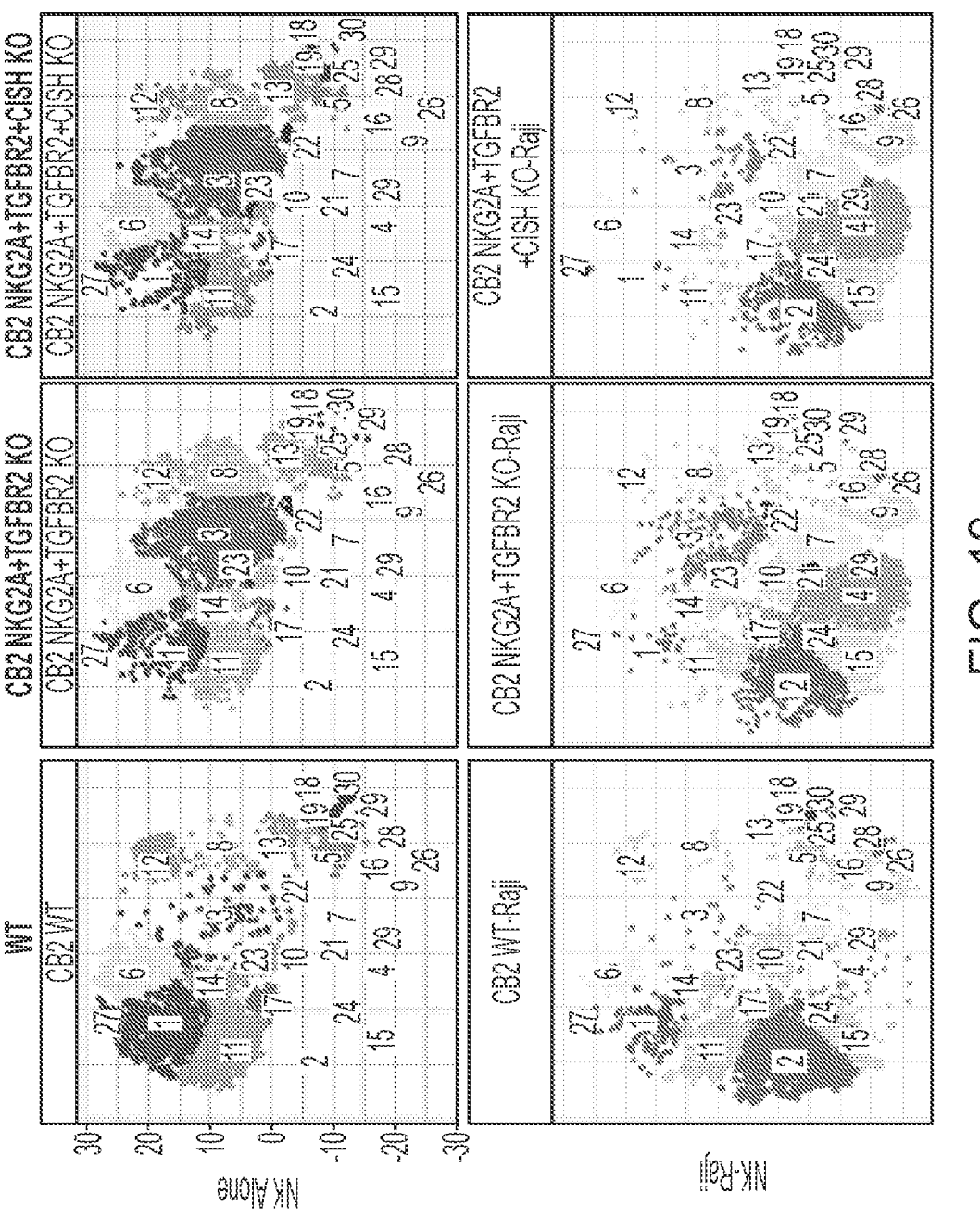
FIG. 19: Multiplex gene editing of multiple inhibitory genes maintains NK architecture and protects NK cells from exhaustion induced by TFGβ.
Figure 19:
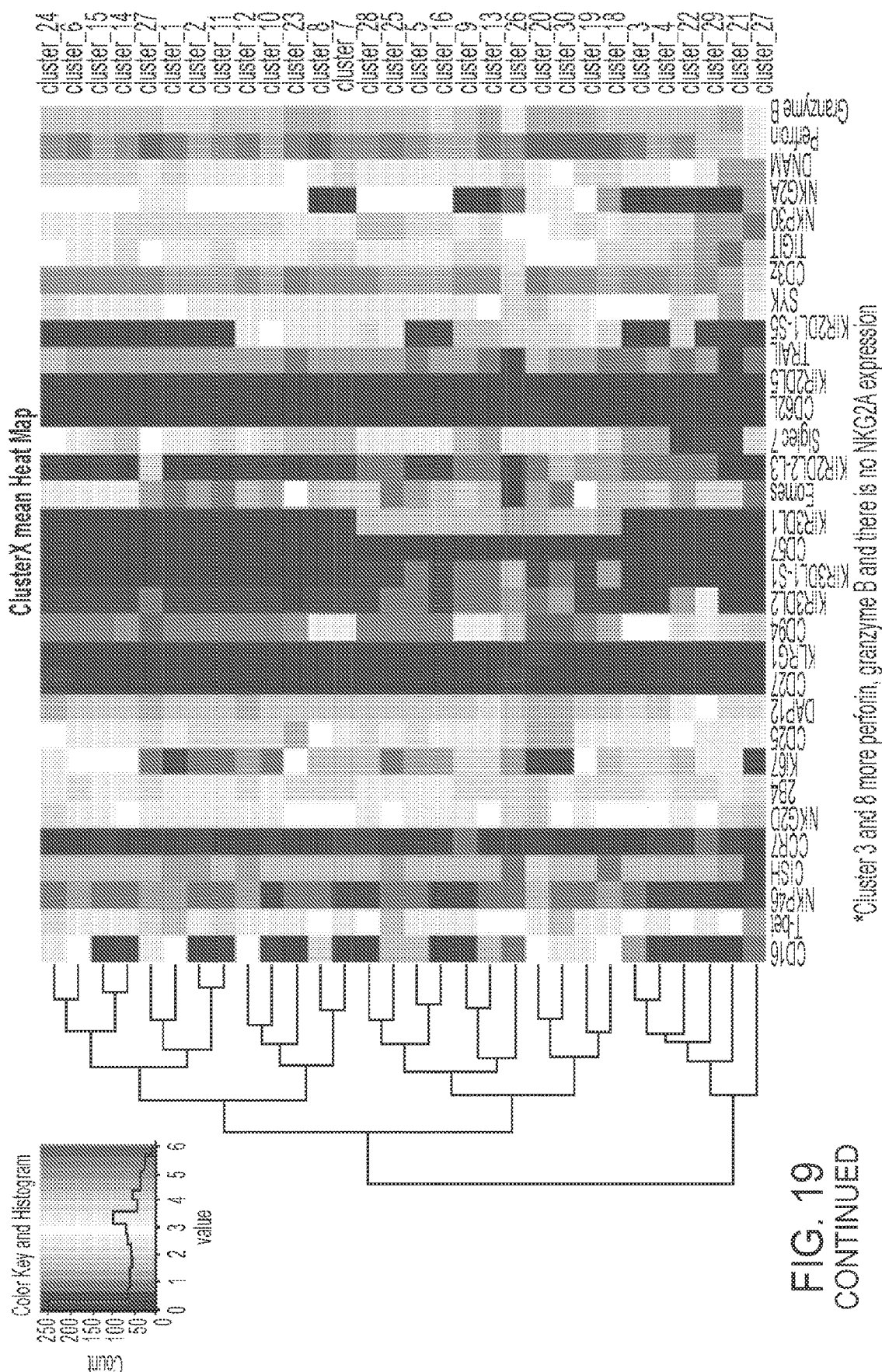

The present approach was further validated with additional sets of genes—TIGIT, CD96, CISH, and ADENOSINE as well as NKG2A, CISH, TGFBRII and ADENOSINE. NK cell function was evaluated by flow cytometric measurement and an increase was observed in TNFα, IFNγ, and CD107a in the cells upon target cell line stimulation (FIGS. 13-14).

Thus, the present methods can be used to simultaneously disrupt expression of multiple genes in immune cells to increase their functionality.

Example 2—Methods sgRNA-Cas9 pre-complexing and Electroporation: 1 or 2 sgRNAs spanning close regions were designed and used for each gene. 1 ug cas9 (PNA Bio) and 500 ng sgRNA (sum of all sgRNAs) reactions were made for each gene and incubated on ice for 20 minutes. After 20 minutes, 250,000 NK Cells were re-suspended in T-buffer* (included with Neon Electroporation Kit, Invitrogen, total volume including RNP complex and cells should be 14 ul) and electroporated with 10 ul electroporation tip using Neon Transfection System. The electroporation conditions are 1600V, 10 ms, and 3 pulses* for NK cells. The cells were then added to culture plate with APCs (1 NK:2 APCs), SCGM media (preferentially antibiotic free), 2001U/ml IL2 and allowed to recover in 37° C. incubator.

crRNA pre-complexing and Electroporation: The crRNA and tracrRNA duplex was mixed with a pipette and centrifuges. The mixture was incubated at 95° C. for 5 min in a thermocycler and then allowed to cool to room temperature on the benchtop.

TABLE 3

| | volume | concentration | | volume | concentration |
|---|---|---|---|---|---|
| | | crNRA and tracrRNA duplex. | | | |
| crRNA # 1 | 2.2 ul | 100 uM | crRNA # 2 | 2.2 ul | 100 uM |
| tracrRNA | 2.2 ul | 100 uM | tracrRNA | 2.2 ul | 100 uM |
| IDTE Buffer | 5.6 ul | | IDTE Buffer | 5.6 ul | |
| total volume | 10 ul | 44 uM | total volume | 10 ul | 44 uM |

The starting concentration of crRNA and tracrRNA are 100 uM. The final concentration after mixing them in equimolar concentration is 44 uM.

TABLE 4

| | volume |
|---|---|
| | Cas9 Nuclease. |
| Alt-R S.p. Cas9 Nuclease 3NLS (61 uM) | 3 ul |
| T buffer | 7 ul |
| total volume | 10 ul |
| final concentration | 18 uM |

TABLE 5

| | volume |
|---|---|
| | Combination of the crRNA: tracrRNA and Cas9 nuclease mix. |
| crRNA # 1: tracrRNA duplex (Step 1) | 2 ul |
| Cas9 (Step 2) | 2 ul |
| total volume | 4 ul |

The crRNA:tracrRNA duplex was combined with the Cas9 Nuclease Mix with pipette, and incubated at room temperature for 15 min. The mixture was then combined with crRNA.

TABLE 6

| | volume |
|---|---|
| | crRNA # 1 and crRNA # 2. |
| crRNA # 1 + tracrRNA + cas9 (Step 3) | 2.25 ul |
| crRNA # 2 + tracrRNA + cas9 (Step 3) | 2.25 ul |
| total volume | 4.5 ul |

Electroporation was performed by first preparing culture plates with APCs (1 NK:2 APCs), SCGM media (preferably antibiotic free), and 200 IU/mL IL-2. Prepare 250,000 cells per well were re-suspended in 7.5 ul T buffer just before use. The electroporation conditions were 1600V, 10 ms, and 3 pulses*. The cells were then added to culture plate and allowed to recover in a 37° C. incubator.

NK Cell expansion: Isolate NK cells from cord blood or peripheral blood using NK cell isolation kit from Miltenyi (130-092-657). Put NK cells with Feeder cell at 1:2 ratio (1 NK cell 2 Feeder cells) in the presence of IL2 (200 IU\ml) in SCGM media. Change media every other day with IL2. On day 4 reselect NK cells using NK cell isolation KIT to remove feeder cells or wait for day 7 until all feeder cells are gone. Transduce with chimeric antigen receptor or electroporate for Crispr-Cas9.

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An engineered natural killer (NK) cell with knockout of at least two gene products,
   wherein the at least two gene products are selected from the group consisting of NK Cell Receptor A (NKG2A) and Cytokine Inducible SH2-Containing Protein (CISH),
   wherein knockout comprises the elimination or reduction of level of expression of the at least two gene products, compared to the level of expression of the at least two gene products in the absence of the knockout.

2. The engineered NK cell of claim 1, wherein the engineered NK cell is produced according to an in vitro method for the disruption of the at least two genes.

3. The engineered NK cell of claim 1, wherein the engineered NK cell is isolated from cord blood.

4. The engineered NK cell of claim 1,
   wherein the NK cell is engineered to express a chimeric antigen receptor (CAR),
   wherein the CAR comprises an antigen-binding domain that targets one or more tumor associated antigens.

5. The engineered NK cell of claim 4, wherein the CAR is inserted at a gene selected from the group consisting of NKG2A and CISH.

6. The engineered NK cell of claim 5, wherein the CAR is under the control of the endogenous promoter of said gene.

7. The engineered NK cell of claim 5, wherein the CAR was inserted at the gene locus by CRISPR-mediated gene editing.

8. The engineered NK cell of claim 1, wherein the engineered NK cell is engineered to express a heterologous cytokine selected from the group consisting of IL-7, IL-2, IL-15, IL-12, IL-18, IL-21, and a combination thereof.

9. The engineered NK cell of claim 1, wherein the engineered NK cell further comprises a polynucleotide encoding a CAR.

10. The engineered NK cell of claim 1, wherein the engineered NK cell further comprises a polynucleotide encoding interleukin 15 (IL-15).

11. The engineered NK cell of claim 1, wherein the at least two genes are NKG2A and CISH and the engineered NK cell further comprises one or more polynucleotide encoding a CAR and IL-15.

12. The engineered NK cell of claim 1,
   wherein the knockout comprises one or more insertions, one or more frameshift mutations, one or more missense mutations, one or more deletions, or knock-in of the at least two genes or part of the at least two genes encoding the gene products.

13. An engineered NK cell with knockout of at least two gene products,
   wherein the at least two gene products are
   Transforming Growth Factor Beta Receptor 2 (TGFBR2) and Nuclear Receptor Subfamily 3 Group C Member 1 (NR3C1)
   wherein knockout comprises the elimination or reduction of level of expression of the at least two gene products, compared to the level of expression of the at least two gene products in the absence of the knockout,
   wherein the engineered NK cell is engineered to express a CAR, wherein the CAR comprises one or more antigen-binding domain that targets one or more tumor associated antigens.

14. The engineered NK cell of claim 13, wherein the one or more tumor associated antigen is selected from the group consisting of Tumor-associated calcium signal transducer 2 (TACSTD2), Epidermal Growth Factor Receptor (EGFR), and EGFR variant III (EGFRvIII).

\* \* \* \* \*